United States Patent
Wilde et al.

(10) Patent No.: US 6,958,341 B2
(45) Date of Patent: Oct. 25, 2005

(54) PYRAZOLOPYRIMIDINES AS CRF ANTAGONISTS

(75) Inventors: Richard G. Wilde, Newark, DE (US); Paul J. Gilligan, Wilmington, DE (US)

(73) Assignee: Bristol-Myers Squibb Pharma Company, Princeton, NJ (US)

(*) Notice: Subject to any disclaimer, the term of this patent is extended or adjusted under 35 U.S.C. 154(b) by 79 days.

(21) Appl. No.: 10/125,623

(22) Filed: Apr. 18, 2002

(65) Prior Publication Data
US 2003/0139426 A1 Jul. 24, 2003

Related U.S. Application Data

(63) Continuation of application No. 09/543,291, filed on Apr. 5, 2000, now abandoned.
(60) Provisional application No. 60/128,006, filed on Apr. 6, 1999.

(51) Int. Cl.[7] .................... C07D 487/04; A61K 31/519
(52) U.S. Cl. ..................... 514/259.3; 544/281
(58) Field of Search ................ 514/259.3; 544/281

(56) References Cited

U.S. PATENT DOCUMENTS

| | | | |
|---|---|---|---|
| 3,910,907 A | 10/1975 | O'Brien et al. | 544/212 |
| 3,920,652 A | 11/1975 | Springer et al. | 544/281 |
| 3,995,039 A | 11/1976 | Rooney et al. | 514/246 |
| 4,021,556 A | 5/1977 | Springer et al. | 514/259.3 |
| 4,567,263 A | 1/1986 | Eicken et al. | 544/263 |
| 4,621,556 A | 11/1986 | Soltysiak et al. | 83/610 |
| 4,892,576 A | 1/1990 | Kruger et al. | 504/133 |
| 4,997,940 A | 3/1991 | Vinogradoff et al. | 549/281 |
| 5,137,887 A | 8/1992 | Hashimoto et al. | 514/246 |
| 5,397,774 A | 3/1995 | Nugent et al. | 514/81 |
| 5,484,760 A | 1/1996 | Bussler et al. | 504/103 |

FOREIGN PATENT DOCUMENTS

| | | |
|---|---|---|
| DE | 4243279 | 6/1994 |
| EP | 0025819 A | 4/1981 |
| EP | 0129847 A | 1/1985 |
| EP | 0374448 | 6/1990 |
| EP | 0531901 | 3/1993 |
| EP | 0511528 | 2/1994 |
| EP | 0549149 | 4/1994 |
| EP | 0662477 | 7/1995 |
| EP | 0269859 | 10/1995 |
| EP | 0714898 | 6/1996 |
| EP | 0521622 | 8/1997 |
| EP | 0591528 | 12/1998 |
| WO | 9510506 | 4/1995 |
| WO | 9535298 | 12/1995 |
| WO | 9729109 | 8/1997 |
| WO | 9803510 | 1/1998 |
| WO | 9808847 | 3/1998 |
| WO | 9901454 | 1/1999 |

OTHER PUBLICATIONS

Suzuki, M.; Iwasaki, H.; Fujikawa, Y.; Sakashita, M.; Kitahara, M.; Sakoda, R., Bioorganic & Medicinal Chemistry Letters, 11(10), 1285–1288, 2001.*
McCarthy, J.R. et al, Ann. Reports Med. Chem., vol. 34, 1999, 11–20.*
Springer et al, J. Med. Chem., 1976, vol. 19, No. 2, 291–296.
Joshi et al., J. Prakt. Chemie, 321, 2, 1979, 341–344.
Maquestiau et al., Bull. Soc. Belg., vol. 101, No. 2, 1992, pp. 131–136.
Ibrahim et al., Arch. Pharm. (weinheim) 320, 487–491 (1987).
J. Med. Chem. 24, 610–613 (1981).
J. Het. Chem., 22, 601 (1985).

* cited by examiner

Primary Examiner—Thomas C. McKenzie
(74) Attorney, Agent, or Firm—Woodcock Washburn LLP; Shad R. Makujina

(57) ABSTRACT

The present invention relates to pyrazolopyrimidines according to formula (I)

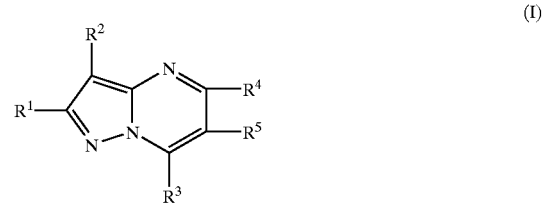

(I)

and stereoisomers, isomers and salts thereof wherein $R^1$–$R^5$ are selected from certain alkyl, aryl and heteroaryl species as defined in the specification wherein all of the compounds are useful as CRF antagonists and are thus useful in the treatment of neurological disorders as well as a multitude of other CRF associated diseases or conditions.

11 Claims, No Drawings

PYRAZOLOPYRIMIDINES AS CRF ANTAGONISTS

CROSS-REFERENCE TO RELATED APPLICATIONS

This application is a continuation of U.S. application Ser. No. 09/543,291, filed Apr. 5, 2000, now abandoned, which in turn claimed priority to U.S. Provisional Application Ser. No. 60/128,006, filed Apr. 6, 1999. The disclosures of these prior applications are incorporated herein by reference in their entirety.

FIELD OF THE INVENTION

The present invention relates to novel compounds, compositions, and methods for the treatment of psychiatric disorders and neurological diseases, including major depression, anxiety-related disorders, post-traumatic stress disorder, supranuclear palsy and feeding disorders, as well as treatment of immunological, cardiovascular or heart-related diseases and colonic hypersensitivity associated with psychopathological disturbance and stress. In particular, the present invention relates to novel pyrazolo[1,5-a]pyrimidines, pharmaceutical compositions containing such compounds and their use in treating psychiatric disorders, neurological diseases, immunological, cardiovascular or heart-related diseases and colonic hypersensitivity associated with psychopathological disturbance and stress.

BACKGROUND OF THE INVENTION

Corticotropin releasing factor (herein referred to as CRF), a 41 amino acid peptide, is the primary physiological regulator of proopiomelanocortin (POMC)-derived peptide secretion from the anterior pituitary gland [J. Rivier et al., Proc. Nat. Acad. Sci. (USA) 80:4851 (1983); W. Vale et al., Science 213:1394 (1981)]. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in brain [W. Vale et al., Rec. Prog. Horm. Res. 39:245 (1983); G. F. Koob, Persp. Behav. Med. 2:39 (1985); E. B. De Souza et al., J. Neurosci. 5:3189 (1985)]. There is also evidence that CRF plays a significant role in integrating the response of the immune system to physiological, psychological, and immunological stressors [J. E. Blalock, Physiological Reviews 69:1 (1989); J. E. Morley, Life Sci. 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, Hosp. Practice 23:59 (1988)].

In affective disorder, or major depression, the concentration of CRF is significantly increased in the cerebral spinal fluid (CSF) of drug-free individuals [C. B. Nemeroff et al., Science 226:1342 (1984); C. M. Banki et al., Am. J. Psychiatry 144:873 (1987); R. D. France et al., Biol. Psychiatry 28:86 (1988); M. Arato et al., Biol Psychiatry 25:355 (1989)]. Furthermore, the density of CRF receptors is significantly decreased in the frontal cortex of suicide victims, consistent with a hypersecretion of CRF [C. B. Nemeroff et al., Arch. Gen. Psychiatry 45:577 (1988)]. In addition, there is a blunted adrenocorticotropin (ACTH) response to CRF (i.v. administered) observed in depressed patients [P. W. Gold et al., Am J. Psychiatry 141:619 (1984); F. Holsboer et al., Psychoneuroendocrinology 9:147 (1984); P. W. Gold et al., New Eng. J. Med. 314:1129 (1986)]. Preclinical studies in rats and non-human primates provide additional support for the hypothesis that hypersecretion of CRF may be involved in the symptoms seen in human depression [R. M. Sapolsky, Arch. Gen. Psychiatry 46:1047 (1989)]. There is preliminary evidence that tricyclic antidepressants can alter CRF levels and thus modulate the numbers of CRF receptors in brain [Grigoriadis et al., Neuropsychopharmacology 2:53 (1989)].

It has also been postulated that CRF has a role in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., Life Sci. 31:363 (1982); C. W. Berridge and A. J. Dunn Regul. Peptides 16:83 (1986)]. Preliminary studies using the putative CRF receptor antagonist a-helical ovine CRF (9-41) in a variety of behavioral paradigms demonstrate that the antagonist produces "anxiolytic-like" effects that are qualitatively similar to the benzodiazepines [C. W. Berridge and A. J. Dunn Horm. Behav. 21:393 (1987), Brain Research Reviews 15:71 (1990)].

Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF in both the conflict test [K. T. Britton et al., Psychopharmacology 86:170 (1985); K. T. Britton et al., Psychopharmacology 94:306 (1988)] and in the acoustic startle test [N. R. Swerdlow et al., Psychopharmacology 88:147 (1986)] in rats. The benzodiazepine receptor antagonist (Rol15-1788), which was without behavioral activity alone in the operant conflict test, reversed the effects of CRF in a dose-dependent manner while the benzodiazepine inverse agonist (FG7142) enhanced the actions of CRF [K. T. Britton et al., Psychopharmacology 94:306 (1988)].

It has been further postulated that CRF has a role in immunological, cardiovascular or heart-related diseases such as hypertension, tachycardia and congestive heart failure, stroke, osteoporosis, premature birth, psychosocial dwarfism, stress-induced fever, ulcer, diarrhea, post-operative ileus and colonic hypersensitivity associated with psychopathological disturbance and stress.

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (a-helical CRF9-41) in a variety of behavioral paradigms have demonstrated that the CRF antagonist produces "anxiolytic-like" effects qualitatively similar to the benzodiazepines [for review see G. F. Koob and K. T. Britton, In: Corticotropin-Releasing Factor: Basic and Clinical Studies of a Neuropeptide, E. B. De Souza and C. B. Nemeroff eds., CRC Press p221 (1990)].

DuPont Merck PCT application U.S. Ser. No. 94/11050 describes corticotropin releasing factor antagonist compounds of the formula:

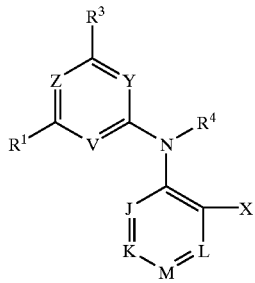

and their use to treat psychiatric disorders and neurological diseases. Included in the description are fused pyridines and pyrimidines of the formula:

where: V is $CR^{1a}$ or N; Z is $CR^2$ or N; A is $CR^3$ or N; and D is $CR^{28}$ or N.

WO 98/03510, published in January, 1998, also describes a series of CRF antagonist compounds having the formula:

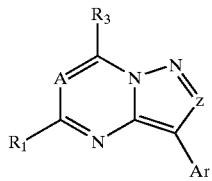

wherein z is N or $CR^2$ and A is N or CR.

WO 97/29109, published in August, 1997, similarly describes certain CRF antagonist compounds having the formula:

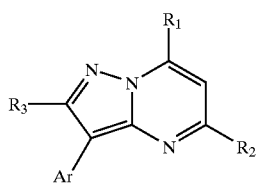

wherein Ar is phenyl, pyridyl and substituted versions thereof.

WO 98/08847, published Mar. 5, 1998, discloses CRF antagonist compounds of the formula:

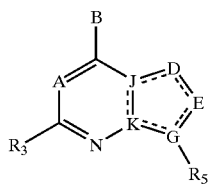

wherein B is selected from a variety of non-aryl groups and $R^5$ is selected from certain groups such as phenyl or pyridyl or substituted versions thereof.

WO 99/01454, published on Jan. 14, 1999, discloses CRF antagonist compounds of the formula:

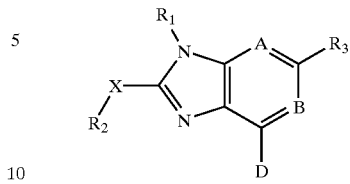

wherein D is an aryl or heteroaryl group and $R^1$ is selected from certain non-aryl or non-heteroaryl groups.

EP 0 269 859 (Ostuka, 1988) discloses pyrazolotriazine compounds of the formula

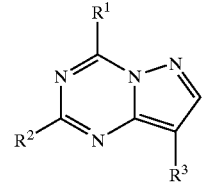

where $R^1$ is OH or alkanoyl, $R^2$ is H, OH, or SH, and $R^3$ is an unsaturated heterocyclic group, naphthyl or substituted phenyl, and states that the compounds have xanthine oxidase inhibitory activity and are useful for treatment of gout.

EP 0 594 149 (Ostuka, 1994) discloses pyrazolotriazine and pyrazolopyrimidine compounds of the formula where A is CH or N, $R^0$ and $R^3$ are H or alkyl, and $R^1$ and $R^2$ are H, alkyl, alkoxyl, alkylthio, nitro, etc., and states that the compounds inhibit androgen and are useful in treatment of benign prostatic hypertrophy and prostatic carcinoma.

U.S. Pat. No. 3,910,907 (ICI, 1975) discloses pyrazolotriazines of the formula:

where $R^1$ is $CH_3$, $C_2H_5$ or $C_6H_5$, X is H, $C_6H_5$, $m$-$CH_3C_6H_4$, CN, COOEt, Cl, I or Br, Y is H, $C_6H_5$, $o$-$CH_3C_6H_4$, or $p$-$CH_3C_6H_4$, and Z is OH, H, $CH_3$, $C_2H_5$, $C_6H_5$, $n$-$C_3H_7$, $i$-$C_3H_7$, SH, $SCH_3$, $NHC_4H_9$, or $N(C_2H_5)_2$, and states that the compounds are c-AMP phosphodiesterase inhibitors useful as bronchodilators.

U.S. Pat. No. 3,995,039 discloses pyrazolotriazines of the formula:

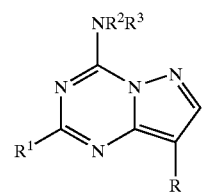

where $R^1$ is H or alkyl, $R^2$ is H or alkyl, $R^3$ is H, alkyl, alkanoyl, carbamoyl, or lower alkylcarbamoyl, and R is pyridyl, pyrimidinyl, or pyrazinyl, and states that the compounds are useful as bronchodilators.

U.S. Pat. No. 5,137,887 discloses pyrazolotriazines of the formula

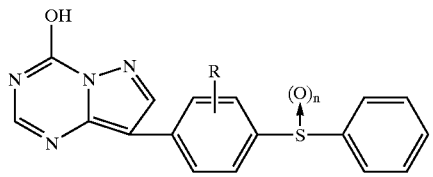

where R is lower alkoxy, and teaches that the compounds are xanthine oxidase inhibitors and are useful for treatment of gout.

U.S. Pat. No. 4,892,576 discloses pyrazolotriazines of the formula
where X is O or S, Ar is a phenyl, naphthyl, pyridyl or thienyl group, $R_6$–$R_8$ are H, alkyl, etc., and $R_9$ is H, alkyl, phenyl, etc. The patent states that the compounds are useful as herbicides and plant growth regulants.

U.S. Pat. No. 5,484,760 and WO 92/10098 discloses herbicidal compositions containing, among other things, a herbicidal compound of the formula

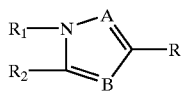

where A can be N, B can be $CR_3$, $R_3$ can be phenyl or substituted phenyl, etc., R is —$N(R_4)SO_2R_5$ or —$SO_2N(R_6)$ $R_7$ and $R_1$ and $R_2$ can be taken together to form
where X, Y and Z are H, alkyl, acyl, etc. and D is O or S.

U.S. Pat. No. 3,910,907 and Senga et al., J. Med. Chem., 1982, 25, 243–249, disclose triazolotriazines cAMP phosphodiesterase inhibitors of the formula
where Z is H, OH, $CH_3$, $C_2H_5$, $C_6H_5$, n-$C_3H_7$, iso-$C_3H_7$, SH, $SCH_3$, NH(n-$C_4H_9$), or N($C_2H_5$)$_2$, R is H or $CH_3$, and $R_1$ is $CH_3$ or $C_2H_5$. The reference lists eight therapeutic areas where inhibitors of cAMP phosphodiesterase could have utility: asthma, diabetes mellitus, female fertility control, male infertility, psoriasis, thrombosis, anxiety, and hypertension.

WO95/35298 (Otsuka, 1995) discloses pyrazolopyrimidines and states that they are useful as analgesics. The compounds are represented by the formula
where Q is carbonyl or sulfonyl, n is 0 or 1, A is a single bond, alkylene or alkenylene, $R^1$ is H, alkyl, etc., $R^2$ is naphthyl, cycloalkyl, heteroaryl, substituted phenyl or phenoxy, $R^3$ is H, alkyl or phenyl, $R^4$ is H, alkyl, alkoxycarbonyl, phenylalkyl, optionally phenylthio-substituted phenyl, or halogen, $R^5$ and $R^6$ are H or alkyl.

EP 0 591 528 (Otsuka, 1991) discloses anti-inflammatory use of pyrazolopyrimidines represented by the formula
where $R_1$, $R_2$, $R_3$ and $R_4$ are H, carboxyl, alkoxycarbonyl, optionally substituted alkyl, cycloalkyl, or phenyl, $R_5$ is $SR_6$ or $NR_7R_8$, $R_6$ is pyridyl or optionally substituted phenyl, and $R_7$ and $R_8$ are H or optionally substituted phenyl.

Springer et al, J. Med. Chem., 1976, vol. 19, no. 2, 291–296 and Springer U.S. Pat. Nos. 4,021,556 and 3,920,652 disclose pyrazolopyrimidines of the formula
where R can be phenyl, substituted phenyl or pyridyl, and their use to treat gout, based on their ability to inhibit xanthine oxidase.

Joshi et al., J. Prakt. Chemie, 321, 2, 1979, 341–344, discloses compounds of the formula

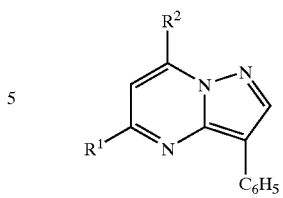

where $R^1$ is $CF_3$, $C_2F_5$, or $C_6H_4F$, and $R^2$ is $CH_3$, $C_2H_5$, $CF_3$, or $C_6H_4F$.

Maquestiau et al., Bull. Soc. Belg., vol. 101, no. 2, 1992, pages 131–136 discloses a pyrazolo[1,5-a]pyrimidine of the formula

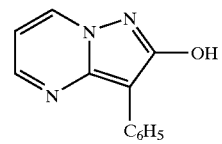

Ibrahim et al., Arch. Pharm. (weinheim) 320, 487–491 (1987) discloses pyrazolo[1,5-a]pyrimidines of the formula where R is NH2 or OH and Ar is 4-phenyl-3-cyano-2-aminopyrid-2-yl.

Other references which disclose azolopyrimidines inclued EP 0 511 528 (Otsuka, 1992), U.S. Pat. No. 4,997,940 (Dow, 1991), EP 0 374 448 (Nissan, 1990), U.S. Pat. No. 4,621,556 (ICN, 1997), EP 0 531 901 (Fujisawa, 1993), U.S. Pat. No. 4,567,263 (BASF, 1986), EP 0 662 477 (Isagro, 1995), DE 4 243 279 (Bayer, 1994), U.S. Pat. No. 5,397,774 (Upjohn, 1995), EP 0 521 622 (Upjohn, 1993), WO 94/109017 (Upjohn, 1994), J. Med. Chem., 24, 610–613 (1981), and J. Het. Chem., 22, 601 (1985) or others as additionally described herein.

SUMMARY OF THE INVENTION

In accordance with one aspect, the present invention provides novel compounds which bind to corticotropin releasing factor receptors, thereby altering the anxiogenic effects of CRF secretion. The compounds of the present invention are useful for the treatment of psychiatric disorders and neurological diseases, anxiety-related disorders, post-traumatic stress disorder, supranuclear palsy and feeding disorders as well as treatment of immunological, cardiovascular or heart-related diseases and colonic hypersensitivity associated with psychopathological disturbance and stress in mammals.

According to another aspect, the present invention provides novel compounds of formula (I) (described below) which are useful as antagonists of the corticotropin releasing factor. The compounds of the present invention exhibit activity as corticotropin releasing factor antagonists and appear to suppress CRF hypersecretion. The present invention also includes pharmaceutical compositions containing such compounds of formula (I), and methods of using such compounds for the suppression of CRF hypersecretion, and/or for the treatment of anxiogenic disorders.

According to yet another aspect, the present invention provides novel compounds, pharmaceutical compositions and methods which may be used in the treatment of affective disorder, anxiety, depression, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, inflammatory disorder, fertility problems, disorders, the treatment of which can be effected or facilitated by antagonizing CRF, including but not limited to disorders induced or facilitated by CRF, or a disorder selected from inflammatory disorders such as rheumatoid arthritis and osteoarthritis, pain, asthma, psoriasis and allergies; generalized anxiety disorder; panic, phobias, obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer, human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular and hear related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; osteoporosis; psychosocial dwarfism and hypoglycemia in mammals. The preferred uses include treatment of depression and anxiety.

The present invention also relates to the use of a compound of formula I and other compounds generically and specifically disclosed herein in therapy.

According to a still further aspect of the invention, the compounds provided by this invention (and especially labelled compounds of this invention) are also useful as standards and reagents in determining the ability of a potential pharmaceutical to bind to the CRF receptor.

DETAILED DESCRIPTION OF INVENTION

[1] Thus, in a first embodiment, the present invention provides a novel compound of formula I:

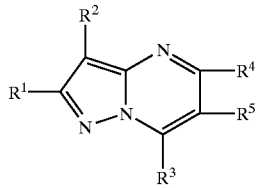

(I)

or a stereoisomer or pharmaceutically acceptable salt thereof, wherein:

$R^1$ is selected from the group consisting of
$C_{1-6}$ alkyl,
$C_{2-10}$ alkenyl,
$C_{2-10}$ alkynyl,
$C_{3-6}$ cycloalkyl,
$C_{1-6}$ alkyloxy,
$C_{1-5}$ alkylS(O)$_n$,
—$NR^{1a}R^{1B}$ wherein $R^{1a}$ and $R^{1b}$ are independently selected from H, $C_{1-4}$ alkyl, —C(O)$C_{1-4}$alkyl,
—C(O)$NR^{1a}R^{1b}$,
—O—C(O)$C_{1-4}$alkyl,
—$XR^{1c}$ wherein $R^{1c}$ is selected from H or —$C_{1-4}$ alkylaryl; X is selected from O or S(O)$_n$,
wherein $R^1$ is substituted with 0–6 substituents selected from halogen, $C_{1-4}$ alkyl, $C_{1-6}$ alkyloxy, $C_{1-4}$ haloalkyl, —$NR^{1a}R^{1b}$, —$XR^{1c}$;

$R^2$ is selected from the group consisting of
$C_{1-10}$ alkyl,
$C_{2-10}$ alkenyl,
$C_{2-10}$ alkynyl,
$C_{3-8}$ cycloalkyl,
$C_{3-6}$ cycloalkyl $C_{1-6}$ alkyl,
$C_{1-10}$ alkyloxy,
$C_{1-10}$ alkyloxy$C_{1-10}$ alkyl,
$C_{1-4}$ alkoxy $C_{1-4}$ alkyl,
—$SO_2$—$C_{1-10}$alkyl
—$SO_2R^{2a}$ wherein $R^{2a}$ is aryl,
—$SO_2R^{2b}$ wherein $R^{2b}$ is heteroaryl,
—$NR^{2c}R^{2D}$ wherein $R^{2c}$ and $R^{2d}$ are independently selected from H, $C_{1-8}$ alkyl, $S(O)_nC_{1-4}$ alkyl, $C(O)NR^{2c}R^{2d}$, $CO_2C_{1-4}$alkyl, $C_{3-8}$ cycloalkyl, $C_{1-6}$ alkyloxy$C_{1-6}$ alkyl, —C(O)$C_{1-4}$alkyl or $R^{2c}$ and $R^{2d}$ may join to form a heterocyclic ring having 0–3 heteroatoms selected from O, N or S,
-halogen,
—CN,
—C(O)L wherein L is selected from $NR^{2c}R^{2d}$, $C_{1-6}$ alkyl, H, —$OC_{1-6}$ alkyl, $O(CH_2)_mOC_{1-6}$alkyl, $O(CH_2)_mNR^{2c}R^{2d}$, OH,
aryl, heteroaryl or $C(O)OC_{1-6}$ alkyl, wherein m is 1–3,
or more particularly from,
—C(O)$NR^{2c}R^{2d}$,
—C(O)R wherein R is $C_{1-6}$ alkyl,
—C(O)$O_{1-4}$ alkyl,
—C(O)O(CH$_2$)$_2$OR wherein R is $C_{1-3}$ alkyl,
—C(O)O(CH$_2$)$_2$—NHR wherein R is $C_{1-3}$ alkyl,
—C(O)O(CH$_2$)$_2$—NR$^2$,
—C(O)OH,
—C(O)H,
—C(O)Ph,
—C(O)R' wherein R' is aryl, heteroaryl or carboalkoxy;
n is 0, 1 or 2;
$R^2$ is substituted with 0–3 substituents independently selected from R', R'', R''' wherein R', R'' and R''' are independently selected from $C_{1-6}$ alkyl, $C_{3-7}$ cycloalkyl, hydroxy$C_{1-6}$ alkyl, $C_{1-6}$ alkyloxy$C_{1-6}$ alkyl, $C_{2-6}$ alkenyl, $C_{1-6}$ alkyloxy, hydroxy, or
$R^2$ is substituted with 0–3 substituents independently selected from:
halogen,
—CN,
—$S(O)_nR^{2e}$ wherein $R^{2e}$ is selected from $C_{1-4}$ alkyl, $C_{1-4}$ haloalkyl, $C_{1-4}$ alkyloxy $C_{1-4}$ alkyl, $C_{3-6}$ cycloalkyl;
—$COR^{2f}$ wherein $R^{2f}$ is selected from H, $C_{1-4}$ alkyl, $C_{1-4}$ haloalkyl, $C_{1-4}$ alkyloxy $C_{1-4}$ alkyl, $C_{3-6}$ cycloalkyl, and $C_{3-6}$ cycloalkyl$C_{1-4}$ alkyl;
—$CO_2R^{2f}$, —NR$^{2g}$COR$^{2f}$ wherein R$^{2g}$ is selected from H, C$_{1-6}$ alkyl, C$_{3-7}$ c-alkyl, C$_{3-6}$ cycloalkyl C$_{1-6}$ alkyl;
—N(COR$^{2f}$)$_2$,
—NR$^{2g}$CONR$^{2f}$R$^{2h}$, wherein R$^{2h}$ is selected from H, C$_{1-6}$ alkyl, C$_{1-4}$ haloalkyl, C$_{1-4}$ alkoxy C$_{1-4}$ alkyl, C$_{3-6}$ cycloalkyl and C$_{3-6}$ cycloalkylC$_{1-6}$ alkyl;
—NR$^{2g}$CO$_2$R$^{2e}$,
—CONR$^{2g}$R$^{2h}$,
1-morpholinyl,
1-piperidinyl,
1-piperazinyl,
and
C$_{3-8}$ cycloalkyl wherein 0–1 carbon atoms in the C$_{4-8}$ cycloalkyl is replaced by a group selected from —O—, —S(O)$_n$—, —NR$^{2g}$, —NCO$_2$R$^{2e}$, —NCOR$^{2e}$, and —NSO$_2$R$^{2e}$; and wherein N$_4$ in 1-piperazinyl is substituted with 0–1 substituents selected from R$^{2g}$, CO$_2$R$^{2e}$, COR$^{2e}$ and SO$_2$R$^{2e}$; or the group R$^{2i}$, R$^{2j}$, R$^{2k}$, C$_{1-6}$ alkyl, C$_{2-8}$ alkenyl, C$_{2-8}$ alkynyl, Br, Cl, F, I, C$_{1-4}$ haloalkyl, —OR$^{2g}$, —NR$^{2g}$R$^{2h}$, —C$_{1-6}$ alkylOR$^{2g}$, and C$_{3-8}$ cycloalkyl which is substituted with 0–1 R$^{2l}$ and in wich 0–1 carbons of C$_{4-8}$ cycloalkyl is replaced by —O—, wherein R$^{2i}$ is selected from aryl wherein aryl includes phenyl, naphthyl, indanyl and indenyl, each R$^{2i}$ being substituted with 0–1 OR$^{2m}$ and 0–5 substituents independently selected from the group C$_{1-6}$ alkyl, C$_{3-6}$ cycloalkyl, Br, Cl, F, I, C$_{1-4}$ haloalkyl, —CN, nitro, —SH, —S(O)$_n$R$^{2n}$, —COR$^{2m}$, —OC(O)R$^{2n}$, —NR$^{2g}$COR$^{2m}$, —N(COR$^{2m}$)$_2$, —NR$^{2g}$CONR$^{2o}$R$^{2p}$, —NR$^{2g}$CO$_2$R$^{2n}$, —NR$^{2o}$R$^{2p}$ and —CONR$^{2o}$R$^{2p}$;

R$^{2j}$ is selected from heteroaryl wherein heteroaryl includes pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-s-oxide, 2,3-dihydro-benzothienyl-S-dioxide, indolinyl, benzoxazolin-2-onyl, benzodioxolanyl and benzodioxane, each heteroaryl being substituted on 0–4 carbon atoms with a substituent independently selected from the group C$_{1-6}$ alkyl, C$_{3-6}$ cycloalkyl, Br, Cl, F, I, C$_{1-4}$ haloalkyl, —CN, nitro, OR$^{2m}$, —SH, —S(O)$_n$R$^{2h}$, —COR$^{2m}$, —OC(O)R$^{2h}$, —NR$^{2g}$COR$^{2m}$, —N(COR$^{2m}$)$_2$, —NR$^{2g}$CONR$^{2o}$R$^{2p}$, NR$^{2g}$CO$_2$R$^{2h}$, —NR$^{2o}$R$^{2p}$ and —CONR$^{2o}$R$^{2p}$ and each heteroaryl being substituted on any nitrogen atom with 0–1 substituents selected from the group R$^{2g}$, CO$_2$R$^{2e}$, COR$^{2e}$ and SO$_2$R$^{2e}$;

R$^{2k}$ is heterocyclyl which is a saturated or partially saturated heteroaryl as defined for R$^{2j}$, each heterocyclyl being substituted on 0–4 carbon atoms with a substituent independently selected from the group C$_{1-6}$ alkyl, C$_{3-6}$ cycloalkyl, Br, Cl, F, I, C$_{1-4}$ haloalkyl, —CN, nitro, —OR$^{2m}$, —SH, —S(O)$_n$R$^{2h}$, —COR$^{2m}$, —OC(O)R$^{2h}$, —NR$^{2g}$COR$^{2m}$, —N(COR$^{2m}$)$_2$, —NR$^{2g}$CONR$^{2o}$R$^{2p}$, NR$^{2g}$COR$^{2h}$, —NR$^{2o}$R$^{2p}$ and —CONR$^{2o}$R$^{2p}$ and each heterocyclyl being substituted on any nitrogen atom with 0–1 substituents selected from the group R$^{2f}$, CO$_2$R$^{2e}$, COR$^{2e}$ and SO$_2$R$^{2e}$;

wherein

R$^{2l}$ is H, C$_{1-4}$ alkyl, C$_{3-6}$ cycloalky-C$_{1-4}$ alkyl and C$_{3-8}$ cycloalkyl;

R$^{2m}$ is H, C$_{1-6}$ alkyl, C$_{3-6}$ cycloalkyl C$_{1-6}$ alkyl, C$_{1-2}$ alkyloxy C$_{1-2}$ alkyl, C$_{1-4}$ haloalkyl, R$^{2q}$S(O)$_n$—C$_{1-4}$ alkyl and R$^{2r}$R$^{2s}$N—C$_{2-4}$ alkyl;

R$^{2n}$ is H, C$_{1-6}$ alkyl, C$_{3-10}$ cycloalkyl, C$_{3-6}$ cycloalkyl-C$_{1-6}$ alkyl, C$_{1-2}$ alkyloxy C$_{1-2}$ alkyl, and C$_{1-4}$ haloalkyl;

R$^{2o}$ and R$^{2p}$ are independently selected at each occurrence from H, C$_{1-6}$ alkyl, C$_{3-10}$ cycloalkyl, C$_{3-6}$ cycloalkyl C$_{1-6}$ alkyl and C$_{1-4}$ haloalkyl;

R$^{2q}$ is selected from C$_{1-6}$ alkyl, C$_{1-4}$ haloalkyl, C$_{1-4}$ alkoxy-C$_{1-4}$ alkyl, C$_{3-6}$ cycloalkyl, C$_{3-6}$ cycloalkyl-C$_{1-6}$ alkyl, aryl, aryl(C$_{1-4}$ alkyl), heteroaryl and heleroaryl (C$_{1-4}$ alkyl)- and benzyl, each benzyl being substituted on the aryl moiety with 0–1 substituents selected from the group C$_{1-4}$ alkyl, Br, Cl, F, I, C$_{1-4}$ haloalkyl, nitro, C$_{1-4}$ alkoxy C$_{1-4}$ haloalkoxy, and dimethylamino;

R$^{2r}$R$^{2s}$ taken together with the N form 1-pyrrolidinyl, 1-morpholinyl, 1-piperidinyl or 1-piperazinyl wherein N$_4$ in 1-piperiazinyl is substituted with 0–1 substituents selected from the group R$^{2t}$, CO$_2$R$^{2q}$, COR$^{2q}$ and SO$_2$R$^{2q}$;

R$^{2t}$ is selected from H, C$_{1-4}$ alkyl, C$_{1-4}$ haloalkyl, C$_{1-4}$ alkoxy-C$_{1-4}$ alkyl, C$_{3-6}$ cycloalkyl, C$_{3-6}$ cycloalkyl-C$_{1-6}$ alkyl, aryl, aryl (C$_{1-4}$ alkyl)-, heteroaryl and heteroaryl (C$_{1-4}$ alkyl);

R$^3$ is selected from an aryl or heteroaryl group attached through an unsaturated carbon atom;

aryl is selected from phenyl, naphthyl, indanyl and indenyl, each aryl being substituted with 0–5 substituents independently selected at each occurrence from C$_{1-6}$ alkyl, C$_{3-6}$ cycloalkyl, methylenedioxy, C$_{1-4}$ alkyloxy-C$_{1-4}$ alkyloxy, —OR$^{2m}$, Br, Cl, F, I, C$_{1-4}$ haloalkyl, —CN, —NO$_2$, —SH, —S(O)$_n$R$^{2n}$, —COR$^{2m}$, —CO$_2$R$^{2m}$, —OC(O)R$^{2n}$, —NR$^{2g}$COR$^{2m}$, —N(COR$^{2m}$)$_2$, —NR$^{2g}$CONR$^{2o}$R$^{2p}$, —NR$^{2g}$CO$_2$R$^{2h}$, —NR$^{2o}$R$^{2p}$ and CONR$^{2o}$R$^{2p}$ and up to 1 phenyl, each phenyl substituent being substituted with 0–4 substituents selected from the group C$_{1-3}$ alkyl, C$_{1-3}$ alkoxy, Br, Cl, F, I, —CN, dimethylamino, CF$_3$, C$_2$F$_5$, OCF$_3$, SO$_2$Me and acetyl;

heteroaryl is selected from the group pyridyl, pyrimidyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzo-furanyl, 2,3-dihydrobenzothienyl, 2,3-dihydro-benzothienyl-S-oxide, 2,3-dihydrobenzothienyl-s-dioxide, indolinyl, benzoxazolin-2-on-yl, benzodioxolanyl and benzodioxane, each heteroaryl being substitued at 0–4 carbon atoms with a substituent independently selected at each occurrence from the group C$_{1-6}$ alkyl, C$_{3-6}$ cycloalkyl, Br, F, I, C$_{1-4}$ haloalkyl, —CN, NR$^{2g}$R$^{2h}$, nitro, —OR$^{2m}$, —SH, —S(O)$_n$R$^{2n}$, COR$^{2m}$, —CO$_2$R$^{2m}$, —OC(O)R$^{2n}$, —NR$^{2g}$COR$^{2m}$, —N(COR$^{2m}$)$_2$, —NR$^{2g}$CONR$^{2o}$R$^{2p}$ and each heteroaryl being substituted at any nitrogen atom with 0–1 substituents selected from the group R$^{2g}$, CO$_2$R$^{3a}$, COR$^{3a}$ and SO$_2$R$^{3a}$ wherein, R$^3$a is selected from the group C$_{1-6}$ alkyl, C$_{1-4}$ cycloalkyl-C$_{1-6}$ alkyl and benzyl, each benzyl being substituted on the aryl moiety with 0–1 substituents selected from the group C$_{1-4}$ alkyl, Br, Cl, F, I, C$_{1-4}$ haloalkyl, nitro, C$_{1-4}$ alkoxy, C$_{1-4}$ haloalkoxy, and dimethylamino;

R$^4$ and R$^5$ are independently selected at each occurrence from H, Br, Cl, F, I, —CN, C$_{1-6}$ alkyl, C$_{2-6}$ alkenyl, C$_{2-6}$ alkynyl, C$_{3-8}$ cycloalkyl, C$_{1-6}$ alkyloxy, C$_{1-6}$ alkylthio, C$_{1-6}$ alkylsulfinyl, C$_{1-6}$ alkylsulfonyl, amino, C$_{1-4}$ alkylamino, (C$_{1-4}$ alkyl)$_2$ amino and phenyl, each phenyl is substituted with 0–3 groups selected from the group consisting of C$_{1-7}$ alkyl, C$_{3-8}$ cycloalkyl, Br, Cl, F, I, —C(O)H, C$_{1-4}$ haloalkyl, nitro, C$_{1-4}$ alkoxy, C$_{1-4}$ haloalkoxy, C$_{1-4}$ alkylthio, C$_{1-4}$ alkylsulfinyl, C$_{1-4}$ alkylsulfonyl, C$_{1-6}$ alkylamino and (C$_{1-4}$ alkyl)$_2$ amino and wherein R$^4$ and R$^5$ non-phenyl groups may be substituted with 0–5 substituents selected from OH, halogen, —C(O)H, —OC$_{1-6}$-alkyl and C$_{1-6}$ haloalkyl, C$_{1-6}$ alkyl, C$_{3-7}$ c-alkyl, C$_{1-6}$ alkyl(OH)$_n$CO$_2$R wherein R is H or C$_{1-6}$ alkyl, C$_{1-6}$ alkyl(OH)$_n$, wherein n is 0–3 or R$^4$ and R$^5$ may join together to form a C$_{3-6}$ alkylene chain; with the proviso that the compounds of Formula I with R$^1$, R$^2$, R$^3$, R$^4$ and R$^5$ as specifically defined below are excluded:

(a) a compound of formula I wherein R$^1$ is unsubstituted, unbranched (linear) C$_{1-3}$ alkyl and R$^2$ is —C(O)-Ph (EP 0 129 847 A2, U.S. Pat. No. 4,521,422, U.S. Pat. No. 4,654,347);

(b) a compound of formula I, wherein R$^5$ is H or C$_{1-3}$ alkyl and R$^3$ is pyridyl, pyridyl-N-oxide, thien-3-yl or furan-3-yl or C$_{1-3}$ alkyl substituted versions thereof and R$^1$ is carboamoyl or unsubstituted, unbranched C$_{1-3}$ alkyl, R$^2$ is F, Cl, Br, formyl, carboxyl, CN, hydroxymethyl, unsubstituted, unbranched C$_{1-3}$ alkyl, —C(O)R, —C(O)OR, —CH$_2$OR, —C(O)O(CH$_2$)$_2$OR, —C(O)O(CH$_2$)$_2$NHR, or —C(O)O(CH$_2$)$_2$NR$^2$ wherein R is C$_{1-3}$ alkyl (U.S. Pat. No. 4,281,000);

(c) a compound of formula I, wherein R$^1$ is unsubstituted, unbranched C$_{1-3}$ alkyl and R$^2$ is halogen, CN or —C(O)R wherein R is H, C$_{1-3}$ alkyl or C$_{1-4}$ alkoxy, R$^3$ is Ph substituted with NR$^{2g}$C(O)R$^{2m}$ (U.S. Pat. No. 4,626,538)

(d) a compound of formula I, R$^2$ is CN, halogen, CO$_2$R with R equal to C$_{1-3}$ alkyl, unsubstituted, unbranched C$_{1-3}$ alkyl, C$_{1-3}$ haloalkyl or CONH$_2$ and R$^1$ is equal to OR, SR wherein R is C$_{1-3}$ alkyl, C$_{1-4}$ haloalkyl or C$_{3-4}$ halocycloalkyl, and R$^3$ is phenyl or substituted phenyl (U.S. Pat. No. 5,127,936);

(e) a compound of formula I, wherein R$^5$ is H or C$_{1-3}$ alkyl; R$^3$ is phenyl, ortho-trifluoromethylphenyl, meta-trifluorophenyl or meta-methoxyphenyl; R$^1$ is carbamoyl or unsubstituted C$_{1-3}$ alkyl; R$^2$ is halogen, formyl, carboxyl, cyano, hydroxymethyl, unsubstituted, unbranched C$_{1-3}$ alkyl, —C(O)R, —C(O)OR, CH$_2$OR, —C(O)O(CH$_2$)$_2$OR, —C(O)O(CH$_2$)$_2$NHR or —C(O)O(CH$_2$)$_2$NR$^2$ wherein R is C$_{1-3}$ alkyl (U.S. Pat. No. 4,178,449);

(f) no entry (g) in a compound of formula I, R$^2$ is CN, R$^1$ is methyl, R$^4$ and R$^5$ are H, R$^3$ is phenyl substituted with imidazo (or 2-methylimidazo) through the imidazo nitrogen atom (Registry Reference 20, 21);

(h) in a compound of formula I, R$^2$ is CN, R$^1$ is SCH$_3$, R$^3$ is para-chlorophenyl, R$^4$ is SCH$_3$ and R$^5$ is H (registry reference 25);

(i) in a compound of formula I, R$^2$ is CN, R$^1$ is SCH$_3$, R$^3$ is pyrid-4-yl, R$^4$ is SCH$_3$ and R$^5$ is H (Registry Reference 26);

(j) in a compound of formula I, R$^2$ is CN, R$^1$ is SCH$_3$, R$^3$ is Ph, R$^4$ is SCH$_3$ and R$^5$ is H (Registry Reference 27);

(k) in a compound of formula I, R$^2$ is C(O)NH$_2$, R is SCH$_3$, R$^3$ is pyrid-3-yl, R$^4$ is SCH$_3$ and R$^5$ is H (Registry Reference 28);

(l) in a compound of formula I, R$^2$ is C(O)NH$_2$, R$^1$ is SCH$_3$, R$^3$ is Ph, R$^4$ is SCH$_3$ (or Ph) and R$^5$ is H (Registry Reference 29, 31);

(m) in a compound of formula I, R$^2$ is C(O)OEt, R$^1$ is SCH$_3$, R$^3$ is Ph, R$^4$ is SCH$_3$ (or Ph) and R$^5$ is H (registry reference 30, 32);

(n) in a compound of formula I, R$^1$ is N(C(O)CH$_3$)$_2$, R$^2$ is CH$_2$Ph(p-Me, p-Cl), R$^3$ is Ph (p-ClPh), R$^4$ is SCH$_3$ and R$^5$ is H (Registry Reference 33, 34);

(o) in a compound of formula I, R$^1$ is N(C(O)CH$_3$)$_2$, R$^2$ is CH$_2$Ph(p-OMe), R$^3$ is p-ClPh, R$^4$ is SCH$_3$ and R$^5$ is H (registry ref. 35);

(p) in a compound of formula I, R$^2$ is CN, R$^1$ is CH$_3$, R$^3$ is Ph, R$^4$ is H and R$^5$ is H (registry ref. 44);

(q) in a compound of formula I, R$^2$ is C(O)NH$_2$, R$^1$ is CH$_3$, R$^3$ is Ph, R$^4$ is CH$_3$ and R$^5$ is H (reg. ref. 45);

(s) in a compound of formula I, R$^2$ is C(O)NH$_2$, R$^1$ is CH$_3$, R$^3$ is pyrid-4-yl, R$^4$ and R$^5$ are H (reg. ref. 46);

(t) in a compound of formula I, R$^2$ is C(O)NH$_2$, R$^1$ is CH$_3$, R$^3$ is m-CF$_3$Ph, R$^4$ and R$^5$ are H (reg. ref. 47);

(u) in a compound of formula I, R$^2$ is CN, R$^1$ is CH$_3$, R$^3$ is Ph, R$^4$ is CH$_3$ and R$^5$ is H (reg. ref. 48);

(v) in a compound of formula I, R$^2$ is CN, R$^1$ is CH$_3$, R$^3$ is pyrid-4-yl, R$^4$ and R$^5$ are H (reg. ref. 49);

(w) no entry (x) in a compound of formula I, R$^2$ is CH$_3$, R$^1$ is CH$_3$, R$^3$ is p-F-Ph, R$^4$ is c-propyl and R$^5$ is CH=CH—CH(OH)CH$_2$CH(OH)CH$_2$C(O)O-iPr (reg. ref. 75);

(y) in a compound of formula I, R$^2$ is CH$_3$, R$^1$ is CH$_3$, R$^3$ is p-F-Ph, R$^4$ is c-propyl and R$^5$ is CH=CH—CH(OH)CH$_2$CH(OH)CH$_2$C(O)O-nPr (reg. ref. 76);

(z) in a compound of formula I, R$^2$ is CH$_3$, R$^1$ is CH$_3$, R$^3$ is p-F-Ph, R$^4$ is c-propyl and R$^5$ is CH=CH—CH(OH)CH$_2$CH(OH)CH$_2$C(O)OMe (reg. ref. 77);

(aa) in a compound of formula I, R$^2$ is CH$_3$, R$^1$ is CH$_3$, R$^3$ is p-F-Ph, R$^4$ is c-propyl and R$^5$ is CH=CH—CH(OH)CH$_2$CH(OH)CH$_2$C(O)OH (reg. ref. 78);

(bb) in a compound of formula I, R$^2$ is CH$_3$, R$^1$ is CH$_3$, R$^3$ is p-F-Ph, R$^4$ is c-propyl and R$^5$ is —CH$_2$OH (reg. ref. 100);

(cc) in a compound of formula I, R$^2$ is CH$_3$, R$^1$ is CH$_3$, R$^3$ is p-F-Ph, R$^4$ is c-propyl and R$^5$ is —C(O)H (reg. ref. 105);

(dd) in a compound of formula I, R$^2$ is CH$_3$, R$^1$ is CH$_3$, R$^3$ is p-F-Ph, R$^4$ is c-propyl and R$^5$ is —CH=CH—C(O)H (reg. ref. 110);

(ee) in a compound of formula I, R$^2$ is CH$_3$, R$^1$ is CH$_3$, R$^3$ is p-F-Ph, R$^4$ is c-propyl and R$^5$ is CH=CH—CH(OH)CH$_2$CH(OH)CH$_2$C(O)OEt (reg. ref. 115);

(ff) in a compound of formula I, R$^2$ is CH$_3$, R$^1$ is CH$_3$, R$^3$ is p-F-Ph, R$^4$ is c-propyl and R$^5$ is CH=CH—CH(OH)CH$_2$CH(OH)CH$_2$C(O)O$^-$Na$^+$ (reg. ref. 120);

(gg) in a compound of formula I, R$^2$ is CN, R$^1$ is CF$_3$, R$^3$ is m-Cl-Ph, R$^4$ is CH$_3$ and R$^5$ is H (reg. ref. 130); (hh) in a compound of formula I, R$^2$ is CN, R$^1$ is CF$_3$, R$^3$ is m-CF$_3$-Ph, R$^4$ is CH$_3$ and R$^5$ is H (reg. ref. 132);

(ii) in a compound of formula I, R$^2$ is CN, R$^1$ is CF$_3$, R$^3$ is Ph, R$^4$ is CH$_3$ and R$^5$ is H (reg. ref. 133);

(jj)–(mm) no entry (nn) in a compound of formula I, R$^2$ is —C(O)NH$_2$, R$^1$ is Me, R$^3$ is Ph, R$^4$ is H and R$^5$ is Me (reg. ref. 140);

(oo) in a compound of formula I, R$^2$ is CN, R$^1$ is Me, R$^3$ is Ph, R$^4$ is H and R$^5$ is Me (reg. ref. 141);

(pp) in a compound of formula I, R$^2$ is CN, R$^1$ is Me, R$^3$ is o-Cl,m-Cl-Ph, R$^4$ is H and R$^5$ is H (reg. ref. 144);

(qq) in a compound of formula I, R$^2$ is C(O)NH$_2$, R$^1$ is CH$_3$, R$^3$ is Ph, R$^4$ and R$^5$ are H (reg. ref. 145);

(rr) in a compound of formula I, R$^2$ is C(O)NH$_2$, R$^1$ is CH$_3$, R$^3$ is O-CL,m-Cl-Ph, R$^4$ and R$^5$ are H (reg. ref. 146);

(ss) in a compound of formula I, R$^2$ is C(O)OMe, R$^1$ is —SCH$_2$-Ph, R$^3$ is Ph, R$^4$ is Me and R$^5$ is H (reg. ref. 147);

(tt) in a compound of formula I, R$^2$ is C(O)OMe, R$^1$ is —SCH$_2$-Ph, R$^3$ is Ph, R$^4$ is H and R$^5$ is H (reg. ref. 148);

(uu) in a compound of formula I, R$^2$ is C(O)Ph, R$^1$ is Me, R$^3$ is pyrid-4-yl, R$^4$ and R$^5$ are H (reg. ref. 154);

(vv) in a compound of formula I, R$^2$ is C(O)Ph, R$^1$ is Me, R$^3$ is m-CF$_3$-Ph, R$^4$ and R$^5$ are H (reg. ref. 155);

(ww) in a compound of formula I, R$^2$ is C(O)Ph, R$^1$ is Me, R$^3$ is pyrid-3-yl, R$^4$ and R$^5$ are H (reg. ref. 156);

(xx) in a compound of formula I, R$^2$ is CN, R$^1$ is SCH$_3$, R$^3$ is Ph, R$^4$ is Ph and R$^5$ is H (reg. ref. 157);

(yy) in a compound of formula I, $R^2$ is CN, $R^1$ is $SCH_3$, $R^3$ is Ph, $R^4$ is Ph and $R^5$ is H (reg. ref. 157);
(zz) in a compound of formula I, $R^2$ is Cl, $R^1$ is Et, $R^3$ is pyrid-3-yl, $R^4$ and $R^5$ are H (reg. ref. 163);
(aaa) in a compound of formula I, $R^2$ is $CO_2H$, $R^1$ is Et, $R^3$ is pyrid-3-yl, $R^4$ and $R^5$ are H (reg. ref. 164);
(bbb) in a compound of formula I, $R^2$ is $CO_2H$, $R^1$ is $CH_3$, $R^3$ is pyrid-3-yl, $R^4$ and $R^5$ are H and HCl salt (reg. ref. 165);
(ccc) in a compound of formula I, $R^2$ is C(O)OEt, $R^1$ is $CH_3$, $R^3$ is pyrid-3-yl, $R^4$ and $R^5$ are H (reg. ref. 166);
(ddd) in a compound of formula I, $R^2$ is CN, $R^1$ is $CH_3$, $R^3$ is pyrid-3-yl, $R^4$ is H and $R^5$ is $CH_3$ (reg. ref. 167);
(eee) in a compound of formula I, $R^2$ is CN, $R^1$ is $CH_3$, $R^3$ is pyrid-3-yl, $R^4$ and $R^5$ are H (reg. ref. 168);
(fff) in a compound of formula I, $R^2$ is C(O)OEt, $R^1$ is Et, $R^3$ is pyrid-3-yl, $R^4$ and $R^5$ are H (reg. ref. 169);
(ggg) in a compound of formula I, $R^2$ is CN, $R^1$ is Et, $R^3$ is pyrid-3-yl, $R^4$ and $R^5$ are H (reg. ref. 170);
(hhh) in a compound of formula I, $R^2$ is CN, $R^1$ is $CH_3$, $R^3$ is m-$CF_3$Ph, $R^4$ and $R^5$ are H (reg. ref. 172);
(iii) in a compound of formula I, $R^2$ is CN, $R^1$ is $CH_2CN$, $R^3$ is m-$CF_3$-Ph, $R^4$ and $R^5$ are H (reg. ref. 173);
(jjj) in a compound of formula I, $R^2$ is C(O)OMe, $R^1$ is Me, $R^3$ is m-$CF_3$-Ph, $R^4$ and $R^5$ are H (reg. ref. 174);
(kkk) in a compound of formula I, $R^2$ is CN, $R^1$ is Et, $R^3$ is m-OMe-Ph, $R^4$ and $R^5$ are H (reg. ref. 175);
(lll) in a compound of formula I, $R^2$ is O(O)OEt, $R^1$ is Et, $R^3$ is Ph, $R^4$ and $R^5$ are H (reg. ref. 176);
(mmm) in a compound of formula I, $R^2$ is O(O)OEt, $R^1$ is Et, $R^3$ is m-$CF_3$Ph, $R^4$ and $R^5$ are H (reg. ref. 177);
(nnn) in a compound of formula I, $R^2$ is CN, $R^1$ is Et, $R^3$ is m-$CF_3$-Ph, $R^4$ is H and $R^5$ is $CH_3$ (reg. ref. 178);
(ooo) in a compound of formula I, $R^2$ is CN, $R^1$ is Et, $R^3$ is m-$CF_3$, $R^4$ and $R^5$ are H (reg. ref. 179);
(ppp) in a compound of formula I, $R^2$ is CN, $R^1$ is $C(O)NH_2$, $R^3$ is m-$CF_3$-Ph, $R^4$ and $R^5$ are H (reg. ref. 180);
(qqq) in a compound of formula I, $R^2$ is CN, $R^1$ is Et, $R^3$ is Ph, $R^4$ and $R^5$ are H (reg. ref. 181).

[1'] In a preferred embodiment, the present invention provides a novel compound of formula I:

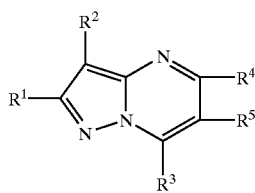

(I)

or a stereoisomer or pharmaceutically acceptable salt thereof, wherein:
$R^1$ is selected from the group consisting of
$C_{1-6}$ alkyl,
$C_{2-10}$ alkenyl,
$C_{2-10}$ alkynyl,
$C_{3-6}$ cycloalkyl,
$C_{1-6}$ alkyloxy,
$C_{1-6}$ alkylS(O)$_n$,
—$NR^{1a}R^{1B}$ wherein $R^{1a}$ and $R^{1b}$ are independently selected from H, $C_{1-4}$ alkyl, —C(O)$C_{1-4}$alkyl,
—C(O)$NR^{1a}R^{1b}$,
—O—C(O)$C_{1-4}$alkyl,
—$XR^{1c}$ wherein $R^{1c}$ is selected from H or —$C_{1-4}$ alkylaryl;
X is selected from O or S(O)$_n$;
wherein $R^1$ is substituted with 0–6 substituents selected from halogen, $C_{1-4}$ alkyl, $C_{1-6}$ alkyloxy, $C_{1-6}$ haloalkyl, —$NR^{1a}R^{1b}$, —$XR^{1c}$;

$R^2$ is selected from the group consisting of
$C_{1-10}$ alkyl excluding unsubstituted, unbranched $C_{1-3}$alkyl,
$C_{2-10}$ alkenyl,
$C_{2-10}$ alkynyl,
$C_{3-8}$ cycloalkyl,
$C_{3-6}$ cycloalkyl $C_{1-6}$ alkyl,
$C_{1-10}$ alkyloxy,
$C_{1-10}$ alkyloxy$C_{1-10}$ alkyl,
$C_{1-4}$ alkoxy $C_{1-4}$ alkyl,
—$SO_2$—$C_{1-10}$ alkyl
—$SO_2R^{2a}$ wherein $R^{2a}$ is aryl,
—$SO_2R^{2b}$ wherein $R^{2b}$ is heteroaryl,
—$NR^{2C}R^{2D}$ wherein $R^{2c}$ and $R^{2d}$ are independently selected from H, $C_{1-8}$ alkyl, S(O)$_n$$C_{1-4}$ alkyl, $C(O)NR^{2c}R^{2d}$, $CO_2C_{1-4}$alkyl, $C_{3-8}$ cycloalkyl, $C_{1-6}$ alkyloxy$C_{1-6}$ alkyl, —C(O)$C_{1-4}$alkyl or $R^{2c}$ and $R^{2d}$ may join to form a heterocyclic ring having 0–3 heteroatoms selected from O, N or S,
n is 0, 1 or 2;
$R^2$ is substituted with 0–3 substituents independently selected from R', R", R''' wherein R', R" and R''' are independently selected from $C_{1-6}$ alkyl, $C_{3-7}$ cycloalkyl, hydroxy$C_{1-6}$ alkyl, $C_{1-6}$ alkyloxy$C_{1-6}$ alkyl, $C_{2-6}$ alkenyl, $C_{1-6}$ alkyloxy, hydroxy, or
$R^2$ is substituted with 0–3 substituents independently selected from:
—CN,
—S(O)$_n$$R^{2e}$ wherein $R^{2e}$ is selected from $C_{1-4}$ alkyl, $C_{1-4}$ haloalkyl, $C_{1-4}$ alkyloxy $C_{1-4}$ alkyl, $C_{3-6}$ cycloalkyl;
—COR$^{2f}$ wherein $R^{2f}$ is selected from H, $C_{1-4}$ alkyl, $C_{1-4}$ haloalkyl, $C_{1-4}$ alkyloxy $C_{1-4}$ alkyl, $C_{3-6}$ cycloalkyl, and $C_{3-6}$ cycloalkyl$C_{1-4}$ alkyl;
—$CO_2R^{2f}$,
—$NR^{2g}COR^{2f}$ wherein $R^{2g}$ is selected from H, $C_{1-6}$ alkyl, $C_{3-7}$ c-alkyl, $C_{3-6}$ cycloalkyl $C_{1-6}$ alkyl;
—$N(COR^{2f})_2$,
—$NR^{2g}CONR^{2f}R^{2h}$, wherein $R^{2h}$ is selected from H, $C_{1-6}$ alkyl, $C_{1-4}$ haloalkyl, $C_{1-4}$ alkoxy $C_{1-4}$ alkyl, $C_{3-6}$ cycloalkyl and $C_{3-6}$ cycloalkyl$C_{1-6}$ alkyl;
—$NR^{2g}CO_2R^{2e}$,
—$CONR^{2g}R^{2h}$,
1-morpholinyl,
1-piperidinyl,
1-piperazinyl,
and
$C_{3-8}$ cycloalkyl wherein 0–1 carbon atoms in the $C_{4-8}$ cycloalkyl is replaced by a group selected from —O—, —S(O)$_n$—, $NR^{2g}$—, —$NCO_2R^{2e}$, —$NCOR^{2e}$, and —$NSO_2R^{2e}$; and wherein $N_4$ in 1-piperazinyl is substituted with 0–1 substituents selected from $R^{2g}$, $CO_2R^{2e}$, $COR^{2e}$ and $SO_2R^{2e}$; or
the group $R^{2j}$, $R^{2k}$, $C_{1-6}$ alkyl, $C_{2-8}$ alkenyl, $C_{2-8}$ alkynyl, Br, Cl, F, I, $C_{1-4}$ haloalkyl, —$OR^{2g}$, —$NR^{2g}R^{2h}$, —$C_{1-6}$ alkylOR$^{2g}$, and $C_{3-8}$ cycloalkyl which is substituted with 0–1 $R^{2l}$ and in wich 0–1 carbons of $C_{4-8}$ cycloalkyl is replaced by —O—, wherein
$R^{2j}$ is selected from heteroaryl wherein heteroaryl includes pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-s-oxide, 2,3-dihydro-benzothienyl-S-dioxide, indolinyl, benzoxazolin-2-onyl, benzodioxolanyl and benzodioxane, each heteroaryl being substituted on 0–4 carbon atoms with a substituent independently selected from the group $C_{1-6}$ alkyl, $C_{3-6}$ cycloalkyl, Br, Cl, F, I, $C_{1-4}$ haloalkyl, —CN, nitro, $OR^{2m}$, —SH, —S(O)$_n$R$^{2h}$, —COR$^{2m}$, —OC(O)R$^{2h}$, —NR$^{2g}$COR$^{2m}$, —N(COR$^{2m}$)$_2$, —NR$^{2g}$CONR$^{2o}$R$^{2p}$, —NR$^{2g}$CO$_2$R$^{2h}$, —NR$^{2o}$R$^{2p}$ and —CONR$^{2o}$R$^{2p}$ and each heteroaryl being substituted on any nitrogen atom with 0–1 substituents selected from the group R$^{2g}$, CO$_2$R$^{2e}$, COR$^{2e}$ and SO$_2$R$^{2e}$;

R$^{2k}$ is heterocyclyl which is a saturated or partially saturated heteroaryl as defined for R$^{2j}$, each heterocyclyl being substituted on 0–4 carbon atoms with a substituent independently selected from the group $C_{1-6}$ alkyl, $C_{3-6}$ cycloalkyl, Br, Cl, F, I, $C_{1-4}$ haloalkyl, —CN, nitro, —OR$^{2m}$, —SH, —S(O)$_n$R$^{2h}$, —COR$^{2m}$, —OC(O)R$^{2h}$, —NR$^{2g}$COR$^{2m}$, —N(COR$^{2m}$)$_2$, —NR$^{2g}$CONR$^{2o}$R$^{2p}$, NR$^{2g}$CO$_2$R$^{2h}$, —NR$^{2o}$R$^{2p}$ and —CONR$^{2o}$R$^{2p}$ and each heterocyclyl being substituted on any nitrogen atom with 0–1 substituents selected from the group R$^{2f}$, CO$_2$R$^{2e}$, COR$^{2e}$ and SO$_2$R$^{2e}$;

wherein

R$^{2l}$ is H, $C_{1-4}$ alkyl, $C_{3-6}$ cycloalky-$C_{1-4}$ alkyl and $C_{3-8}$ cycloalkyl;

R$^{2m}$ is H, $C_{1-6}$ alkyl, $C_{3-6}$ cycloalkyl $C_{1-6}$ alkyl, $C_{1-2}$ alkyloxy $C_{1-2}$ alkyl, $C_{1-4}$ haloalkyl, R$^{2q}$S(O)$_n$—$C_{1-4}$ alkyl and R$^{2r}$R$^{2s}$N—$C_{2-4}$ alkyl;

R$^{2n}$ is H, $C_{1-6}$ alkyl, $C_{3-10}$ cylalkyl, $C_{3-6}$ cycloalkyl-$C_{1-6}$ alkyl, $C_{1-2}$ alkyloxy $C_{1-2}$ alkyl, and $C_{1-4}$ haloalkyl;

R$^{2o}$ and R$^{2p}$ are independently selected at each occurrence from H, $C_{1-6}$ alkyl, $C_{3-10}$ cycloalkyl, $C_{3-6}$ cycloalkyl $C_{1-6}$ alkyl and $C_{1-4}$ haloalkyl;

R$^{2q}$ is selected from $C_{1-6}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl), heteroaryl and heleroaryl ($C_{1-4}$ alkyl)- and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy $C_{1-4}$ haloalkoxy, and dimethylamino;

R$^{2r}$R$^{2s}$ taken together with the N form 1-pyrrolidinyl, 1-morpholinyl, 1-piperidinyl or 1-piperazinyl wherein N$_4$ in 1-piperiazinyl is substituted with 0–1 substituents selected from the group R$^{2t}$, CO$_2$R$^{2q}$, COR$^{2q}$ and SO$_2$R$^{2q}$;

R$^{2t}$ is selected from H, $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl ($C_{1-4}$ alkyl)-, heteroaryl and heteroaryl ($C_{1-4}$ alkyl);

R$^3$ is selected from an aryl or heteroaryl group attached through an unsaturated carbon atom;

aryl is selected from phenyl, naphthyl, indanyl and indenyl, each aryl being substituted with 0–5 substituents independently selected at each occurrence from $C_{1-6}$ alkyl, $C_{3-6}$ cycloalkyl, methylenedioxy, $C_{1-4}$ alkyloxy-$C_{1-4}$ alkyloxy, —OR$^{2m}$, Br, Cl, F, I, $C_{1-4}$ haloalkyl, —CN, —NO$_2$, —SH, —S(O)$_n$R$^{2n}$, —COR$^{2m}$, —CO$_2$R$^{2m}$, —OC(O)R$^{2n}$, —NR$^{2g}$COR$^{2m}$, —N(COR$^{2m}$)$_2$, —NR$^{2g}$CONR$^{2o}$R$^{2p}$, —NR$^{2g}$CO$_2$R$^{2h}$, —NR$^{2o}$R$^{2p}$ and CONR$^{2o}$R$^{2p}$ and up to 1 phenyl, each phenyl substituent being substituted with 0–4 substituents selected from the group $C_{1-3}$ alkyl, $C_{1-3}$ alkoxy, Br, Cl, F, I, —CN, dimethylamino, CF$_3$, C$_2$F$_5$, OCF$_3$, SO$_2$Me and acetyl;

heteroaryl is selected from the group pyridyl, pyrimidyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzo-furanyl, 2,3-dihydrobenzothienyl, 2,3-dihydro-benzothienyl-S-oxide, 2,3-dihydrobenzothienyl-s-dioxide, indolinyl, benzoxazolin-2-on-yl, benzodioxolanyl and benzodioxane, each heteroaryl being substitued at 0–4 carbon atoms with a substituent independently selected at each occurrence from the group $C_{1-6}$ alkyl, $C_{3-6}$ cycloalkyl, Br, F, I, $C_{1-4}$ haloalkyl, —CN, NR$^{2g}$R$^{2h}$, nitro, —OR$^{2m}$, —SH, —S(O)$_n$R$^{2n}$, COR$^{2m}$, —CO$_2$R$^{2m}$, —OC(O)R$^{2n}$, —NR$^{2g}$COR$^{2m}$, —N(COR$^{2m}$)$_2$, —NR$^{2g}$CONR$^{2o}$R$^{2p}$ and each heteroaryl being substituted at any nitrogen atom with 0–1 substituents selected from the group, R$^{2g}$, CO$_2$R$^{3a}$, COR$^{3a}$ and SO$_2$R$^{3a}$ wherein, R$^{3a}$ is selected from the group $C_{1-6}$ alkyl, $C_{1-4}$ cycloalkyl-$C_{1-6}$ alkyl and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

R$^4$ and R$^5$ are independently selected at each occurrence from H, Br, Cl, F, I, —CN, $C_{1-6}$ alkyl, $C_{2-6}$ alkenyl, $C_{2-6}$ alkynyl, $C_{3-8}$ cycloalkyl, $C_{1-6}$ alkyloxy, $C_{1-6}$ alkylthio, $C_{1-6}$ alkylsulfinyl, $C_{1-6}$ alkylsulfonyl, amino, $C_{1-4}$ alkylamino, ($C_{1-4}$ alkyl)$_2$ amino and phenyl, each phenyl is substituted with 0–3 groups selected from the group consisting of $C_{1-7}$ alkyl, $C_{3-8}$ cycloalkyl, Br, Cl, F, I, —C(O)H, $C_{1-4}$ haloalkyl, nitro, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, $C_{1-6}$ alkylamino and ($C_{1-4}$ alkyl)$_2$ amino and wherein R$^4$ and R$^5$ non-phenyl groups may be substituted with 0–5 substituents selected from OH, halogen, —C(O)H, —OC$_{1-6}$-alkyl and $C_{1-6}$ haloalkyl, $C_{1-6}$ alkyl, $C_{3-7}$ c-alkyl, $C_{1-6}$ alkyl(OH)$_n$CO$_2$R wherein R is H or $C_{1-6}$ alkyl, $C_{1-6}$ alkyl(OH)$_n$, wherein n is 0–3 or R$^4$ and R$^5$ may join together to form a $C_{3-6}$ alkylene chain.

[2] The present invention relates to a compound as described directly above in [1] or [1'] wherein R$^1$ is selected from $C_{1-6}$ alkyl, $C_{3-6}$ cycloalkyl, $C_{1-6}$ alkoxy, $C_{1-6}$ alkylthio, —XR$^{1c}$ wherein R$^1$ is substituted with 0–6 substituents selected from halogen, $C_{1-4}$ alkyl or $C_{1-4}$ haloalkyl;

R$^2$ is selected from substituted-$C_{1-10}$ alkyl, branched $C_{3-10}$ alkyl, $C_{2-10}$ alkenyl, $C_{2-10}$ alkynyl, $C_{3-8}$ cycloalkyl, $C_{3-6}$ cycloalkyl $C_{1-6}$ alkyl, —NR$^{2c}$R$^{2d}$ wherein, in the case of substituted-$C_{1-10}$ alkyl, 1–3 substitutents are independently selected from the group R$^{2i}$, R$^{2j}$, R$^{2k}$, $C_{1-6}$ alkyl, $C_{2-8}$ alkenyl, $C_{2-8}$ alkynyl, Br, Cl, F, I, $C_{1-4}$ haloalkyl, —OR$^{2g}$, —NR$^{2g}$R$^{2h}$, —$C_{1-6}$ alkylOR$^{2g}$, and $C_{3-8}$ cycloalkyl which is substituted with 0–1 R$^{2l}$ and in wich 0–1 carbons of $C_{4-8}$ cycloalkyl is replaced by —O— and wherein the R$^2$ groups, other than substituted-$C_{1-10}$ alkyl, are substituted with 0–3 substituents independently selected from the group R$^{2i}$, R$^{2j}$, R$^{2k}$, $C_{1-6}$ alkyl, $C_{2-8}$ alkenyl, $C_{2-8}$ alkynyl, Br, Cl, F, I, $C_{1-4}$ haloalkyl, —OR$^{2g}$, —NR$^{2g}$R$^{2h}$, —$C_{1-6}$ alkylOR$^{2g}$, and $C_{3-8}$ cycloalkyl which is substituted with 0–1 R$^{2l}$ and in wich 0–1 carbons of $C_{4-8}$ cycloalkyl is replaced by —O—.

[3] The present invention also relates to a compound described in groups [1], [1'] or [2] wherein R$^3$ is selected from an aryl group selected from phenyl or substituted versions thereof or a heteroaryl group selected from pyridyl or substituted versions thereof.

[4] The present invention relates to a compound described directly above in groups [1'] and [1]–[3] wherein R$^3$ is substituted with 0–4 substituents independently selected from halogen, $C_{1-4}$ alkyloxy, $C_{1-6}$ alkyl or NR'R" wherein R' and R" are independently selected from H or $C_{1-6}$ alkyl.

[5] The present invention preferrably relates to a compound as described directly above in groups [1'] and [1]–[4] wherein R$^3$ is selected from 2,4-dichlorophenyl, 2-chloro-4-methoxyphenyl, 2,4,6-trimethylphenyl, 2,4,6-trimethoxyphenyl, 2-dimethylamino-4-methyl-pyridin-5-yl, 2,4-dichloro-5-fluorophenyl, 2-chloro-4-methoxy-5- fluorophenyl, 2-chloro-4,5-dimethoxyphenyl or 2-chloro-4, 5-dimethoxyphenyl.

[6] The present invention also preferably relates to a compound as described in groups [1'] and [2]–[5] wherein $R^2$ is selected from $C_1$ alkyl of the formula —CR'R"R''' wherein R', R" and R''' are independently selected from H, $C_{1-6}$ alkyl, $C_{3-7}$ cycloalkyl, hydroxy$C_{1-6}$ alkyl, $C_{1-6}$ alkyloxy$C_{1-6}$ alkyl, $C_{2-6}$ alkenyl, $C_{1-6}$ alkyloxy, hydroxy, with the proviso that each of R', R" and R''' cannot be H; or $R^2$ is selected from $NR^{2c}CR^{2d}$ wherein $R^{2c}$ and $R^{2d}$ are independently selected from H or $C_{1-6}$ alkyl.

[7] The present invention preferably relates to a compound according to groups [1'] and [1]–[6] wherein $R^3$ is selected from an aryl or heteroaryl group attached through an unsaturated carbon atom wherein, aryl is phenyl, each phenyl being substituted with 0–5 substituents independently selected at each occurrence from $C_{1-6}$ alkyl, $C_{3-6}$ cycloalkyl, methylenedioxy, $C_{1-4}$ alkyloxy-$C_{1-4}$ alkyloxy, —$OR^{2m}$, Br, Cl, F, I, $C_{1-4}$ haloalkyl, —CN, —$NO_2$, —SH, —$S(O)_nR^{2n}$, —$COR^{2m}$, —$CO_2R^{2m}$, —$OC(O)R^{2n}$, —$NR^{2g}COR^{2m}$, —$N(COR^{2m})_2$, —$NR^{2g}CONR^{2o}R^{2p}$, —$NR^{2g}CO_2R^{2h}$, —$NR^{2o}R^{2p}$ and $CONR^{2o}R^{2p}$ and up to 1 phenyl, each phenyl substituent being substituted with 0–4 substituents selected from the group $C_{1-3}$ alkyl, $C_{1-3}$ alkoxy, Br, Cl, F, I, —CN, dimethylamino, $CF_3$, $C_2F_5$, $OCF_3$, $SO_2Me$ and acetyl and wherein, heteroaryl is selected at each occurrence from pyridyl, each pyridyl being substitued at 0–4 carbon atoms with a substituent independently selected at each occurrence from the group $C_{1-6}$ alkyl, $C_{3-6}$ cycloalkyl, Br, F, I, $C_{1-4}$ haloalkyl, —CN, nitro, —$OR^{2m}$, —SH, —$S(O)_nR^{2n}$, $COR^{2m}$, —$CO_2R^{2m}$, —$OC(O)R^{2n}$, —$NR^{2g}COR^{2m}$, —$N(COR^{2m})_2$, —$NR^{2g}CONR^{2o}R^{2p}$ and each pyridyl being substituted at any nitrogen atom with 0–1 substituents selected from the group $R^{2g}$, $CO_2R^{3a}$, and $SO_2R^{3a}$.

[8] The present invention preferably relates to a compound of formula (I)

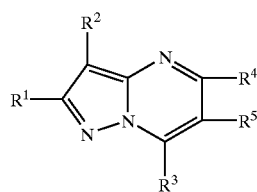

(I)

or a pharmaceutically acceptable salt, stereoisomer or prodrug thereof, wherein $R^1$ is selected from $C_{1-6}$ alkyl, $C_{1-6}$ alkyloxy, —SH or OH;
$R^2$ is selected from $C_{1-4}$ alkyl which is unsubstituted or substituted with 1–4 substitutents selected from $C_{1-6}$ alkyl, $C_{3-8}$ cycloalkyl, $C_{1-6}$ alkyl$OR^{2g}$, $C_{2-6}$ alkenyl or $OR^{2g}$ wherein $R^{2g}$ is H or $C_{1-6}$ alkyl;
$R^3$ is selected from an aryl or heteroaryl group bonded through an unsaturated carbon atom that is unsubstituted or substituted with 1–4 substituents selected from Cl, F, I, Br, —OH, $CF_3$, $S(O)_nC_{1-6}$ alkyl, —$OC_{1-6}$ alkyl, $C_{1-6}$ alkyl or $NR^{2g}R^{2h}$ wherein $R^{2g}$ and $R^{2h}$ are independently selected from H or $C_{1-6}$ alkyl;
$R^4$ and $R^5$ are independently selected from H, $C_{1-6}$ alkyl or $C_{1-6}$ alkyloxy,
with the proviso that when $R^1$ and $R^2$ are unsubstituted, unbranched $C_{1-3}$ alkyl, $R^3$ may not be

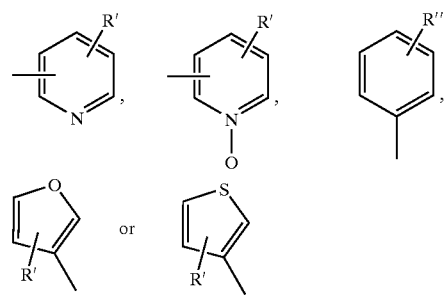

wherein R' is H or $C_{1-3}$ alkyl and R" is H or o-trifluoromethyl, m-trifluoromethyl or m-methoxy (see U.S. Pat. No. 4,281,000).

[9] The present invention also relates to a compound according to group [8] wherein $R^3$ is substituted with 2–4 substituents.

[10] The present invention also relates to a compound according to group [8] or [9] wherein $R^2$ is substituted with 1–4 substituents.

[11] The present invention also relates to a compound according to groups [8]–[10] having the formulae shown in Table 1.

[12] The present invention also relates to a method of antagonizing a CRF-1 receptor in mammals including humans wherein binding to the receptor causes and ultimately results in the treatment of affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF, in mammals comprising administering to the mammal a therapeutically effective amount of a compound of Formula (I) wherein $R^1$ is selected from the group consisting of
$C_{1-6}$ alkyl,
$C_{2-10}$ alkenyl,
$C_{2-10}$ alkynyl,
$C_{3-6}$ cycloalkyl,
$C_{1-6}$ alkyloxy,
$C_{1-6}$ alkylS(O)$_n$,
—$NR^{1a}R^{1B}$ wherein $R^{1a}$ and $R^{1b}$ are independently selected from H, $C_{1-4}$ alkyl, —$C(O)C_{1-4}$alkyl,
—$C(O)NR^{1a}R^{1b}$,
—O—$C(O)C_{1-4}$alkyl,
—$XR^{1c}$ wherein $R^{1c}$ is selected from H or —$C_{1-4}$ alkylaryl;
X is selected from O or $S(O)_n$,
wherein $R^1$ is substituted with 0–6 substituents selected from halogen, $C_{1-4}$ alkyl, $C_{1-6}$ alkyloxy, $C_{1-4}$ haloalkyl, —$NR^{1a}R^{1b}$, —$XR^{1c}$;
$R^2$ is selected from the group consisting of
$C_{1-10}$ alkyl,
$C_{2-10}$ alkenyl,
$C_{2-10}$ alkynyl,
$C_{3-8}$ cycloalkyl,
$C_{3-6}$ cycloalkyl $C_{1-6}$ alkyl,
$C_{1-10}$ alkyloxy, C$_{1-10}$ alkyloxyC$_{1-10}$ alkyl,
C$_{1-4}$ alkoxy C$_{1-4}$ alkyl,
—SO$_2$—C$_{1-10}$alkyl,
—SO$_2$R$^{2a}$ wherein R$^{2a}$ is aryl,
—SO$_2$R$^{2b}$ wherein R$^{2b}$ is heteroaryl,
—NR$^{2c}$R$^{2D}$ wherein R$^{2c}$ and R$^{2d}$ are independently selected from H, C$_{1-8}$ alkyl, C$_{3-8}$ cycloalkyl, C$_{1-6}$ alkyloxyC$_{1-6}$ alkyl, —C(O)C$_{1-4}$alkyl or R$^{2c}$ and R$^{2d}$ may join to form a heterocyclic ring having 0–3 heteroatoms selected from O, N or S,
-halogen,
—CN,
—C(O)NR$^{2c}$R$^{2d}$,
—C(O)R wherein R is C$_{1-6}$ alkyl,
—C(O)OC$_{1-4}$ alkyl,
—C(O)O(CH$_2$)$_2$OR wherein R is C$_{1-3}$ alkyl,
—C(O)O(CH$_2$)$_2$—NHR wherein R is C$_{1-3}$ alkyl,
—C(O)O(CH$_2$)$_2$—NR$^2$,
—C(O)OH,
—C(O)H,
—C(O)Ph,
—C(O)R' wherein R' is aryl, heteroaryl or carboalkoxy;
n is 0, 1 or 2;
R$^2$ is substituted with 0–3 substituents independently selected from R', R'', R''' wherein R', R'' and R''' are independently selected from C$_{1-6}$ alkyl, C$_{3-7}$ cycloalkyl, hydroxyC$_{1-6}$ alkyl, C$_{1-6}$ alkyloxyC$_{1-6}$ alkyl, C$_{2-6}$ alkenyl, C$_{1-6}$ alkyloxy, hydroxy, or
R$^2$ is substituted with 0–3 substituents independently selected from
halogen,
—CN,
—S(O)$_n$R$^{2e}$ wherein R$^{2e}$ is selected from C$_{1-4}$ alkyl, C$_{1-4}$ haloalkyl, C$_{1-4}$ alkyloxy C$_{1-4}$alkyl, C$_{3-6}$ cycloalkyl;
—COR$^{2f}$ wherein R$^{2f}$ is selected from H, C$_{1-4}$ alkyl, C$_{1-4}$ haloalkyl, C$_{1-4}$ alkyloxy C$_{1-4}$ alkyl, C$_{3-6}$ cycloalkyl, and C$_{3-6}$ cycloalkylC$_{1-4}$ alkyl;
—CO$_2$R$^{2f}$,
—NR$^{2g}$COR$^{2f}$ wherein R$^{2g}$ is selected from H, C$_{1-6}$ alkyl, C$_{3-7}$ c-alkyl, C$_{3-6}$ cycloalkyl C$_{1-6}$ alkyl;
—N(COR$^{2f}$)$_2$,
—NR$^{2g}$CONR$^{2f}$R$^{2h}$, wherein R$^{2h}$ is selected from H, C$_{1-6}$ alkyl, C$_{1-4}$ haloalkyl, C$_{1-4}$ alkoxy C$_{1-4}$ alkyl, C$_{3-6}$ cycloalkyl and C$_{3-6}$ cycloalkylC$_{1-6}$ alkyl;
—NR$^{2g}$CO$_2$R$^{2e}$,
—CONR$^{2g}$R$^{2h}$,
1-morpholinyl,
1-piperidinyl,
1-piperazinyl,
and
C$_{3-8}$ cycloalkyl wherein 0–1 carbon atoms in the C$_{4-8}$ cycloalkyl is replaced by a group selected from —O—, —S(O)$_n$—, —NR$^{2g}$—, —NCO$_2$R$^{2e}$, —NCOR$^{2e}$, and —NSO$_2$R$^{2e}$; and wherein N$_4$ in 1-piperazinyl is substituted with 0–1 substituents selected from R$^{2g}$, CO$_2$R$^{2e}$, COR$^{2e}$ and SO$_2$R$^{2e}$; or
the group R$^{2i}$, R$^{2j}$, R$^{2k}$, C$_{1-6}$ alkyl, C$_{2-8}$ alkenyl, C$_{2-8}$ alkynyl, Br, Cl, F, I, C$_{1-4}$ haloalkyl, —OR$^{2g}$, —NR$^{2g}$R$^{2h}$, C$_{1-6}$ alkylOR$^{2g}$, and C$_{3-8}$ cycloalkyl which is substituted with 0–1 R$^{2l}$ and in wich 0–1 carbons of C$_{4-8}$ cycloalkyl is replaced by —O—, wherein
R$^{2i}$ is selected from aryl wherein aryl includes phenyl, naphthyl, indanyl and indenyl, each R$^{2i}$ being substituted with 0–1 OR$^{2m}$ and 0–5 substituents independently selected from the group C$_{1-6}$ alkyl, C$_{3-6}$ cycloalkyl, Br, Cl, F, I, C$_{1-4}$ haloalkyl, —CN, nitro, —SH, —S(O)$_n$R$^{2n}$, —COR$^{2m}$, —OC(O)R$^2$, —NR$^{2g}$COR$^{2m}$, —N(COR$^{2m}$)$_2$, —NR$^{2g}$CONR$^{2o}$R$^{2p}$, —NR$^{2g}$CO$_2$R$^{2n}$, —NR$^{2o}$R$^{2p}$ and —CONR$^{2o}$R$^{2p}$;

R$^{2j}$ is selected from heteroaryl wherein heteroaryl includes pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-s-oxide, 2,3-dihydro-benzothienyl-S-dioxide, indolinyl, benzoxazolin-2-onyl, benzodioxolanyl and benzodioxane, each heteroaryl being substituted on 0–4 carbon atoms with a substituent independently selected from the group C$_{1-6}$ alkyl, C$_{3-6}$ cycloalkyl, Br, Cl, F, I, C$_{1-4}$ haloalkyl, —CN, nitro, OR$^{2m}$, —SH, —S(O)$_n$R$^{2h}$, —COR$^{2m}$, —OC(O)R$^{2h}$, —NR$^{2g}$COR$^{2m}$, —N(COR$^{2m}$)$_2$, —NR$^{2g}$CONR$^{2o}$R$^{2p}$, —NR$^{2g}$CO$_2$R$^{2h}$, —NR$^{2o}$R$^{2p}$ and —CONR$^{2o}$R$^{2p}$ and each heteroaryl being substituted on any nitrogen atom with 0–1 substituents selected from the group R$^{2g}$, CO$_2$R$^{2e}$, COR$^{2e}$ and SO$_2$R$^{2e}$;
R$^{2k}$ is heterocyclyl which is a saturated or partially saturated heteroaryl as defined for R$^{2j}$, each heterocyclyl being substituted on 0–4 carbon atoms with a substituent independently selected from the group C$_{1-6}$ alkyl, C$_{3-6}$ cycloalkyl, Br, Cl, F, I, C$_{1-4}$ haloalkyl, —CN, nitro, —OR$^{2m}$, —SH, —S(O)$_n$R$^{2h}$, —COR$^{2m}$, —OC(O)R$^{2h}$, —NR$^{2g}$COR$^{2m}$, —N(COR$^{2m}$)$_2$, —NR$^{2g}$CONR$^{2o}$R$^{2p}$, NR$^{2g}$CO$_2$R$^{2h}$, —NR$^{2o}$R$^{2p}$ and —CONR$^{2o}$R$^{2p}$ and each heterocyclyl being substituted on any nitrogen atom with 0–1 substituents selected from the group R$^{2f}$, CO$_2$R$^{2e}$, COR$^{2e}$ and SO$_2$R$^{2e}$;
wherein
R$^{2l}$ is H, C$_{1-4}$ alkyl, C$_{3-6}$ cycloalky-C$_{1-4}$ alkyl and C$_{3-8}$ cycloalkyl;
R$^{2m}$ is H, C$_{1-6}$ alkyl, C$_{3-6}$ cycloalkyl C$_{1-6}$ alkyl, C$_{1-2}$ alkyloxy C$_{1-2}$ alkyl, C$_{1-4}$ haloalkyl, R$^{2q}$S(O)$_n$—C$_{1-4}$ alkyl and R$^{2r}$R$^{2s}$N—C$_{2-4}$ alkyl;
R$^{2n}$ is H, C$_{1-6}$ alkyl, C$_{3-10}$ cyloalkyl, C$_{3-6}$ cycloalkyl-C$_{1-6}$ alkyl, C$_{1-2}$ alkyloxy C$_{1-2}$ alkyl, and C$_{1-4}$ haloalkyl;
R$^{2o}$ and R$^{2p}$ are independently selected at each occurrence from H, C$_{1-6}$ alkyl, C$_{3-10}$ cycloalkyl, C$_{3-6}$ cycloalkyl C$_{1-6}$ alkyl and C$_{1-4}$ haloalkyl;
R$^{2q}$ is selected from C$_{1-6}$ alkyl, C$_{1-4}$ haloalkyl, C$_{1-4}$ alkoxy-C$_{1-4}$ alkyl, C$_{3-6}$ cycloalkyl, C$_{3-6}$ cycloalkyl-C$_{1-6}$ alkyl, aryl, aryl(C$_{1-4}$ alkyl), heteroaryl and heteroaryl (C$_{1-4}$ alkyl)- and benzyl, each benzyl being substituted on the aryl moiety with 0–1 substituents selected from the group C$_{1-4}$ alkyl, Br, Cl, F, I, C$_{1-4}$ haloalkyl, nitro, C$_{1-4}$ alkoxy C$_{1-4}$ haloalkoxy, and dimethylamino;
R$^{2r}$R$^{2s}$ taken together with the N form 1-pyrrolidinyl, 1-morpholinyl, 1-piperidinyl or 1-piperazinyl wherein N$_4$ in 1-piperiazinyl is substituted with 0–1 substituents selected from the group R$^{2t}$, CO$_2$R$^{2q}$, COR$^{2q}$ and SO$_2$R$^{2q}$;
R$^{2t}$ is selected from H, C$_{1-4}$ alkyl, C$_{1-4}$ haloalkyl, C$_{1-4}$ alkoxy-C$_{1-4}$ alkyl, C$_{3-6}$ cycloalkyl, C$_{3-6}$ cycloalkyl-C$_{1-6}$ alkyl, aryl, aryl (C$_{1-4}$ alkyl)-, heteroaryl and heteroaryl (C$_{1-4}$ alkyl);
R$^3$ is selected from an aryl or heteroaryl group attached through an unsaturated carbon atom;
aryl is selected from phenyl, naphthyl, indanyl and indenyl, each aryl being substituted with 0–5 substituents independently selected at each occurrence from C$_{1-6}$ alkyl, C$_{3-6}$ cycloalkyl, methylenedioxy, C$_{1-4}$ alkyloxy-C$_{1-4}$ alkyloxy, —OR$^{2m}$, Br, Cl, F, I, C$_{1-4}$ haloalkyl, —CN, —NO$_2$, —SH, —S(O)$_n$R$^{2n}$, —COR$^{2m}$, —COR$^{2m}$, —OC(O)R$^{2n}$, —NR$^{2g}$COR$^{2m}$, —N(COR$^{2m}$)$_2$, —NR$^{2g}$CONR$^{2o}$R$^{2p}$, —NR$^{2g}$CO$_2$R$^{2p}$ and CONR$^{2o}$R$^{2p}$ and up to 1 phenyl, each phenyl substituent being substituted with 0–4 substituents selected from the group $C_{1-3}$ alkyl, $C_{1-3}$ alkoxy, Br, Cl, F, I, —CN, dimethylamino, $CF_3$, $C_2F_5$, $OCF_3$, $SO_2Me$ and acetyl;

heteroaryl is selected from the group pyridyl, pyrimidyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzo-furanyl, 2,3-dihydrobenzothienyl, 2,3-dihydro-benzothienyl-S-oxide, 2,3-dihydrobenzothienyl-s-dioxide, indolinyl, benzoxazolin-2-on-yl, benzodioxolanyl and benzodioxane, each heteroaryl being substitued at 0–4 carbon atoms with a substituent independently selected at each occurrence from the group $C_{1-6}$ alkyl, $C_{3-6}$ cycloalkyl, Br, F, I, $C_{1-4}$ haloalkyl, —CN, $NR^{2g}R^{2h}$, nitro, —$OR^{2m}$, —SH, —$S(O)_nR^{2n}$, $COR^{2m}$, —$CO_2R^{2m}$, —$OC(O)R^{2n}$, —$NR^{2g}COR^{2m}$, —$N(COR^{2m})_n$, —$NR^{2g}CONR^{2o}R^{2p}$ and each heteroaryl being substituted at any nitrogen atom with 0–1 substituents selected from the group $R^{2g}$, $CO_2R^{3a}$, $COR^{3a}$ and $SO_2R^{3a}$ wherein, $R^{3a}$ is selected from the group $C_{1-6}$ alkyl, $C_{1-4}$ cycloalkyl-$C_{1-6}$ alkyl and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^4$ and $R^5$ are independently selected at each occurrence from H, Br, Cl, F, I, —CN, $C_{1-6}$ alkyl, $C_{2-6}$ alkenyl, $C_{2-6}$ alkynyl, $C_{3-8}$ cycloalkyl, $C_{1-6}$ alkyloxy, $C_{1-6}$ alkylthio, $C_{1-6}$ alkylsulfinyl, $C_{1-6}$ alkylsulfonyl, amino, $C_{1-4}$ alkylamino, $(C_{1-4}$ alkyl$)_2$ amino and phenyl, each phenyl is substituted with 0–3 groups selected from the group consisting of $C_{1-7}$ alkyl, $C_{3-8}$ cycloalkyl, Br, Cl, F, I, —C(O)H, $C_{1-4}$ haloalkyl, nitro, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, $C_{1-6}$ alkylamino and $(C_{1-4}$ alkyl$)_2$ amino and wherein $R^4$ and $R^5$ non-phenyl groups may be substituted with 0–5 substituents selected from OH, halogen, —C(O)H, —$OC_{1-6}$-alkyl and $C_{1-6}$ haloalkyl, $C_{1-6}$ alkyl, $C_{3-7}$ c-alkyl, $C_{1-6}$ alkyl$(OH)_nCO_2R$ wherein R is H or $C_{1-6}$ alkyl, $C_{1-6}$ alkyl$(OH)_n$, wherein n is 0–3 or $R^4$ and $R^5$ may join together to form a $C_{3-6}$ alkylene chain.

[13] The present invention also relates to a method as described directly above in group [12] wherein $R^1$ is selected from $C_{1-6}$ alkyl, $C_{3-6}$cycloalkyl, $C_{1-6}$ alkoxy, $C_{1-6}$ alkylthio, —$XR^{1c}$ wherein $R^1$ is substituted with 0–6 substituents selected from halogen, $C_{1-4}$ alkyl or $C_{1-4}$ haloalkyl;

$R^2$ is selected from substituted-$C_{1-10}$ alkyl, branched $C_{3-10}$ alkyl, $C_{2-10}$ alkenyl, $C_{2-10}$ alkynyl, $C_{3-8}$ cycloalkyl, $C_{3-6}$ cycloalkyl $C_{1-6}$ alkyl, —$NR^{2c}R^{2d}$ wherein, in the case of substituted-$C_{1-10}$ alkyl, 1–3 substitutents are independently selected from the group $R^{2i}$, $R^{2j}$, $R^{2k}$, $C_{1-6}$ alkyl, $C_{2-8}$ alkenyl, $C_{2-8}$ alkynyl, Br, Cl, F, I, $C_{1-4}$ haloalkyl, —$OR^{2g}$, —$NR^{2g}R^{2h}$, —$C_{1-6}$ alkyl$OR^{2g}$, and $C_{3-8}$ cycloalkyl which is substituted with 0–1 $R^{2l}$ and in wich 0–1 carbons of $C_{4-8}$ cycloalkyl is replaced by —O— and wherein the $R^2$ groups, other than substituted-$C_{1-10}$ alkyl, are substituted with 0–3 substituents independently selected from the group $R^{2i}$, $R^{2j}$, $R^{2k}$, $C_{1-6}$ alkyl, $C_{2-8}$ alkenyl, $C_{2-8}$ alkynyl, Br, Cl, F, I, $C_{1-4}$ haloalkyl, —$OR^{2g}$, —$NR^{2g}R^{2h}$, —$C_{1-6}$ alkyl$OR^{2g}$, and $C_{3-8}$ cycloalkyl which is substituted with 0–1 $R^{2l}$ and in wich 0–1 carbons of $C_{4-8}$ cycloalkyl is replaced by —O—.

[14] The present invention also relates to a method described directly above in [12] or [13] wherein $R^3$ is selected from an aryl group selected from phenyl or substituted versions thereof or a heteroaryl group selected from pyridyl or substituted versions thereof.

[15] The present invention relates to a method described directly above in groups [12]–[14] wherein $R^3$ is substituted with 0–4 substituents independently selected from halogen, $C_{1-4}$ alkyloxy, $C_{1-6}$ alkyl or NR'R" wherein R' and R" are independently selected from H or $C_{1-6}$ alkyl.

[16] The present invention preferrably relates to a method as described directly above in groups [12]–[15] wherein $R^3$ is selected from 2,4-dichlorophenyl, 2-chloro-4-methoxyphenyl, 2,4,6-trimethylphenyl, 2,4,6-trimethoxyphenyl, 2-dimethylamino-4-methyl-pyridin-5-yl, 2,4-dichloro-5-fluorophenyl, 2-chloro-4-methoxy-5-fluorophenyl, 2-chloro-4,5-dimethoxyphenyl or 2-chloro-4,5-dimethoxyphenyl.

[17] The present invention also preferrably relates to a method as described.in groups [13]–[15] wherein $R^2$ is selected from $C_1$ alkyl of the formula —CR'R"R''' wherein R', R" and R''' are independently selected from H, $C_{1-6}$ alkyl, $C_{3-7}$ cycloalkyl, hydroxy$C_{1-6}$ alkyl, $C_{1-6}$ alkyloxy$C_{1-6}$ alkyl, $C_{2-6}$ alkenyl, $C_{1-6}$ alkyloxy, hydroxy, with the proviso that each of R', R" and R''' cannot be H;

or $R^2$ is selected from NR'R" wherein R' and R" are independently selected from H or $C_{1-6}$ alkyl.

[18] The present invention preferrably relates to a method according to groups [13]–[17] wherein $R^3$ is selected from an aryl or heteroaryl group attached through an unsaturated carbon atom wherein, aryl is phenyl, each phenyl being substituted with 0–5 substituents independently selected at each occurrence from $C_{1-6}$ alkyl, $C_{3-6}$ cycloalkyl, methylenedioxy, $C_{1-4}$ alkyloxy-$C_{1-4}$ alkyloxy, —$OR^{2m}$, Br, Cl, F, I, $C_{1-4}$ haloalkyl, —CN, —$NO_2$, —SH, —$S(O)_nR^{2n}$, —$COR^{2m}$, —$CO_2R^{2m}$, —$OC(O)R^{2n}$, —$NR^{2g}COR^{2m}$, —$N(COR^{2m})_2$, —$NR^{2g}CONR^{2o}R^{2p}$, —$NR^{2g}CO_2R^{2h}$, —$NR^{2o}R^{2p}$ and $CONR^{2o}R^{2p}$ and up to 1 phenyl, each phenyl substituent being substituted with 0–4 substituents selected from the group $C_{1-3}$ alkyl, $C_{1-3}$ alkoxy, Br, Cl, F, I, —CN, dimethylamino, $CF_3$, $C_2F_5$, $OCF_3$, $SO_2Me$ and acetyl and wherein, heteroaryl is selected at each occurrence from pyridyl, each pyridyl being substitued at 0–4 carbon atoms with a substituent independently selected at each occurrence from the group $C_{1-6}$ alkyl, $C_{3-6}$ cycloalkyl, Br, F, I, $C_{1-4}$ haloalkyl, —CN, nitro, —$OR^{2m}$, —SH, —$S(O)_nR^{2n}$, $COR^{2m}$, —$CO_2R^{2m}$, —$OC(O)R^{2n}$, —$NR^{2g}COR^{2m}$, —$N(COR^{2m})_2$, —$NR^{2g}CONR^{2o}R^{2p}$ and each pyridyl being substituted at any nitrogen atom with 0–1 substituents selected from the group $R^{2g}$, $CO_2R^{3a}$, $COR^{3a}$ and $SO_2R^{3a}$.

[19] The present invention preferrably relates to a method of antagonizing a CRF-1 receptor in mammals including humans wherein binding to the receptor causes and ultimately results in the treatment of affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF, in mammals comprising administering to the mammal a therapeutically effective amount of a compound of formula (I)

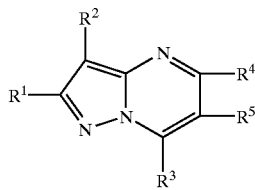

(I)

or a pharmaceutically acceptable salt, stereoisomer or prodrug thereof, wherein
$R^1$ is selected from $C_{1-6}$ alkyl, $C_{1-6}$ alkyloxy, —SH or OH;
$R^2$ is selected from $C_{1-4}$ alkyl which is unsubstituted or substituted with 1–4 substitutents selected from $C_{1-6}$ alkyl, $C_{3-8}$ cycloalkyl, $C_{1-6}$ alkylOR$^{2g}$, $C_{2-6}$ alkenyl or OR$^{2g}$ wherein $R^{2g}$ is H or $C_{1-6}$ alkyl;
$R^3$ is selected from an aryl or heteroaryl group bonded through an unsaturated carbon atom that is unsubstituted or substituted with 1–4 substituents selected from Cl, F, I, Br, —OH, CF$_3$, S(O)$_n$C$_{1-6}$alkyl, —OC$_{1-6}$ alkyl, C$_{1-6}$ alkyl or NR$^{2g}$R$^{2h}$ wherein R$^{2g}$ and R$^{2h}$ are independently selected from H or $C_{1-6}$ alkyl;
$R^4$ and $R^5$ are independently selected from H, $C_{1-6}$ alkyl or $C_{1-6}$ alkyloxy.

[20] The present invention also relates to a method according to group [19] wherein $R^3$ is substituted with 2–4 substituents.

[21] The present invention also relates to a method according to group [19]–[20] wherein $R^2$ is substituted with 1–4 substituents.

[22] The present invention also relates to a method according to group [19]–[21] using the formulae shown in Table 1.

[23] The present invention also provides pharmaceutical compositions comprising compounds of Formula (1) with the variables as recited above in group [1] and [1'] with the proviso that the compounds excluded in proviso (d) in group [1] are included herein and a pharmaceutically acceptable carrier.

[24] The preferred pharmaceutical compositions include those compounds as shown in groups [1'] and [2]–[11] along with a pharmaceutically acceptable carrier.

[25] The present invention also relates to a compound of the formulae shown below having the variables recited above in groups [1'] and [1]–[24]:

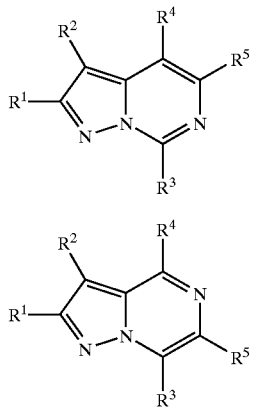

except that the provisos listed in group I are not included for the compounds of formula II and III.

[26] The present invention further comprises a compound of formula II or III in combination with a pharmaceutically acceptable excipient to form a pharmaceutical composition.

[27] The present invention further relates to a method of treating CRF related disorders or conditions or use in therapy of compounds of formula II or III comprising administering a compound of formula II or III with the variables for $R^1$–$R^5$ as shown above in groups [1'] and [1]–[24] to a patient in need of treatment thereof.

Many compounds of this invention have one or more asymmetric centers or planes. Unless otherwise indicated, all chiral (enantiomeric and diastereomeric) and racemic forms are included in the present invention. Many geometric isomers of olefins, C=N double bonds, and the like can also be present in the compounds, and all such stable isomers are contemplated in the present invention. The compounds may be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

The term "alkyl", unless otherwise specified, includes both branched and straight-chain alkyl having the specified number of carbon atoms. "Alkenyl" includes hydrocarbon chains of either a straight or branched configuration and one or more unsaturated carbon-carbon bonds which may occur in any stable point along the chain, such as ethenyl, propenyl, and the like. "Alkynyl" includes hydrocarbon chains of either a straight or branched configuration and one or more triple carbon-carbon bonds which may occur in any stable point along the chain, such as ethynyl, propynyl and the like. "Haloalkyl" is intended to include both branched and straight-chain alkyl having the specified number of carbon atoms, substituted with 1 or more halogen; "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, and so forth. "Halo" or "halogen" includes fluoro, chloro, bromo, and iodo.

The term "substituted", as used herein, means that aone or more hydrogen on the designated atom is replaced with a selection from the indicated group, provided that the designated atom s normal valency is not exceeded, and that the substitution results in a stable compound. When a substitent is keto (i.e., =O), then 2 hydrogens on the atom are replaced.

Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "pharmaceutically acceptable salts" includes acid or base salts of the compounds of formulas (I). Examples of pharmaceutically acceptable salts include, but are not limited to, mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are considered to be any covalently bonded carriers which release the active parent drug of formula (I) in vivo when such prodrug is administered to a mammalian subject. Prodrugs of the compounds of formula (I) are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of formulas (I) and the like.

The term "therapeutically effective amount" of a compound of this invention means an amount effective to antagonize abnormal level of CRF or treat the symptoms of affective disorder, anxiety, depression, immunological, cardiovascular or heart-related diseases and colonic hypersensitivity associated with psychopathological disturbance and stress in a host.

The term "registry reference" refers to computer search generated sources of known chemical structures as identified by specific structure herein.

Compounds prepared according to the synthetic schemes and examples include, without limitation, those compounds specifically set forth in Table 1, hereinbelow, as well as the following:

7-(2,4-dichloro-5-fluorophenyl)-2-ethyl-3-(2-pentyl)-pyrazolo[1,5-a]pyrimidine
7-(2,4-dichlorophenyl)-2-ethyl-6-methyl-3-(2-pentyl)-pyrazolo[1,5-a]pyrimidine
7-(2-chloro-4-methoxyphenyl)-2-ethyl-3-(2-pentyl)pyrazolo[1,5-a]pyrimidine
2-ethyl-3-(2-pentyl)-7-(2,4,6-trimethylphenyl)-pyrazolo[1,5-a]pyrimidine
2-ethyl-3-(2-pentyl)-7-(2,4,6-trimethoxyphenyl)-pyrazolo[1,5-a]pyrimidine
7-(2,4-dichlorophenyl)-2-ethyl-3-(2-pentyl)pyrazolo[1,5-a]pyrimidine
7-(2,4-dichlorophenyl)-2-ethylpyrazolo[1,5-a]pyrimidine-3-carboxaldehyde
7-(2,4-dichlorophenyl)-2-ethyl-3-(1-hydroxyethyl)-pyrazolo[1,5-a]pyrimidine
7-(2,4-dichlorophenyl)-3-(1-ethoxyethyl)-2-ethyl-pyrazolo[1,5-a]pyrimidine
7-(2,4-dichlorophenyl)-3-(1-ethoxyethyl)-2-ethylpyrazolo[1,5-a]pyrimidine
2-ethyl-7-(2-methyl-4-methoxyphenyl)-3-(3-pentyl)-pyrazolo[1,5-a]pyrimidine
2-ethyl-7-(2-methyl-4-methoxyphenyl)-3-(2-pentyl)-pyrazolo[1,5-a]pyrimidine
7-(2,4-dimethylphenyl)-2-ethyl-3-(2-pentyl)-pyrazolo[1,5-a]pyrimidine
7-(2,4-dichlorophenyl)-2-ethyl-5-methylthio-3-(2-pentyl)-pyrazolo[1,5-a]pyrimidine
7-(2,4-dichlorophenyl)-2-ethyl-3-(6-methyl-5-hepten-2-yl)-pyrazolo[1,5-a]pyrimidine
7-(2,4-dichlorophenyl)-2-ethyl-3-(1-hydroxy-4-pentyl)-pyrazolo[1,5-a]pyrimidine
7-(4-difluoromethoxy-2-methyl)-2-ethyl-3-(3-pentyl)pyrazolo[1,5-a]pyrimidine
7-(4-difluoromethoxy-2-methyl)-2-ethyl-3-(2-pentyl)pyrazolo[1,5-a]pyrimidine
7-(2-chloro-4-difluoromethoxyphenyl)-2-ethyl-3-(3-pentyl)pyrazolo[1,5-a]pyrimidine
7-(2-chloro-4-difluoromethoxyphenyl)-2-ethyl-3-(2-pentyl)pyrazolo[1,5-a]pyrimidine
7-(2,4-dimethylphenyl)-2-ethyl-3-(3-pentyl)pyrazolo[1,5-a]pyrimidine
4-(7-(2,4-dichlorophenyl)-2-ethylpyrazolo[1,5-a]pyrimidinyl)pentanoic acid
4-(7-(2,4-dichlorophenyl)-2-ethylpyrazolo[1,5-a]pyrimidinyl)-N-methylpentanamide
3-(5-(benzoxazol-2-ylthio)-2-pentyl)-7-(2,4-dichlorophenyl)-2-ethylpyrazolo[1,5-a]pyrimidine
3-(5-(benzoxazolidinethione-3-yl)-2-pentyl)-7-(2,4-dichlorophenyl)-2-ethylpyrazolo[1,5-a]pyrimidine
7-(2,4-dichlorophenyl)-2-ethyl-3-(1-hydroxy-2-propyl)-pyrazolo[1,5-a]pyrimidine
7-(2,4-dichlorophenyl)-3-(1-ethoxy-2-propyl)-2-ethyl-pyrazolo[1,5-a]pyrimidine
3-(1-acetoxy-2-propyl)-7-(2,4-dichlorophenyl)-2-ethylpyrazolo[1,5-a]pyrimidine
3-(1-acetoxy-2-butyl)-7-(2,4-dichlorophenyl)-2-ethylpyrazolo[1,5-a]pyrimidine
7-(2,4-dichlorophenyl)-2-ethyl-3-(1-hydroxy-3-butyl)pyrazolo[1,5-a]pyrimidine
7-(2,4-dichlorophenyl)-2-ethyl-3-(1-methoxy-3-butyl)pyrazolo[1,5-a]pyrimidine
7-(2,4-dichlorophenyl)-2-ethyl-3-(3-heptyl)-pyrazolo[1,5-a]pyrimidine
7-(2,4-dichlorophenyl)-2-ethyl-3-(3-heptyl)-6-methyl-pyrazolo[1,5-a]pyrimidine
2-ethyl-3-(3-heptyl)-7-(2,4,6-trimethylphenyl)-pyrazolo[1,5-a]pyrimidine
7-(2,4-dichlorophenyl)-2-ethyl-3-(3-pentyl)-pyrazolo[1,5-a]pyrimidine
7-(2,4-dichlorophenyl)-2-ethyl-3-(3-pentyl)-6-methyl-pyrazolo[1,5-a]pyrimidine
2-ethyl-3-(3-pentyl)-7-(2,4,6-trimethylphenyl)-pyrazolo[1,5-a]pyrimidine
2-ethyl-3-(3-pentyl)-7-(2,4,6-trimethoxyphenyl)-pyrazolo[1,5-a]pyrimidine Synthesis Compounds of formula (I) can be prepared by the following synthetic routes and schemes. Where a detailed description is not provided, it is assumed that those skilled in the art of organic synthesis will readily understand the meaning.

Synthesis of compounds of formula (I) may be prepared by the reaction shown in Scheme 1.

The embodiment of this invention concerning compounds of Formula (I) with the structure

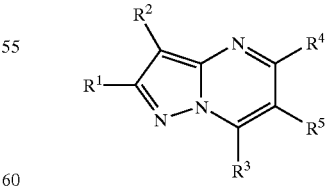

may be prepared according to the following methods:

The pyrazolo[1,5-a]pyrimidine ring system is best prepared by the condensation reaction of a 3-aminopyrazole (1-A, Scheme 1A) with a compound of formula 1-B. Here, Z is ethoxy or dimethylamino, and compound 1-B may be prepared by the reaction of a compound of formula $R^3C$ (=O)CH$_2$R$^6$ with a reagent of formula R$^5$C(Z)(OEt)$_2$. These types of reactions are normally done by heating the two compounds (as a 1:1 mixture) without solvent, and distilling off the volatile components after the reaction is complete. The reaction between 1-A and 1-B is conveniently performed in a solvent such as acetic acid with heating; the acetic acid acts as both solvent and catalyst for the condensation.

Preparation of the pyrazoles can begin with the acylation of a nitrile compound 1-C (Scheme 1B). Normally, a strong base, such as lithium diisopropylamide, is used to deprotonate the nitrile, and the resulting anionic intermediate is treated with a carboxylic ester R$^1$CO$_2$Et or Scheme 1A

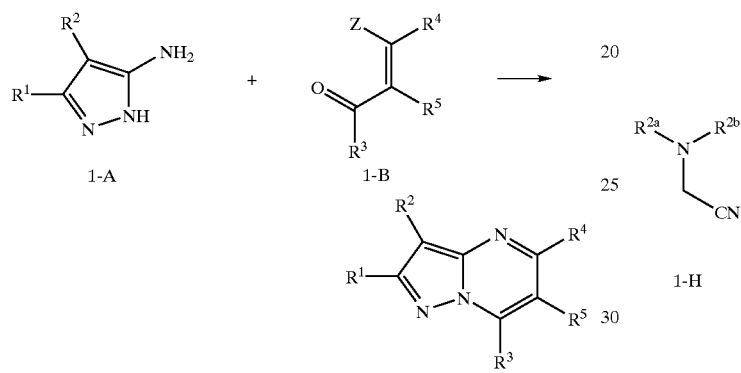

acid chloride R$^1$COCl to generate the ketonitrile 1-D. Condensation of this compound with hydrazine then gives the aminopyrazole. This reaction may be performed in refluxing alcoholic solvent with the optional presence of an acid catalyst, such as acetic acid. Heteroatomic versions of this route are possible. Aminopyrazoles with an R$^1$ group wherein R$^1$=R$^{1a}$O may be prepared by starting with cyanoacetic esters like 1-E, which react with hydrazine to afford 3-amino-5-hydroxypyrazole 1-F. Cyclization with reagent 1-B and O-alkylation with a reagent R$^{1a}$X, wherein X is a halide or pseudohalide group, gives compound 1-G. Finally, strong base treatment of aminonitrile 1-H, usually in the presence of a solvent mixture such as THF/HMPA, followed by acylation and ring-forming, gives diamine 1-K.

Scheme 1B

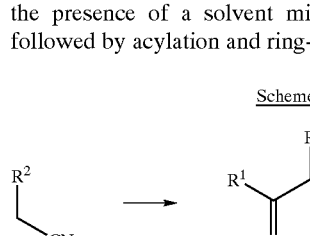

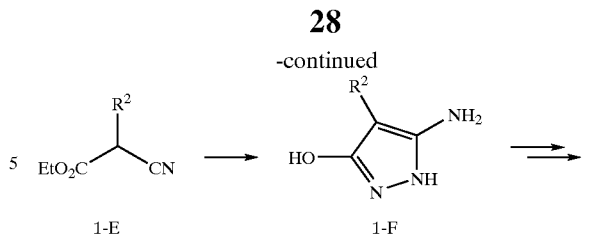

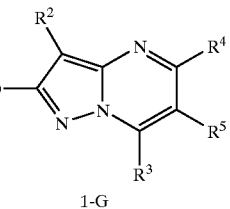

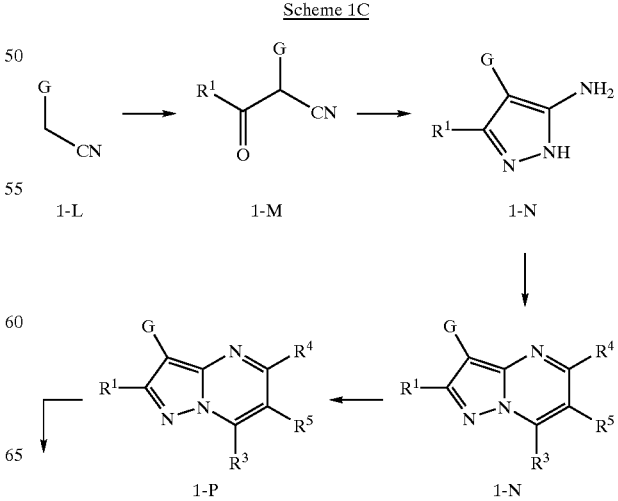

Scheme 1C

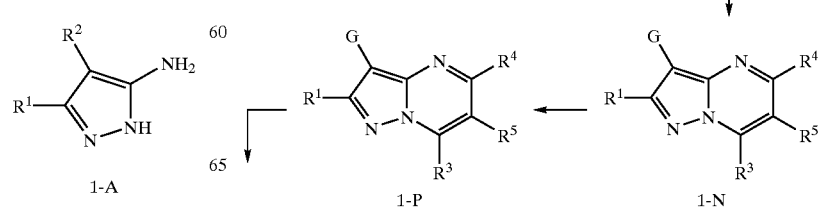

-continued

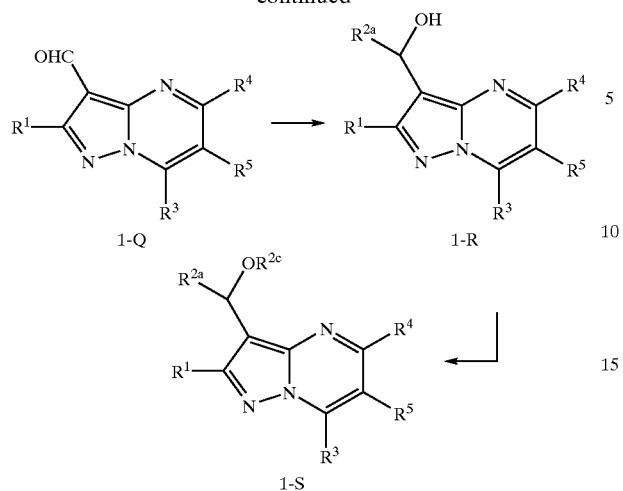

Scheme 1C shows one application of a variation involving a group G (carboalkoxy or CN) which can serve as a functional handle for various R² substitutions. Since G is activating, the acylation of 1-L to give 1-M may not require as strong a base as is used for the transformation of 1-C to 1-D; a reagent such as an orthoester may also be used. Subsequent ring condensations to 1-N and then to 1-P proceed as described earlier. Then, the group G is converted to the R² group of choice wherein R² and substituted versions thereof is as defined in the claims and as above in the specification; the following method is one example. Use of a reducing agent such as diisobutylaluminum hydride in a solvent like toluene or dichloromethane at low temperatures can be used to obtain the aldehyde 1-Q. The aldehyde may be allowed to react with organometallic reagents such as the Grignard reagent $R^{2a}$MgBr to afford the alcohol 1-R. The hydroxy group may then be O-alkylated (typically using a reagent $R^{2c}$X and a base such as sodium hydride in a polar aprotic solvent such as DMF) to give the compound 1-S. Other such manipulations of the G group should be familiar to those skilled in the art of organic synthesis.

Similarly, the remaining variables in the starting materials described above such as R¹ or R³ are determined based upon the desired target moiety. Thus, varying the ketone 1-B with respect to the aryl or heteroaryl group R³ permits synthesis of a compound of formula I having R³ as the desired heteroaryl or aryl group and substituted versions thereof as recited in the claims and above text and as further shown in the examples and table before the appended claims.

The synthesis of compounds of formula II or III may be accomplished by the general schemes shown below in Scheme 2 and in Scheme 3.

SCHEME 2

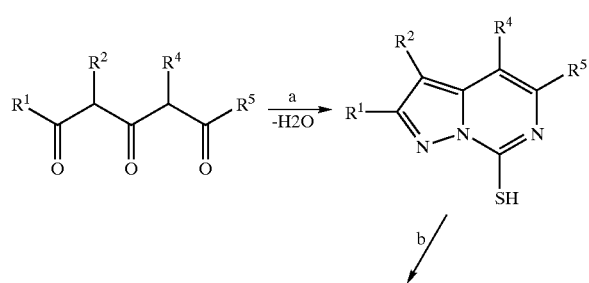

-continued

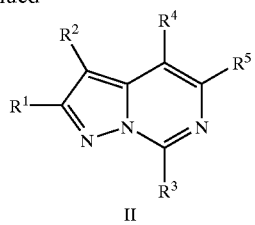

a = H2NNHC(=S)NH2
b = MeI, base; R³—MgX, Ni cat.
Procedure described in Kranze, E and Kutz Chem Ber. 1972, 105, 388.

The variables for R¹–R⁵ are selected from those variables as defined in any of the groups [1]–[24]. The compound of formula II is prepared by starting with the acyclic triketo intermediate shown above which is reacted with reagent a to form the bicyclic intermediate which is then treated with the grignard reagent b to form a compound of formula II.

SCHEME 3

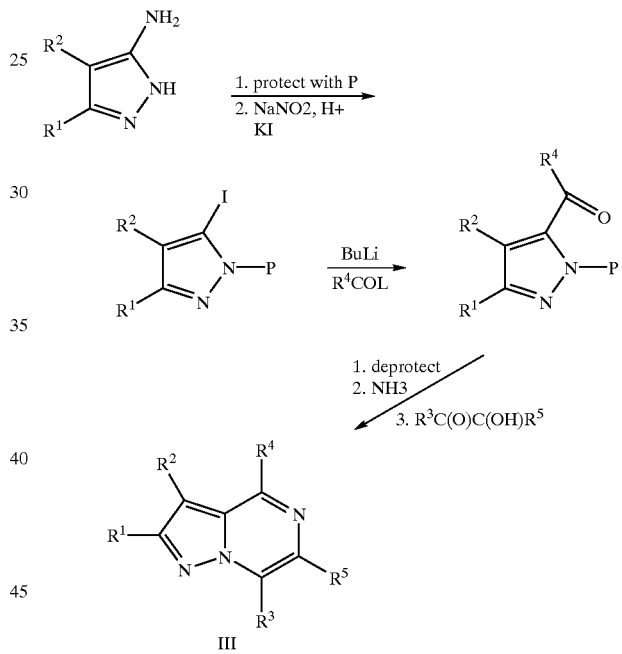

The variables for R¹–R⁵ in Scheme 3 are selected from those described in groups [1]–[24]. Compounds II and III with the variables as defined above are useful as CRF antagonists.

Utility

CRF-R1 Receptor Binding Assay for the Evaluation of Biological Activity

Radioligand Binding Experiments

Compounds of the invention were tested for in vitro activity as CRF receptor antagonists. The tests described below demonstrated that the examples tested had $K_i$s of 10,000 nM or less a nd are thus useful as CRF receptor antagonists. Preferred antagonists have or will have a $K_i$ of 1,000 nM or less. Radioligand binding experiments were performed with membranes from rat frontal cortex to determine binding affinities ($K_i$'s) of test compounds for the rat $CRH_1$ receptor using a modified version of methods described earlier (see E. B. DeSouza, J. Neurosci, 7:88, 1987). Rat cortex was homogenized in tissue buffer (containing 50 mM HEPES, 10 mM $MgCl_2$, 2 mM EGTA, and 1 µg/ml each of aprotonin, leupeptin, and pepstatin, pH 7.0 @ 23° C.) using a Brinkman Polytron (PT-10, setting 6 for 10 sec). The homogenate was centrifuged at 48,000×g for 12 min and the resulting pellet was washed by two sequential re-suspension and centrifugation steps. The final pellet was suspended to tissue buffer to a working concentration of 0.1 mg/ml protein. Protein determinations were made using the bicinchoninic acid (BCA) assay (Pierce, Rockford, Ill.) with bovine serum albumin as the standard.

All test compounds were prepared in assay buffer, which was identical to the tissue buffer except for the inclusion of 0.15 mM bacitracin and 0.1% w/v ovalbumin. Binding assay were conducted in disposable polypropylene 96-well plates (Costar Corp., Cambridge, Mass.) and initiated by the addition of 100 µl membrane homogenate (containing 40–60 µg protein) to 200 µl of assay buffer containing radioligands (150 pM, final concentration, $[^{125}I]$ tyr° ovine CRH; New England Nuclear, Mass.) and competing test compounds. Specific binding was determined in the presence of 10 µM α-helical CRH. Competition experiments were conducted using 12 concentrations of ligand (ranging from $1\times10^{-11}$ to $1\times10^{-5}$ M). The reactions mixtures were incubated to equilibrium for 2 hr at 23° C. and terminated by rapid filtration using a cell harvester (Inotech Biosystems Inc., Lansing, Mich.) over GFF glass-fibers (pre-soaked in 0.3% v/v polyethyleneimine). Filters were rapidly washed 3× with 0.3 ml cold wash buffer (PBS, pH 7.0, containing 0.01% Triton X-100), dried, and counted in a gamma counter at 80% efficiency.

Binding affinities ($K_i$'s) of ligands for the $CRH_1$ receptor were calculated using the iterative nonlinear regression curve-fitting programs (LIGAND) of Munson and Rodbard (Anal. Biochem. 1980, 107, 220–239) or Prism (GraphPad Prism, San Diego, Calif.). Data were best-fit by the one-site/state competition equation.

Inhibition of CRF-Stimulated Adenylate Cyclase Activity

Inhibition of CRF-stimulated adenylate cyclase activity can be performed as described by G. Battaglia et al. *Synapse* 1:572 (1987). Briefly, assays are carried out at 37° C. for 10 min in 200 ml of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/ml phosphocreatine kinase, 5 mM creatine phosphate, 100 mM guanosine 5-triphosphate, 100 nM OCRF, antagonist peptides (concentration range $10^{-9}$ to $10^{-6m}$) and 0.8 mg original wet weight tissue (approximately 40–60 mg protein). Reactions are initiated by the addition of 1 mM $ATP/^{32}P]$ ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 µl of [³H]cAMP (approximately 40,000 dpm) is added to each tube prior to separation. The separation of [³²P]cAMP from [³²P]ATP is performed by sequential elution over Dowex and alumina columns.

In vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn *Brain Research Reviews* 15:71 (1990). Compounds may be tested in any species of rodent or small mammal.

Compounds of this invention have utility in the treatment of inbalances associated with abnormal levels of corticotropin releasing factor in patients suffering from depression, affective disorders, and/or anxiety.

Compounds of this invention can be administered to treat these abnormalities by means that produce contact of the active agent with the agent s site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The preferred indication and use of the compounds and compositions of the invention is in the treatment of depression or anxiety.

The compounds of this invention may also be used as reagents or standards in the biochemical study of neurological function, dysfunction, and disease.

The following examples are provided to describe the invention in further detail. These examples, which set forth the best mode presently contemplated for carrying out the invention, are intended to illustrate and not to limit the invention.

EXAMPLES

The following specific synthetic example describes the procedures which, when applied to appropriately substituted substrates, may be employed in the synthesis of the compounds in Table 1.

Example 1

Preparation of 7-(2,4-dichlorophenyl)-2-ethyl-3-(3-pentyl)pyrazolo[1,5-a]pyrimidine Part A. A mixture of 2-ethyl-1-bromobutane (10.0 mL, 71.4 mmol), potassium cyanide (14.0 g, 215 mmol) and aliquat 336 (10 drops) in 50 mL water was heated to reflux overnight with vigorous stirring. The mixture was cooled, and extracted with dichloromethane (2×50 mL). The extracts were combined, dried over magnesium sulfate, filtered and evaporated. The residual liquid was distilled bulb-to-bulb to afford pure product, 3-ethylpentanenitrile (5.50 g, 49.5 mmol, 69%). b.p. 40–45° C. (5 mm Hg). Spectral data: $^1$H NMR (300 MHz, CDCl$_3$): δ 22.33 (2H, d, J=5.8 Hz), 1.62–1.36 (5H, m), 0.92 (6H, t, J=7.3 Hz). MS (H$_2$O-GC/MS): m/e 112 (100).

Part B. A solution of diisopropylamine (7.50 mL, 57.2 mmol) in THF (100 mL) was cooled to −78° C., and treated with n-butyllithium (34.0 mL of a 1.6 M solution in hexane). The solution was warmed briefly to 0° C., and then recooled to −78° C. The nitrile compound from Part A was then added by syringe, and the solution was allowed to stir for 1 hour. Then, ethyl propionate (6.50 mL, 56.7 mmol) was added by syringe, and the resulting mixture was allowed to stir and warm to ambient temperature for 12 hours. It was poured into 200 mL of satd. aq. NH$_4$Cl solution, and this was extracted with ethyl acetate (2×200 mL). The extracts were combined, dried over magnesium sulfate, filtered and evaporated. The residual oil was separated by column chromatography (silica gel, 10:90 ethyl acetate-hexane) to afford the product, 4-cyano-5-ethyl-3-heptanone, as an oil 4.06 g, 24.3 mmol, 49%). TLC R$_F$ 0.47 (20:80 ethyl acetate-hexane). Spectral data: $^1$H NMR (300 MHz, CDCl$_3$): δ 3.49 (1H, d, J=4.4 Hz), 2.74 (2H, q, J=7.3 Hz), 2.08–1.98 (1H, m), 1.70–1.58 (1H, m), 1.50–1.20 (3H, m), 1.12 (3H, t, J=7.3 Hz), 0.95 (3H, t, J=7.3 Hz), 0.91 (3H, t, J=7.3 Hz). MS (H$_2$O-GC/MS): m/e 167 (100).

Part C. A solution of the ketonitrile from Part B (4.06 g, 24.3 mmol), hydrazine hydrate (2.70 mL, 55.7 mmol) and acetic acid (5.00 mL, 83.7 mmol) in benzene (50 mL) was heated to reflux under a Dean-Stark trap with azeotropic distillation of water. After being heated for 12 hours, the mixture was cooled and poured into 100 mL 1 N aq. NaHCO$_3$ solution. This was extracted with ethyl acetate (2×100 mL), and the extracts were washed in sequence with brine, combined, dried over sodium sulfate, filtered and evaporated to afford sufficiently-pure product, 3-amino-5-ethyl-4-(3-pentyl)pyrazole, as a viscous oil (2.48 g, 13.7 mmol, 56%). Spectral data: $^1$H NMR (300 MHz, CDCl$_3$): δ 3.48 (2H, br), 2.54 (2H, q, J=7.3 Hz), 2.25–2.14 (1H, m), 1.71–1.49 (4H, m), 1.20 (3H, t, J=7.3 Hz), 0.83 (6H, t, J=7.3 Hz), 1H missing. MS (NH$_3$—CI): m/e 183 (12), 182 (100).

Part D. A mixture of 2,4-dichloroacetophenone (10.0 g, 52.9 mmol) and dimethylformamide diethyl acetal (10.0 mL, 58.3 mmol) was heated to reflux for 12 hours, then cooled and evaporated under high vacuum. The residual oil was separated by column chromatography (silica gel, 1:1 ethyl acetate-hexane) to afford the product, 1-(2,4-dichlorobenzoyl)-2-(N,N-dimethylamino)ethene, as a viscous oil (12.11 g, 49.6 mmol, 94%). TLC R$_F$ 0.05 (20:80 ethyl acetate-hexane). Spectral data: $^1$H NMR (300 MHz, CDCl$_3$): δ 7.40 (1H, d, J=2.2 Hz), 7.38–7.23 (3H, m), 5.33 (1H, d, J=12.4 Hz), 3.11 (3H, br s), 2.89 (3H, br s). MS (NH$_3$—CI): m/e 249 (1), 248 (10), 247 (8), 246 (64), 245 (16), 244 (100).

Part E. A solution of the product of Part C (2.25 g, 1.38 mmol) and that of Part D (0.337 g, 1.38 mmol) in acetic acid (5 mL) was heated to reflux for 10 hours, then cooled, and poured into water. This was neutralized by the addition of solid sodium bicarbonate until the evolution of CO$_2$ subsided. The resulting mixture was extracted with ethyl acetate (2×100 mL), and the extracts were washed with brine (100 mL), combined, dried over sodium sulfate, filtered and evaporated. The resulting mixture of regioisomeric products (ca. 5:1 estimated by TLC visualization) were separated by column chromatography (silica gel, 10:90 ethyl acetate-hexane) to afford the major regioisomer as the more TLC-mobile product, which was the title compound. TLC R$_F$ 0.32 (10:90 ethyl acetate-hexane). Spectral data: $^1$H NMR (300 MHz, CDCl$_3$): δ 8.38 (1H, d, J=4.1 Hz), 7.58 (1H, d, J=2.0 Hz), 7.55 (1H, d, J=8.2 Hz), 7.41 (1H, dd, J=8.2, 2.0 Hz), 6.65 (1H, d, J=4.1 Hz), 2.79 (2H, q, J=7.7 Hz), 2.78–2.68 (1H, m), 2.03–1.79 (4H, m), 1.25 (3H, t, J=7.7 Hz), 0.83 (6H, t, J=7.3 Hz). MS (NH$_3$—CI): m/e 367 (2), 366 (11), 365 (15), 364 (65), 363 (25), 362 (100). Analysis calc'd for C$_{19}$H$_{21}$Cl$_2$N$_3$: C, 62.99; H, 5.84; N, 11.60; found: C, 62.97; H, 5.74; N, 11.49.

Examples 2–30 were prepared and/or may be prepared in an analogous fashion.

Example 31

Preparation of 7-(2,4-dichlorophenyl)-3-(N,N-diethylamino)-2-ethylpyrazolo[1,5-a]pyrimidine Part A. A solution of diisopropylamine (10.0 mL, 76.3 mmol) in THF (60 mL) was cooled to −78° C., and treated with n-butyllithium (50.0 mL of a 1.6 M solution in hexane). The solution was warmed briefly to 0° C., and then recooled to −78° C. To this was added first, N,N'-dimethylpropyleneurea as cosolvent (15 mL), then, diethylaminoacetonitrile (10.0 mL, 74.1 mmol), and the solution was allowed to stir for 1 hour. Then, ethyl propionate (10.0 mL, 87.2 mmol) was added by syringe, and the resulting mixture was allowed to stir and warm to ambient temperature for 12 hours. It was poured into 200 mL of satd. aq. $NH_4Cl$ solution, and this was extracted with ethyl acetate (2×200 mL). The extracts were combined, dried over magnesium sulfate, filtered and evaporated. The residual oil was separated by column chromatography (silica gel, 20:80 ethyl acetate-hexane) to afford the product, 2-(N,N-diethylamino)-3-oxopentanenitrile, as an oil (5.31 g, 31.6 mmol, 43%).

Part B. A solution of the ketonitrile from Part A, hydrazine hydrate (3.00 mL, 61.9 mol) and acetic acid (6.00 mL, 104 mmol) in benzene (100 mL) was heated to reflux under a Dean-Stark trap with azeotropic removal of water for a period of 14 hours. Excess hydrazine (2 mL) and excess acetic acid (5 mL) were then added, and refluxing was allowed to continue for 20 hours. The solution was cooled and poured into 200 mL 1 N aq. $NaHCO_3$ solution. This was extracted with ethyl acetate (2×200 mL), and the extracts were washed in sequence with brine, combined, dried over sodium sulfate, filtered and evaporated. The residue was separated by column chromatography (silica gel, 30:70 ethyl acetate to remove unreacted starting material, then ethyl acetate) to afford the product, 3-amino-4-(N,N-diethylamino)-5-ethylpyrazole, as a viscous oil which darkens in air (750 mg, 4.41 mmol, 15%).

Part C. A solution of the diamine from Part B (300 mg, 1.76 mmol) and 1-(2,4-dichlorobenzoyl)-2-(N,N-dimethylamino)ethene (470 mg, 1.93 mmol) in acetic acid (5 mL) was heated to 100° C. for 10 hours, then cooled and poured into satd. aq. $NaHCO_3$ solution (100 mL). This mixture was extracted with ethyl acetate (2×100 mL), and the extracts were washed with brine, combined, dried over sodium sulfate, filtered and evaporated. The residual oil was separated by column chromatography (silica gel, 20:80 ethyl acetate-hexane) to afford the title product as a red oil (411 mg, 1.13 mmol, 64%). Spectral data: $^1$H NMR (300 MHz, $CDCl_3$): δ 8.38 (1H, d, J=4.0 Hz), 7.58 (1H, d, J=1.8 Hz), 7.56 (1H, d, J=8.4 Hz), 7.42 (1H, dd, J=8.4, 1.8 Hz), 6.65 (1H, d, J=4.0 Hz), 3.27 (4H, q, J=7.3 Hz), 2.80 (2H, q, J=7.3 Hz), 1.26 (3H, t, J=7.3 Hz), 1.00 (6H, t, J=7.3 Hz). MS ($NH_3$—CI): calculated for $C_{18}H_{21}Cl_2N_4$ 363.1143, measured 363.1146; m/e 367 (6), 366 (14), 365 (81), 364 (28), 363 (100).

Examples 32–45 were and/or may be prepared in an analogous manner.

Examples 51 and 92

Preparation of 7-(2,4-dichlorophenyl)-2-hydroxy-6-methyl-3-(3-pentyl)pyrazolo[1,5-a]pyrimidine (92) and 7-(2,4-dichlorophenyl)-2-methoxy-6-methyl-3-(3-pentyl)pyrazolo[1,5-a]pyrimidine (51)

Part A. A solution of triphenylphosphine (25.0 g, 95.3 mmol) in THF (200 mL) was cooled to −30° C., and diethyl azodicarboxylate (15.0 mL, 95.2 mmol) was slowly added dropwise in conc. THF solution. After the addition was complete, the mixture was treated with a THF solution of 3-pentanol (10.0 mL, 90.6 mmol) and ethyl cyanoacetate (10.0 mL, 92.1 mmol). The resulting mixture was allowed to stir and warm to ambient temperature for 12 hours, then was evaporated. The residual oil was separated by column chromatography (10:90 ethyl acetate-hexane) to afford the product, ethyl 2-cyano-3-ethylpentanoate, as a viscous oil (3.41 g, 18.6 mmol, 21%). TLC $R_F$ 0.43 (20:80 ethyl acetate-hexane). Spectral data: $^1$H NMR (300 MHz, $CDCl_3$): δ 4.27 (2H, q, J=7.0 Hz), 3.61 (1H, d, J=4.4 Hz), 2.04–1.93 (1H, m), 1.70–1.35 (4H, m), 1.33 (3H, t, J=7.0 Hz), 0.97 (3H, t, J=7.3 Hz), 0.94 (3H, t, J=7.3 Hz). MS ($H_2O$-GC/MS): m/e 185 (8), 184 (100).

Part B. A solution of the cyanoester from Part A and hydrazine hydrate (2.00 mL, 41.2 mmol) in ethanol (30 mL) was heated to reflux for 10 hours. The solution was cooled, and poured into water. This was extracted with ethyl acetate (2×100 mL), and the extracts were washed with brine, combined, dried over sodium sulfate, filtered and evaporated. The resulting oil was sufficiently pure product, 3-amino-5-hydroxy-4-(3-pentyl)pyrazole (1.29 g, 7.62 mmol, 41%).

Part C. A solution of the pyrazole compound from Part B (478 mg, 2.82 mmol) and 2-(2,4-dichlorobenzoyl)-1-(N,N-dimethylamino)-1-propene (729 mg, 2.82 mmol) in acetic acid (10 mL) was heated to reflux for 10 hours. The solution was cooled and poured into water (100 mL). This was neutralized by the addition of solid $NaHCO_3$, and the mixture was extracted with ethyl acetate (2×100 mL). The extracts were washed with brine, combined, dried over sodium sulfate, filtered and evaporated. The residue was separated by column chromatography (silica gel, 10:90 ethyl acetate-hexane) to give the compound of Example 92 as a solid (210 mg, 0.576 mmol, 20%). m.p. 227–228° C. TLC $R_F$ 0.46 (20:80 ethyl acetate-hexane). Spectral data: $^1$H NMR (300 MHz, $CDCl_3$): δ 10.53 (1H, br s), 8.27 (1H, s), 7.63 (1H, d, J=2.2 Hz), 7.45 (1H, dd, J=8.4, 2.2 Hz), 7.25 (1H, d, J=8.4 Hz), 2.72–2.62 (1H, m), 2.02 (3H, s), 1.77–1.65 (4H, m), 0.82 (6H, t, J=7.5 Hz). MS (ESI): m/e 366 (69), 364 (100).

Part D. A solution of the compound of Example 92 (31 mg, 0.085 mmol) and Proton-Sponge (20 mg, 0.093 mmol) in acetonitrile (2 mL) was cooled to 0° C., and treated with methyl methanetrifluorosulfonate (10 μL, 0.088 mmol). After stirring for 10 hours and warming to ambient temperature, the mixture was evaporated, and the residue was separated directly by column chromatography (silica gel, 10:90 ethyl acetate-hexane) to give the compound of Example 51 as a viscous oil (7 mg, 0.019 mmol, 22%). TLC $R_F$ 0.55 (20:80 ethyl acetate-hexane). Spectral data: $^1$H NMR (300 MHz, $CDCl_3$): δ 8.27 (1H, s), 7.60 (1H, d, J=2.2 Hz), 7.43 (1H, dd, J=8.0, 2.0 Hz), 7.32 (1H, d, J=8.0 Hz), 3.84 (3H, s), 2.80–2.70 (1H, m), 2.08 (3H, s), 1.86–1.70 (4H, m), 0.82 (6H, t, J=7.4 Hz). MS ($NH_3$—CI): m/e 383 (2), 382 (12), 381 (14), 380 (65), 379 (25), 378 (100).

Examples 52–90 and 92 were and/or may be prepared according to the procedures described above. The additional examples prepared or readily prepared (93–281) were (or may be) prepared according to the procedures described above and shown in the general schemes and described in the text. Table 1 shows the preferred compounds.

TABLE 1

[Structure: pyrazolo[1,5-a]pyrimidine core with R¹ at 2-position, R² at 3-position, R³ at 7-position, R⁴ at 5-position, R⁵ at 6-position]

| Ex No | R¹ | R² | R⁴ | R⁵ | R³ | m.p. °C. |
|---|---|---|---|---|---|---|
| 1 | C₂H₅ | (C₂H₅)₂CH | H | H | 2,4-Cl₂—C₆H₃ | oil[a] |
| 2 | C₂H₅ | (C₂H₅)₂CH | H | H | 2-Cl-4-CH₃O—C₆H₃ | 88–89 |
| 3 | C₂H₅ | (C₂H₅)₂CH | H | H | 2,4,6-(CH₃)₃—C₆H₂ | oil[b] |
| 4 | C₂H₅ | (C₂H₅)₂CH | H | H | 2,4,6-(OCH₃)₃—C₆H₂ | 166–167 |
| 5 | C₂H₅ | (C₂H₅)₂CH | H | H | 2-(CH₃)₂N-4-CH₃-pyridin-5-yl | — |
| 6 | C₂H₅ | (C₂H₅)₂CH | H | CH₃ | 2,4-Cl₂—C₆H₃ | 90–91 |
| 7 | C₂H₅ | (C₂H₅)₂CH | H | CH₃ | 2-Cl-4-CH₃O—C₆H₃ | — |
| 8 | C₂H₅ | (C₂H₅)₂CH | H | CH₃ | 2,4,6-(CH₃)₃—C₆H₂ | — |
| 9 | C₂H₅ | (C₂H₅)₂CH | H | CH₃ | 2,4,6-(OCH₃)₃—C₆H₂ | — |
| 10 | C₂H₅ | (C₂H₅)₂CH | H | CH₃ | 2-(CH₃)₂N-4-CH₃-pyridin-5-yl | — |
| 11 | C₂H₅ | (C₂H₅)₂CH | CH₃ | H | 2,4-Cl₂—C₆H₃ | — |
| 12 | C₂H₅ | (C₂H₅)₂CH | CH₃ | H | 2-Cl-4-CH₃O—C₆H₃ | — |
| 13 | C₂H₅ | (C₂H₅)₂CH | CH₃ | H | 2,4,6-(CH₃)₃—C₆H₂ | — |
| 14 | C₂H₅ | (C₂H₅)₂CH | CH₃ | H | 2,4,6-(OCH₃)₃—C₆H₂ | — |
| 15 | C₂H₅ | (C₂H₅)₂CH | CH₃ | H | 2-(CH₃)₂N-4-CH₃-pyridin-5-yl | — |
| 16 | C₂H₅ | C₄H₉(C₂H₅)CH | H | H | 2,4-Cl₂—C₆H₃ | oil[c] |
| 17 | C₂H₅ | C₄H₉(C₂H₅)CH | H | H | 2-Cl-4-CH₃O—C₆H₃ | — |
| 18 | C₂H₅ | C₄H₉(C₂H₅)CH | H | H | 2,4,6-(CH₃)₃—C₆H₂ | oil[d] |
| 19 | C₂H₅ | C₄H₉(C₂H₅)CH | H | H | 2,4,6-(OCH₃)₃—C₆H₂ | — |
| 20 | C₂H₅ | C₄H₉(C₂H₅)CH | H | H | 2-(CH₃)₂N-4-CH₃-pyridin-5-yl | — |
| 21 | C₂H₅ | C₄H₉(C₂H₅)CH | H | CH₃ | 2,4-Cl₂—C₆H₃ | 78–79 |
| 22 | C₂H₅ | C₄H₉(C₂H₅)CH | H | CH₃ | 2-Cl-4-CH₃O—C₆H₃ | — |
| 23 | C₂H₅ | C₄H₉(C₂H₅)CH | H | CH₃ | 2,4,6-(CH₃)₃—C₆H₂ | — |
| 24 | C₂H₅ | C₄H₉(C₂H₅)CH | H | CH₃ | 2,4,6-(OCH₃)₃—C₆H₂ | — |
| 25 | C₂H₅ | C₄H₉(C₂H₅)CH | H | CH₃ | 2-(CH₃)₂N-4-CH₃-pyridin-5-yl | — |
| 26 | C₂H₅ | C₄H₉(C₂H₅)CH | CH₃ | H | 2,4-Cl₂—C₆H₃ | — |
| 27 | C₂H₅ | C₄H₉(C₂H₅)CH | CH₃ | H | 2-Cl-4-CH₃O—C₆H₃ | — |
| 28 | C₂H₅ | C₄H₉(C₂H₅)CH | CH₃ | H | 2,4,6-(CH₃)₃—C₆H₂ | — |
| 29 | C₂H₅ | C₄H₉(C₂H₅)CH | CH₃ | H | 2,4,6-(OCH₃)₃—C₆H₂ | — |
| 30 | C₂H₅ | C₄H₉(C₂H₅)CH | CH₃ | H | 2-(CH₃)₂N-4-CH₃-pyridin-5-yl | — |
| 31 | C₂H₅ | (C₂H₅)₂N | H | H | 2,4-Cl₂—C₆H₃ | oil[e] |
| 32 | C₂H₅ | (C₂H₅)₂N | H | H | 2-Cl-4-CH₃O—C₆H₃ | 97–98 |
| 33 | C₂H₅ | (C₂H₅)₂N | H | H | 2,4,6-(CH₃)₃—C₆H₂ | — |
| 34 | C₂H₅ | (C₂H₅)₂N | H | H | 2,4,6-(OCH₃)₃—C₆H₂ | — |
| 35 | C₂H₅ | (C₂H₅)₂N | H | H | 2-(CH₃)₂N-4-CH₃-pyridin-5-yl | — |
| 36 | C₂H₅ | (C₂H₅)₂N | H | CH₃ | 2,4-Cl₂—C₆H₃ | — |
| 37 | C₂H₅ | (C₂H₅)₂N | H | CH₃ | 2-Cl-4-CH₃O—C₆H₃ | — |
| 38 | C₂H₅ | (C₂H₅)₂N | H | CH₃ | 2,4,6-(CH₃)₃—C₆H₂ | — |
| 39 | C₂H₅ | (C₂H₅)₂N | H | CH₃ | 2,4,6-(OCH₃)₃—C₆H₂ | — |
| 40 | C₂H₅ | (C₂H₅)₂N | H | CH₃ | 2-(CH₃)₂N-4-CH₃-pyridin-5-yl | — |
| 41 | C₂H₅ | (C₂H₅)₂N | CH₃ | H | 2,4-Cl₂—C₆H₃ | — |
| 42 | C₂H₅ | (C₂H₅)₂N | CH₃ | H | 2-Cl-4-CH₃O—C₆H₃ | — |
| 43 | C₂H₅ | (C₂H₅)₂N | CH₃ | H | 2,4,6-(CH₃)₃—C₆H₂ | — |
| 44 | C₂H₅ | (C₂H₅)₂N | CH₃ | H | 2,4,6-(OCH₃)₃—C₆H₂ | — |
| 45 | C₂H₅ | (C₂H₅)₂N | CH₃ | H | 2-(CH₃)₂N-4-CH₃-pyridin-5-yl | — |
| 46 | OCH₃ | (C₂H₅)₂CH | H | H | 2,4-Cl₂—C₆H₃ | — |
| 47 | OCH₃ | (C₂H₅)₂CH | H | H | 2-Cl-4-CH₃O—C₆H₃ | — |
| 48 | OCH₃ | (C₂H₅)₂CH | H | H | 2,4,6-(CH₃)₃—C₆H₂ | — |
| 49 | OCH₃ | (C₂H₅)₂CH | H | H | 2,4,6-(OCH₃)₃—C₆H₂ | — |
| 50 | OCH₃ | (C₂H₅)₂CH | H | H | 2-(CH₃)₂N-4-CH₃-pyridin-5-yl | — |
| 51 | OCH₃ | (C₂H₅)₂CH | H | CH₃ | 2,4-Cl₂—C₆H₃ | oil[f] |
| 52 | OCH₃ | (C₂H₅)₂CH | H | CH₃ | 2-Cl-4-CH₃O—C₆H₃ | — |
| 53 | OCH₃ | (C₂H₅)₂CH | H | CH₃ | 2,4,6-(CH₃)₃—C₆H₂ | — |
| 54 | OCH₃ | (C₂H₅)₂CH | H | CH₃ | 2,4,6-(OCH₃)₃—C₆H₂ | — |
| 55 | OCH₃ | (C₂H₅)₂CH | H | CH₃ | 2-(CH₃)₂N-4-CH₃-pyridin-5-yl | — |
| 56 | OCH₃ | (C₂H₅)₂CH | CH₃ | H | 2,4-Cl₂—C₆H₃ | — |
| 57 | OCH₃ | (C₂H₅)₂CH | CH₃ | H | 2-Cl-4-CH₃O—C₆H₃ | — |
| 58 | OCH₃ | (C₂H₅)₂CH | CH₃ | H | 2,4,6-(CH₃)₃—C₆H₂ | — |
| 59 | OCH₃ | (C₂H₅)₂CH | CH₃ | H | 2,4,6-(OCH₃)₃—C₆H₂ | — |
| 60 | OCH₃ | (C₂H₅)₂CH | CH₃ | H | 2-(CH₃)₂N-4-CH₃-pyridin-5-yl | — |
| 61 | OCH₃ | C₄H₉(C₂H₅)CH | H | H | 2,4-Cl₂—C₆H₃ | — |
| 62 | OCH₃ | C₄H₉(C₂H₅)CH | H | H | 2-Cl-4-CH₃O—C₆H₃ | — |
| 63 | OCH₃ | C₄H₉(C₂H₅)CH | H | H | 2,4,6-(CH₃)₃—C₆H₂ | — |
| 64 | OCH₃ | C₄H₉(C₂H₅)CH | H | H | 2,4,6-(OCH₃)₃—C₆H₂ | — |
| 65 | OCH₃ | C₄H₉(C₂H₅)CH | H | H | 2-(CH₃)₂N-4-CH₃-pyridin-5-yl | — |
| 66 | OCH₃ | C₄H₉(C₂H₅)CH | H | CH₃ | 2,4-Cl₂—C₆H₃ | — |

TABLE 1-continued

| Ex No | $R^1$ | $R^2$ | $R^4$ | $R^5$ | $R^3$ | m.p. °C. |
|---|---|---|---|---|---|---|
| 67 | OCH$_3$ | C$_4$H$_9$(C$_2$H$_5$)CH | H | CH$_3$ | 2-Cl-4-CH$_3$O—C$_6$H$_3$ | — |
| 68 | OCH$_3$ | C$_4$H$_9$(C$_2$H$_5$)CH | H | CH$_3$ | 2,4,6-(CH$_3$)$_3$—C$_6$H$_2$ | — |
| 69 | OCH$_3$ | C$_4$H$_9$(C$_2$H$_5$)CH | H | CH$_3$ | 2,4,6-(OCH$_3$)$_3$—C$_6$H$_2$ | — |
| 70 | OCH$_3$ | C$_4$H$_9$(C$_2$H$_5$)CH | H | CH$_3$ | 2-(CH$_3$)$_2$N-4-CH$_3$-pyridin-5-yl | — |
| 71 | OCH$_3$ | C$_4$H$_9$(C$_2$H$_5$)CH | CH$_3$ | H | 2,4-Cl$_2$—C$_6$H$_3$ | — |
| 72 | OCH$_3$ | C$_4$H$_9$(C$_2$H$_5$)CH | CH$_3$ | H | 2-Cl-4-CH$_3$O—C$_6$H$_3$ | — |
| 73 | OCH$_3$ | C$_4$H$_9$(C$_2$H$_5$)CH | CH$_3$ | H | 2,4,6-(CH$_3$)$_3$—C$_6$H$_2$ | — |
| 74 | OCH$_3$ | C$_4$H$_9$(C$_2$H$_5$)CH | CH$_3$ | H | 2,4,6-(OCH$_3$)$_3$—C$_6$H$_2$ | — |
| 75 | OCH$_3$ | C$_4$H$_9$(C$_2$H$_5$)CH | CH$_3$ | H | 2-(CH$_3$)$_2$N-4-CH$_3$-pyridin-5-yl | — |
| 76 | OCH$_3$ | (C$_2$H$_5$)$_2$N | H | H | 2,4-Cl$_2$—C$_6$H$_3$ | — |
| 77 | OCH$_3$ | (C$_2$H$_5$)$_2$N | H | H | 2-Cl-4-CH$_3$O—C$_6$H$_3$ | — |
| 78 | OCH$_3$ | (C$_2$H$_5$)$_2$N | H | H | 2,4,6-(CH$_3$)$_3$—C$_6$H$_2$ | — |
| 79 | OCH$_3$ | (C$_2$H$_5$)$_2$N | H | H | 2,4,6-(OCH$_3$)$_3$—C$_6$H$_2$ | — |
| 80 | OCH$_3$ | (C$_2$H$_5$)$_2$N | H | H | 2-(CH$_3$)$_2$N-4-CH$_3$-pyridin-5-yl | — |
| 81 | OCH$_3$ | (C$_2$H$_5$)$_2$N | H | CH$_3$ | 2,4-Cl$_2$—C$_6$H$_3$ | — |
| 82 | OCH$_3$ | (C$_2$H$_5$)$_2$N | H | CH$_3$ | 2-Cl-4-CH$_3$O—C$_6$H$_3$ | — |
| 83 | OCH$_3$ | (C$_2$H$_5$)$_2$N | H | CH$_3$ | 2,4,6-(CH$_3$)$_3$—C$_6$H$_2$ | — |
| 84 | OCH$_3$ | (C$_2$H$_5$)$_2$N | H | CH$_3$ | 2,4,6-(OCH$_3$)$_3$—C$_6$H$_2$ | — |
| 85 | OCH$_3$ | (C$_2$H$_5$)$_2$N | H | CH$_3$ | 2-(CH$_3$)$_2$N-4-CH$_3$-pyridin-5-yl | — |
| 86 | OCH$_3$ | (C$_2$H$_5$)$_2$N | CH$_3$ | H | 2,4-Cl$_2$—C$_6$H$_3$ | — |
| 87 | OCH$_3$ | (C$_2$H$_5$)$_2$N | CH$_3$ | H | 2-Cl-4-CH$_3$O—C$_6$H$_3$ | — |
| 88 | OCH$_3$ | (C$_2$H$_5$)$_2$N | CH$_3$ | H | 2,4,6-(CH$_3$)$_3$—C$_6$H$_2$ | — |
| 89 | OCH$_3$ | (C$_2$H$_5$)$_2$N | CH$_3$ | H | 2,4,6-(OCH$_3$)$_3$—C$_6$H$_2$ | — |
| 90 | OCH$_3$ | (C$_2$H$_5$)$_2$N | CH$_3$ | H | 2-(CH$_3$)$_2$N-4-CH$_3$-pyridin-5-yl | — |
| 91 | CH$_3$ | (C$_2$H$_5$)$_2$CH | H | H | 2,4-Cl$_2$—C$_6$H$_3$ | — |
| 92 | OH | (C$_2$H$_5$)$_2$CH | H | CH$_3$ | 2,4-Cl$_2$—C$_6$H$_3$ | 227–228 |
| 93 | C$_2$H$_5$ | (C$_2$H$_5$)$_2$CH | OCH$_3$ | H | 2,4-Cl$_2$—C$_6$H$_3$ | — |
| 94 | C$_2$H$_5$ | (C$_2$H$_5$)$_2$CH | H | OCH$_3$ | 2,4-Cl$_2$—C$_6$H$_3$ | — |
| 95 | C$_2$H$_5$ | C$_3$H$_7$(CH$_3$)CH | H | H | 2,4-Cl$_2$—C$_6$H$_3$ | — |
| 96 | C$_2$H$_5$ | CH$_3$(c-C$_3$H$_5$)CH | H | H | 2,4-Cl$_2$—C$_6$H$_3$ | — |
| 97 | C$_2$H$_5$ | CH$_3$(c-C$_4$H$_7$)CH | H | H | 2,4-Cl$_2$—C$_6$H$_3$ | — |
| 98 | C$_2$H$_5$ | (c-C$_3$H$_5$)$_2$CH | H | H | 2,4-Cl$_2$—C$_6$H$_3$ | — |
| 99 | C$_2$H$_5$ | C$_2$H$_5$(c-C$_3$H$_5$)CH | H | H | 2,4-Cl$_2$—C$_6$H$_3$ | — |
| 100 | C$_2$H$_5$ | CH$_3$(c-C$_4$H$_7$)CH | H | H | 2,4-Cl$_2$—C$_6$H$_3$ | — |
| 101 | C$_2$H$_5$ | (HOCH$_2$)$_2$(CH$_3$)C | H | H | 2,4-Cl$_2$—C$_6$H$_3$ | — |
| 102 | C$_2$H$_5$ | (HOCH$_2$)$_2$(CH$_3$)C | H | H | 2-Cl-4-CH$_3$O—C$_6$H$_3$ | — |
| 103 | C$_2$H$_5$ | (HOCH$_2$)$_2$(CH$_3$)C | H | H | 2,4,6-(CH$_3$)$_3$—C$_6$H$_2$ | — |
| 104 | C$_2$H$_5$ | (HOCH$_2$)$_2$(CH$_3$)C | H | H | 2,4,6-(OCH$_3$)$_3$—C$_6$H$_2$ | — |
| 105 | C$_2$H$_5$ | (HOCH$_2$)$_2$(CH$_3$)C | H | H | 2-(CH$_3$)$_2$N-4-CH$_3$-pyridin-5-yl | — |
| 106 | C$_2$H$_5$ | (HOCH$_2$)$_2$(CH$_3$)C | H | H | 2,4-Cl$_2$-5-F—C$_6$H$_2$ | — |
| 107 | C$_2$H$_5$ | (HOCH$_2$)$_2$(CH$_3$)C | H | H | 2-Cl-4-OCH$_3$-5-F | — |
| 108 | C$_2$H$_5$ | (HOCH$_2$)$_2$(CH$_3$)C | H | H | 2-Cl-4,5-(OCH$_3$)$_2$ | — |
| 109 | C$_2$H$_5$ | (CH$_3$OCH$_2$)$_2$(CH$_3$)C | H | H | 2,4-Cl$_2$—C$_6$H$_3$ | — |
| 110 | C$_2$H$_5$ | (CH$_3$OCH$_2$)$_2$(CH$_3$)C | H | H | 2-Cl-4-CH$_3$O—C$_6$H$_3$ | — |
| 111 | C$_2$H$_5$ | (CH$_3$OCH$_2$)$_2$(CH$_3$)C | H | H | 2,4,6-(CH$_3$)$_3$—C$_6$H$_2$ | — |
| 112 | C$_2$H$_5$ | (CH$_3$OCH$_2$)$_2$(CH$_3$)C | H | H | 2,4,6-(OCH$_3$)$_3$—C$_6$H$_2$ | — |
| 113 | C$_2$H$_5$ | (CH$_3$OCH$_2$)$_2$(CH$_3$)C | H | H | 2-(CH$_3$)$_2$N-4-CH$_3$-pyridin-5-yl | — |
| 114 | C$_2$H$_5$ | (CH$_3$OCH$_2$)$_2$(CH$_3$)C | H | H | 2,4-Cl$_2$-5-F-C$_6$H$_2$ | — |
| 115 | C$_2$H$_5$ | (CH$_3$OCH$_2$)$_2$(CH$_3$)C | H | H | 2-Cl-4-OCH$_3$-5-F | — |
| 116 | C$_2$H$_5$ | (CH$_3$OCH$_2$)$_2$(CH$_3$)C | H | H | 2-Cl-4,5-(OCH$_3$)$_2$ | — |
| 117 | C$_2$H$_5$ | (H$_2$C=CH)$_2$(CH$_3$)C | H | H | 2,4-Cl$_2$—C$_6$H$_3$ | — |
| 118 | C$_2$H$_5$ | (H$_2$C=CH)$_2$(CH$_3$)C | H | H | 2-Cl-4-CH$_3$O—C$_6$H$_3$ | — |
| 119 | C$_2$H$_5$ | (H$_2$C=CH)$_2$(CH$_3$)C | H | H | 2,4,6-(CH$_3$)$_3$—C$_6$H$_2$ | — |
| 120 | C$_2$H$_5$ | (H$_2$C=CH)$_2$(CH$_3$)C | H | H | 2,4,6-(OCH$_3$)$_3$—C$_6$H$_2$ | — |
| 121 | C$_2$H$_5$ | (H$_2$C=CH)$_2$(CH$_3$)C | H | H | 2-(CH$_3$)$_2$N-4-CH$_3$-pyridin-5-yl | — |
| 122 | C$_2$H$_5$ | (H$_2$C=CH)$_2$(CH$_3$)C | H | H | 2,4-Cl$_2$-5-F-C$_6$H$_2$ | — |
| 123 | C$_2$H$_5$ | (H$_2$C=CH)$_2$(CH$_3$)C | H | H | 2-Cl-4-OCH$_3$-5-F | — |
| 124 | C$_2$H$_5$ | (H$_2$C=CH)$_2$(CH$_3$)C | H | H | 2-Cl-4,5-(OCH$_3$)$_2$ | — |
| 125 | C$_2$H$_5$ | (c-C$_3$H$_5$)$_2$(CH$_3$)C | H | H | 2,4-Cl$_2$—C$_6$H$_3$ | — |
| 126 | C$_2$H$_5$ | (c-C$_3$H$_5$)$_2$(CH$_3$)C | H | H | 2-Cl-4-CH$_3$O—C$_6$H$_3$ | — |
| 127 | C$_2$H$_5$ | (c-C$_3$H$_5$)$_2$(CH$_3$)C | H | H | 2,4,6-(CH$_3$)$_3$—C$_6$H$_2$ | — |
| 128 | C$_2$H$_5$ | (c-C$_3$H$_5$)$_2$(CH$_3$)C | H | H | 2,4,6-(OCH$_3$)$_3$—C$_6$H$_2$ | — |
| 129 | C$_2$H$_5$ | (c-C$_3$H$_5$)$_2$(CH$_3$)C | H | H | 2-(CH$_3$)$_2$N-4-CH$_3$-pyridin-5-yl | — |
| 130 | C$_2$H$_5$ | (c-C$_3$H$_5$)$_2$(CH$_3$)C | H | H | 2,4-Cl$_2$-5-F-C$_6$H$_2$ | — |
| 131 | C$_2$H$_5$ | (c-C$_3$H$_5$)$_2$(CH$_3$)C | H | H | 2-Cl-4-OCH$_3$-5-F | — |
| 132 | C$_2$H$_5$ | (c-C$_3$H$_5$)$_2$(CH$_3$)C | H | H | 2-Cl-4,5-(OCH$_3$)$_2$ | — |

TABLE 1-continued

| Ex No | R¹ | R² | R⁴ | R⁵ | R³ | m.p. ° C. |
|---|---|---|---|---|---|---|
| 133 | C₂H₅ | (C₂H₅)₂(OH)C | H | H | 2,4-Cl₂—C₆H₃ | — |
| 134 | C₂H₅ | (C₂H₅)₂(OH)C | H | H | 2-Cl-4-CH₃O—C₆H₃ | — |
| 135 | C₂H₅ | (C₂H₅)₂(OH)C | H | H | 2,4,6-(CH₃)₃—C₆H₂ | — |
| 136 | C₂H₅ | (C₂H₅)₂(OH)C | H | H | 2,4,6-(OCH₃)₃—C₆H₂ | — |
| 137 | C₂H₅ | (C₂H₅)₂(OH)C | H | H | 2-(CH₃)₂N-4-CH₃-pyridin-5-yl | — |
| 138 | C₂H₅ | (C₂H₅)₂(OH)C | H | H | 2,4-Cl₂-5-F-C₆H₂ | — |
| 139 | C₂H₅ | (C₂H₅)₂(OH)C | H | H | 2-Cl-4-OCH₃-5-F | — |
| 140 | C₂H₅ | (C₂H₅)₂(OH)C | H | H | 2-Cl-4,5-(OCH₃)₂ | — |
| 141 | C₂H₅ | C₂H₅(OCH₃)CH | H | H | 2,4-Cl₂—C₆H₃ | — |
| 142 | C₂H₅ | C₂H₅(OCH₃)CH | H | H | 2-Cl-4-CH₃O—C₆H₃ | — |
| 143 | C₂H₅ | C₂H₅(OCH₃)CH | H | H | 2,4,6-(CH₃)₃—C₆H₂ | — |
| 144 | C₂H₅ | C₂H₅(OCH₃)CH | H | H | 2,4,6-(OCH₃)₃—C₆H₂ | — |
| 145 | C₂H₅ | C₂H₅(OCH₃)CH | H | H | 2-(CH₃)₂N-4-CH₃-pyridin-5-yl | — |
| 146 | C₂H₅ | C₂H₅(OCH₃)CH | H | H | 2,4-Cl₂-5-F-C₆H₂ | — |
| 147 | C₂H₅ | C₂H₅(OCH₃)CH | H | H | 2-Cl-4-OCH₃-5-F | — |
| 148 | C₂H₅ | C₂H₅(OCH₃)CH | H | H | 2-Cl-4,5-(OCH₃)₂ | — |
| 149 | C₂H₅ | (C₂H₅)₂CH | H | H | 2,4-Cl₂-5-F-C₆H₂ | oil |
| 150 | C₂H₅ | (C₂H₅)₂CH | H | H | 2-Cl-4-OCH₃-5-F | — |
| 151 | C₂H₅ | (C₂H₅)₂CH | H | H | 2-Cl-4,5-(OCH₃)₂ | — |
| 152 | C₂H₅ | C₄H₉(C₂H₅)CH | H | H | 2,4-Cl₂-5-F-C₆H₂ | — |
| 153 | C₂H₅ | C₄H₉(C₂H₅)CH | H | H | 2-Cl-4-OCH₃-5-F | — |
| 154 | C₂H₅ | C₄H₉(C₂H₅)CH | H | H | 2-Cl-4,5-(OCH₃)₂ | — |
| 155 | OCH₃ | (C₂H₅)₂CH | H | H | 2,4-Cl₂-5-F—C₆H₂ | oil^g |
| 156 | OCH₃ | (C₂H₅)₂CH | H | H | 2-Cl-4-OCH₃-5-F | — |
| 157 | OCH₃ | (C₂H₅)₂CH | H | H | 2-Cl-4,5-(OCH₃)₂ | — |
| 158 | C₂H₅ | (C₂H₅)₂N | H | H | 2,4-Cl₂-5-F-C₆H₂ | — |
| 159 | C₂H₅ | (C₂H₅)₂N | H | H | 2-Cl-4-OCH₃-5-F | — |
| 160 | C₂H₅ | (C₂H₅)₂N | H | H | 2-Cl-4,5-(OCH₃)₂ | — |
| 161 | C₂H₅ | C₃H₇(CH₃)CH | H | H | 2-Cl-4-CH₃O—C₆H₃ | — |
| 162 | C₂H₅ | C₃H₇(CH₃)CH | H | H | 2,4,6-(CH₃)₃—C₆H₂ | — |
| 163 | C₂H₅ | C₃H₇(CH₃)CH | H | H | 2,4,6-(OCH₃)₃—C₆H₂ | — |
| 164 | C₂H₅ | C₃H₇(CH₃)CH | H | H | 2-(CH₃)₂N-4-CH₃-pyridin-5-yl | — |
| 165 | C₂H₅ | C₃H₇(CH₃)CH | H | H | 2,4-Cl₂-5-F-C₆H₂ | — |
| 166 | C₂H₅ | C₃H₇(CH₃)CH | H | H | 2-Cl-4-OCH₃-5-F | — |
| 167 | C₂H₅ | C₃H₇(CH₃)CH | H | H | 2-Cl-4,5-(OCH₃)₂ | — |
| 168 | C₂H₅ | (C₂H₅)₂CH | H | H | 2-CH₃-4-OCH₃-5-F—C₆H₂ | — |
| 169 | OCH₃ | (C₂H₅)₂CH | H | H | 2-CH₃-4-OCH₃-5-F—C₆H₂ | — |
| 170 | C₂H₅ | C₄H₉(C₂H₅)CH | H | H | 2-CH₃-4-OCH₃-5-F—C₆H₂ | — |
| 171 | OCH₃ | C₄H₉(C₂H₅)CH | H | H | 2-CH₃-4-OCH₃-5-F—C₆H₂ | — |
| 172 | C₂H₅ | (C₂H₅)₂N | H | H | 2-CH₃-4-OCH₃-5-F—C₆H₂ | — |
| 173 | OCH₃ | (C₂H₅)₂N | H | H | 2-CH₃-4-OCH₃-5-F—C₆H₂ | — |
| 174 | C₂H₅ | C₃H₇(CH₃)CH | H | H | 2-CH₃-4-OCH₃-5-F—C₆H₂ | — |
| 175 | OCH₃ | C₃H₇(CH₃)CH | H | H | 2-CH₃-4-OCH₃-5-F—C₆H₂ | — |
| 176 | C₂H₅ | C₂H₅(OCH₃)CH | H | H | 2-CH₃-4-OCH₃-5-F—C₆H₂ | — |
| 177 | OCH₃ | C₂H₅(OCH₃)CH | H | H | 2-CH₃-4-OCH₃-5-F—C₆H₂ | — |
| 178 | C₂H₅ | (C₂H₅)₂CH | H | H | 2-CH₃-4-OCH₃—C₆H₃ | — |
| 179 | OCH₃ | (C₂H₅)₂CH | H | H | 2-CH₃-4-OCH₃—C₆H₃ | — |
| 180 | C₂H₅ | C₄H₉(C₂H₅)CH | H | H | 2-CH₃-4-OCH₃—C₆H₃ | — |
| 181 | OCH₃ | C₄H₉(C₂H₅)CH | H | H | 2-CH₃-4-OCH₃—C₆H₃ | — |
| 182 | C₂H₅ | (C₂H₅)₂N | H | H | 2-CH₃-4-OCH₃—C₆H₃ | — |
| 183 | OCH₃ | (C₂H₅)₂N | H | H | 2-CH₃-4-OCH₃—C₆H₃ | — |
| 184 | C₂H₅ | C₃H₇(CH₃)CH | H | H | 2-CH₃-4-OCH₃—C₆H₃ | — |
| 185 | OCH₃ | C₃H₇(CH₃)CH | H | H | 2-CH₃-4-OCH₃—C₆H₃ | — |
| 186 | C₂H₅ | C₂H₅(OCH₃)CH | H | H | 2-CH₃-4-OCH₃—C₆H₃ | — |
| 187 | OCH₃ | C₂H₅(OCH₃)CH | H | H | 2-CH₃-4-OCH₃—C₆H₃ | — |
| 188 | C₂H₅ | (C₂H₅)₂CH | H | H | 2-CH₃-4-Cl—C₆H₃ | — |
| 189 | OCH₃ | (C₂H₅)₂CH | H | H | 2-CH₃-4-Cl—C₆H₃ | — |
| 190 | C₂H₅ | C₄H₉(C₂H₅)CH | H | H | 2-CH₃-4-Cl—C₆H₃ | — |
| 191 | OCH₃ | C₄H₉(C₂H₅)CH | H | H | 2-CH₃-4-Cl—C₆H₃ | — |
| 192 | C₂H₅ | (C₂H₅)₂N | H | H | 2-CH₃-4-Cl—C₆H₃ | — |
| 193 | OCH₃ | (C₂H₅)₂N | H | H | 2-CH₃-4-Cl—C₆H₃ | — |
| 194 | C₂H₅ | C₃H₇(CH₃)CH | H | H | 2-CH₃-4-Cl—C₆H₃ | — |
| 195 | OCH₃ | C₃H₇(CH₃)CH | H | H | 2-CH₃-4-Cl—C₆H₃ | — |
| 196 | C₂H₅ | C₂H₅(OCH₃)CH | H | H | 2-CH₃-4-Cl—C₆H₃ | — |
| 197 | OCH₃ | C₂H₅(OCH₃)CH | H | H | 2-CH₃-4-Cl—C₆H₃ | — |
| 198 | C₂H₅ | CH₃OCH₂(CH₃)CH | H | H | 2,4-Cl₂—C₆H₃ | oil^h |

TABLE 1-continued

| Ex No | R¹ | R² | R⁴ | R⁵ | R³ | m.p. ° C. |
|---|---|---|---|---|---|---|
| 199 | C₂H₅ | CH₃OCH₂(CH₃)CH | H | H | 2-Cl-4-CH₃O—C₆H₃ | — |
| 200 | C₂H₅ | CH₃OCH₂(CH₃)CH | H | H | 2,4,6-(CH₃)₃—C₆H₂ | — |
| 201 | C₂H₅ | CH₃OCH₂(CH₃)CH | H | H | 2,4,6-(OCH₃)₃—C₆H₂ | — |
| 202 | C₂H₅ | CH₃OCH₂(CH₃)CH | H | H | 2-(CH₃)₂N-4-CH₃-pyridin-5-yl | — |
| 203 | C₂H₅ | CH₃OCH₂(CH₃)CH | H | H | 2,4,6-(OCH₃)₃—C₆H₂ | — |
| 204 | C₂H₅ | CH₃OCH₂(CH₃)CH | H | H | 2,4-Cl₂-5-F—C₆H₂ | — |
| 205 | C₂H₅ | CH₃OCH₂(CH₃)CH | H | H | 2-Cl-4-OCH₃-5-F | — |
| 206 | C₂H₅ | CH₃OCH₂(CH₃)CH | H | H | 2-Cl-4,5-(OCH₃)₂ | — |
| 207 | C₂H₅ | CH₃OCH₂(CH₃)CH | H | H | 2-CH₃-4-OCH₃-5-F—C₆H₂ | — |
| 208 | C₂H₅ | CH₃OCH₂(CH₃)CH | H | H | 2-CH₃-4-OCH₃—C₆H₃ | — |
| 209 | C₂H₅ | CH₃OCH₂(CH₃)CH | H | H | 2-CH₃-4-Cl—C₆H₃ | — |
| 210 | OCH₃ | CH₃OCH₂(CH₃)CH | H | H | 2,4-Cl₂—C₆H₃ | — |
| 211 | OCH₃ | CH₃OCH₂(CH₃)CH | H | H | 2-Cl-4-CH₃O—C₆H₃ | — |
| 212 | OCH₃ | CH₃OCH₂(CH₃)CH | H | H | 2,4,6-(CH₃)₃—C₆H₂ | — |
| 213 | OCH₃ | CH₃OCH₂(CH₃)CH | H | H | 2,4,6-(OCH₃)₃—C₆H₂ | — |
| 214 | OCH₃ | CH₃OCH₂(CH₃)CH | H | H | 2-(CH₃)₂N-4-CH₃-pyridin-5-yl | — |
| 215 | OCH₃ | CH₃OCH₂(CH₃)CH | H | H | 2,4,6-(OCH₃)₃—C₆H₂ | — |
| 216 | OCH₃ | CH₃OCH₂(CH₃)CH | H | H | 2,4-Cl₂-5-F—C₆H₂ | — |
| 217 | OCH₃ | CH₃OCH₂(CH₃)CH | H | H | 2-Cl-4-OCH₃-5-F | — |
| 218 | OCH₃ | CH₃OCH₂(CH₃)CH | H | H | 2-Cl-4,5-(OCH₃)₂ | — |
| 219 | OCH₃ | CH₃OCH₂(CH₃)CH | H | H | 2-CH₃-4-OCH₃-5-F—C₆H₂ | — |
| 220 | OCH₃ | CH₃OCH₂(CH₃)CH | H | H | 2-CH₃-4-OCH₃—C₆H₃ | — |
| 221 | OCH₃ | CH₃OCH₂(CH₃)CH | H | H | 2-CH₃-4-Cl—C₆H₃ | — |
| 222 | C₂H₅ | C₂H₅OCH₂(CH₃)CH | H | H | 2,4-Cl₂—C₆H₃ | — |
| 223 | C₂H₅ | C₂H₅OCH₂(CH₃)CH | H | H | 2-Cl-4-CH₃O—C₆H₃ | — |
| 224 | C₂H₅ | C₂H₅OCH₂(CH₃)CH | H | H | 2,4,6-(CH₃)₃—C₆H₂ | — |
| 225 | C₂H₅ | C₂H₅OCH₂(CH₃)CH | H | H | 2,4,6-(OCH₃)₃—C₆H₂ | — |
| 226 | C₂H₅ | C₂H₅OCH₂(CH₃)CH | H | H | 2-(CH₃)₂N-4-CH₃-pyridin-5-yl | — |
| 227 | C₂H₅ | C₂H₅OCH₂(CH₃)CH | H | H | 2,4,6-(OCH₃)₃—C₆H₂ | — |
| 228 | C₂H₅ | C₂H₅OCH₂(CH₃)CH | H | H | 2,4-Cl₂-5-F—C₆H₂ | — |
| 229 | C₂H₅ | C₂H₅OCH₂(CH₃)CH | H | H | 2-Cl-4-OCH₃-5-F | — |
| 230 | C₂H₅ | C₂H₅OCH₂(CH₃)CH | H | H | 2-Cl-4,5-(OCH₃)₂ | — |
| 231 | C₂H₅ | C₂H₅OCH₂(CH₃)CH | H | H | 2-CH₃-4-OCH₃-5-F—C₆H₂ | — |
| 232 | C₂H₅ | C₂H₅OCH₂(CH₃)CH | H | H | 2-CH₃-4-OCH₃—C₆H₃ | — |
| 233 | C₂H₅ | C₂H₅OCH₂(CH₃)CH | H | H | 2-CH₃-4-Cl—C₆H₃ | — |
| 234 | OCH₃ | C₂H₅OCH₂(CH₃)CH | H | H | 2,4-Cl₂—C₆H₃ | — |
| 235 | OCH₃ | C₂H₅OCH₂(CH₃)CH | H | H | 2-Cl-4-CH₃O—C₆H₃ | — |
| 236 | OCH₃ | C₂H₅OCH₂(CH₃)CH | H | H | 2,4,6-(CH₃)₃—C₆H₂ | — |
| 237 | OCH₃ | C₂H₅OCH₂(CH₃)CH | H | H | 2,4,6-(OCH₃)₃—C₆H₂ | — |
| 238 | OCH₃ | C₂H₅OCH₂(CH₃)CH | H | H | 2-(CH₃)₂N-4-CH₃-pyridin-5-yl | — |
| 239 | OCH₃ | C₂H₅OCH₂(CH₃)CH | H | H | 2,4,6-(OCH₃)₃—C₆H₂ | — |
| 240 | OCH₃ | C₂H₅OCH₂(CH₃)CH | H | H | 2,4-Cl₂-5-F—C₆H₂ | — |
| 241 | OCH₃ | C₂H₅OCH₂(CH₃)CH | H | H | 2-Cl-4-OCH₃-5-F | — |
| 242 | OCH₃ | C₂H₅OCH₂(CH₃)CH | H | H | 2-Cl-4,5-(OCH₃)₂ | — |
| 243 | OCH₃ | C₂H₅OCH₂(CH₃)CH | H | H | 2-CH₃-4-OCH₃-5-F—C₆H₂ | — |
| 244 | OCH₃ | C₂H₅OCH₂(CH₃)CH | H | H | 2-CH₃-4-OCH₃—C₆H₃ | — |
| 245 | OCH₃ | C₂H₅OCH₂(CH₃)CH | H | H | 2-CH₃-4-Cl—C₆H₃ | — |
| 246 | C₂H₅ | CH₃OCH₂(C₂H₅)CH | H | H | 2,4-Cl₂—C₆H₃ | — |
| 247 | C₂H₅ | CH₃OCH₂(C₂H₅)CH | H | H | 2-Cl-4-CH₃O—C₆H₃ | — |
| 248 | C₂H₅ | CH₃OCH₂(C₂H₅)CH | H | H | 2,4,6-(CH₃)₃—C₆H₂ | — |
| 249 | C₂H₅ | CH₃OCH₂(C₂H₅)CH | H | H | 2,4,6-(OCH₃)₃—C₆H₂ | — |
| 250 | C₂H₅ | CH₃OCH₂(C₂H₅)CH | H | H | 2-(CH₃)₂N-4-CH₃-pyridin-5-yl | — |
| 251 | C₂H₅ | CH₃OCH₂(C₂H₅)CH | H | H | 2,4,6-(OCH₃)₃—C₆H₂ | — |
| 252 | C₂H₅ | CH₃OCH₂(C₂H₅)CH | H | H | 2,4-Cl₂-5-F—C₆H₂ | — |
| 253 | C₂H₅ | CH₃OCH₂(C₂H₅)CH | H | H | 2-Cl-4-OCH₃-5-F | — |
| 254 | C₂H₅ | CH₃OCH₂(C₂H₅)CH | H | H | 2-Cl-4,5-(OCH₃)₂ | — |
| 255 | C₂H₅ | CH₃OCH₂(C₂H₅)CH | H | H | 2-CH₃-4-OCH₃-5-F—C₆H₂ | — |
| 256 | C₂H₅ | CH₃OCH₂(C₂H₅)CH | H | H | 2-CH₃-4-OCH₃—C₆H₃ | — |
| 257 | C₂H₅ | CH₃OCH₂(C₂H₅)CH | H | H | 2-CH₃-4-Cl—C₆H₃ | — |
| 258 | OCH₃ | CH₃OCH₂(C₂H₅)CH | H | H | 2,4-Cl₂—C₆H₃ | — |
| 259 | OCH₃ | CH₃OCH₂(C₂H₅)CH | H | H | 2-Cl-4-CH₃O—C₆H₃ | — |
| 260 | OCH₃ | CH₃OCH₂(C₂H₅)CH | H | H | 2,4,6-(CH₃)₃—C₆H₂ | — |
| 261 | OCH₃ | CH₃OCH₂(C₂H₅)CH | H | H | 2,4,6-(OCH₃)₃—C₆H₂ | — |
| 262 | OCH₃ | CH₃OCH₂(C₂H₅)CH | H | H | 2-(CH₃)₂N-4-CH₃-pyridin-5-yl | — |
| 263 | OCH₃ | CH₃OCH₂(C₂H₅)CH | H | H | 2,4,6-(OCH₃)₃—C₆H₂ | — |
| 264 | OCH₃ | CH₃OCH₂(C₂H₅)CH | H | H | 2,4-Cl₂-5-F—C₆H₂ | — |

TABLE 1-continued

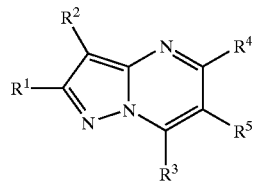

| Ex No | R¹ | R² | R⁴ | R⁵ | R³ | m.p. °C. |
|---|---|---|---|---|---|---|
| 265 | OCH₃ | CH₃OCH₂(C₂H₅)CH | H | H | 2-Cl-4-OCH₃-5-F | — |
| 266 | OCH₃ | CH₃OCH₂(C₂H₅)CH | H | H | 2-Cl-4,5-(OCH₃)₂ | — |
| 267 | OCH₃ | CH₃OCH₂(C₂H₅)CH | H | H | 2-CH₃-4-OCH₃-5-F—C₆H₂ | — |
| 268 | OCH₃ | CH₃OCH₂(C₂H₅)CH | H | H | 2-CH₃-4-OCH₃—C₆H₃ | — |
| 269 | OCH₃ | CH₃OCH₂(C₂H₅)CH | H | H | 2-CH₃-4-Cl—C₆H₃ | — |
| 270 | C₂H₅ | (C₂H₅)₂CH | H | H | 2-Cl-4-CF₃—C₆H₃ | oilⁱ |
| 271 | OCH₃ | (C₂H₅)₂CH | H | H | 2-Cl-4-CF₃—C₆H₃ | — |
| 272 | C₂H₅ | C₄H₉(C₂H₅)CH | H | H | 2-Cl-4-CF₃—C₆H₃ | — |
| 273 | OCH₃ | C₄H₉(C₂H₅)CH | H | H | 2-Cl-4-CF₃—C₆H₃ | — |
| 274 | C₂H₅ | (C₂H₅)₂N | H | H | 2-Cl-4-CF₃—C₆H₃ | — |
| 275 | OCH₃ | (C₂H₅)₂N | H | H | 2-Cl-4-CF₃—C₆H₃ | — |
| 276 | C₂H₅ | C₃H₇(CH₃)CH | H | H | 2-Cl-4-CF₃—C₆H₃ | — |
| 277 | OCH₃ | C₃H₇(CH₃)CH | H | H | 2-Cl-4-CF₃—C₆H₃ | — |
| 278 | C₂H₅ | C₂H₅(OCH₃)CH | H | H | 2-Cl-4-CF₃—C₆H₃ | — |
| 279 | OCH₃ | C₂H₅(OCH₃)CH | H | H | 2-Cl-4-CF₃—C₆H₃ | — |
| 280 | C₂H₅ | CH₃OCH₂(CH₃)CH | H | H | 2-Cl-4-CF₃—C₆H₃ | — |
| 281 | OCH₃ | CH₃OCH₂(CH₃)CH | H | H | 2-Cl-4-CF₃—C₆H₃ | — |

Key:

a) Spectral data for Example 1: ¹H NMR (300 MHz, CDCl₃): δ 8.38 (1H, d, J=4.1 Hz), 7.58 (1H, d, J=2.0 Hz), 7.55 (1H, d, J=8.2 Hz), 7.41 (1H, dd, J=8.2, 2.0 Hz), 6.65 (1H, d, J=4.1 Hz), 2.79 (2H, q, J=7.7 Hz), 2.78–2.68 (1H, m), 2.03–1.79 (4H, m), 1.25 (3H, t, J=7.7 Hz), 0.83 (6H, t, J=7.3 Hz). MS (NH₃—CI): m/e 367 (2), 366 (11), 365 (15), 364 (65), 363 (25), 362 (100). Analysis calc'd for C₁₉H₂₁Cl₂N₃: C, 62.99; H, 5.84; N, 11.60; found: C, 62.97; H, 5.74; N, 11.49.

b) Spectral data for Example 3: ¹H NMR (300 MHz, CDCl₃): δ 8.36 (1H, d, J=5.0 Hz), 7.00 (2H, s), 6.50 (1H, d, J=5.0 Hz), 2.77 (2H, q, J=7.7 Hz), 2.76–2.66 (1H, m), 2.36 (3H, s), 2.02 (6H, s), 2.00–1.80 (4H, m), 1.21 (3H, t, J=7.7 Hz), 0.83 (6H, t, J=7.5 Hz). MS (NH₃—CI): m/e 338 (3), 337 (24), 336 (100). Analysis calc'd for C₂₂H₂₉N₃: C, 78.76; H, 8.71; N, 12.53; found: C, 78.74; H, 8.74; N, 12.41.

c) Spectral data for Example 16: ¹H NMR (300 MHz, CDCl₃): δ 8.39 (1H, d, J=4.2 Hz), 7.59 (1H, d, J=8.3 Hz), 7.58 (1H, d, J=2.0 Hz), 7.42 (1H, dd, J=8.3, 2.0 Hz), 6.65 (1H, d, J=4.2 Hz), 2.82–2.72 (1H, m), 2.79 (2H, q, J=7.3 Hz), 2.00–1.77 (4H, m), 1.35–1.10 (4H, m), 1.25 (3H, t, J=7.3 Hz), 0.83 (3H, t, J=7.0 Hz), 0.82 (3H, t, J=7.5 Hz). MS (NH₃—CI): m/e calculated for C₂₁H₂₆Cl₂N₃: 390.1504, found 390.1502; 395 (3), 394 (12), 393 (17), 392 (67), 391 (29), 390 (100).

d) Spectral data for Example 18: ¹H NMR (300 MHz, CDCl₃): δ 8.36 (1H, d, J=4.0 Hz), 7.00 (2H, s), 6.50 (1H, d, J=4.0 Hz), 2.82–2.73 (1H, m), 2.77 (2H, q, J=7.6 Hz), 2.36 (3H, s), 2.02 (3H, s), 2.01 (3H, s), 2.00–1.78 (4H, m), 1.38–1.09 (4H, m), 1.20 (3H, t, J=7.6 Hz), 0.83 (3H, t, J=7.0 Hz), 0.81 (3H, t, J=7.3 Hz). MS (NH₃—CI): m/e calc'd for C₂₄H₃₄N₃: 364.2753, found 364.2754; 366 (4), 365 (27), 364 (100).

e) Spectral data for Example 31: ¹H NMR (300 MHz, CDCl₃): δ 8.38 (1H, d, J=4.0 Hz), 7.58 (1H, d, J=1.8 Hz), 7.56 (1H, d, J=8.4 Hz), 7.42 (1H, dd, J=8.4, 1.8 Hz), 6.65 (1H, d, J=4.0 Hz), 3.27 (4H, q, J=7.3 Hz), 2.80 (2H, q, J=7.3 Hz), 1.26 (3H, t, J=7.3 Hz), 1.00 (6H, t, J=7.3 Hz). MS (NH₃—CI): calculated for C₁₈H₂₁Cl₂N₄: 363.1143, found 363.1146; m/e 367 (6), 366 (14), 365 (81), 364 (28), 363 (100).

f) Spectral data for Example 51: ¹H NMR (300 MHz, CDCl₃): δ 8.27 (1H, s), 7.60 (1H, d, J=2.2 Hz), 7.43 (1H, dd, J=8.0, 2.0 Hz), 7.32 (1H, d, J=8.0 Hz), 3.84 (3H, s), 2.80–2.70 (1H, m), 2.08 (3H, s), 1.86–1.70 (4H, m), 0.82 (6H, t, J=7.4 Hz). MS (NH₃—CI): m/e 383 (2), 382 (12), 381 (14), 380 (65), 379 (25), 378 (100).

g) Spectral data for Example 155: ¹H NMR (300 MHz, CDCl₃): δ 8.39 (1H, d, J=4.0 Hz), 7.63 (1H, d, J=6.6 Hz), 7.48 (1H, d, J=8.8 Hz), 6.67 (1H, d, J=4.0 Hz), 2.79 (2H, q, J=7.4 Hz), 2.78–2.68 (1H, m), 2.03–1.79 (4H, m), 1.26 (3H, t, J=7.4 Hz), 0.83 (6H, t, J=7.5 Hz). MS (NH₃—CI): m/e 384 (11), 383 (16), 382 (79), 381 (20), 380 (100).

h) Spectral data for Example 198: ¹H NMR (300 MHz, CDCl₃): δ 8.40 (1H, d, J=4.0 Hz), 7.58 (1H, d, J=1.8 Hz), 7.55 (1H, d, J=8.4 Hz), 7.41 (1H, dd, J=8.4, 1.8 Hz), 6.67 (1H, d, J=4.0 Hz), 3.79 (2H, d, J=7.3 Hz), 3.38 (3H, s), 3.37 (1H, m), 2.82 (2H, q, J=7.3 Hz), 1.47 (3H, d, J=7.0 Hz), 1.25 (3H, t, J=7.3 Hz). Mass Spectrum (AP-CI): m/e 364 (100), 366 (65), 368 (12.5). High resolution mass spectrum: for C₁₈H₂OC₁₂N₃O m/e calculated: 364.0984, observed 364.0988.

i) Spectral data for Example 270: TLC $R_F$ 0.19 (5:95 ethyl acetate-hexane). ¹H NMR (300 MHz, CDCl₃): δ 8.42 (1H, d, J=4.4 Hz), 7.84 (1H, br s), 7.76 (1H, d, J=8.1 Hz), 7.69 (1H, d, J=8.1 Hz), 6.68 (1H, d, J=4.4 Hz), 2.79 (2H, q, J=7.7 Hz), 2.78–2.68 (1H, m), 2.02–1.80 (4H, m), 1.25 (3H, t, J=7.7 Hz), 0.84 (6H, t, J=7.5 Hz). MS (NH₃—CI): m/e 399 (7), 398 (33), 397 (25), 396 (100). Analysis calc'd for C₂₀H₂₁ClF₃N₃: C, 60.68; H, 5.36; N, 10.62; found: C, 60.66; H, 5.15; N, 10.48.

Additional Examples of Compounds Made According to the Above-Described Synthetic Scheme and Examples 7-(2,4-dichloro-5-fluorophenyl)-2-ethyl-3-(2-pentyl)-pyrazolo[1,5-a]pyrimidine
7-(2,4-dichlorophenyl)-2-ethyl-6-methyl-3-(2-pentyl)-pyrazolo[1,5-a]pyrimidine
7-(2-chloro-4-methoxyphenyl)-2-ethyl-3-(2-pentyl)pyrazolo[1,5-a]pyrimidine
2-ethyl-3-(2-pentyl)-7-(2,4,6-trimethylphenyl)-pyrazolo[1,5-a]pyrimidine
2-ethyl-3-(2-pentyl)-7-(2,4,6-trimethoxyphenyl)-pyrazolo[1,5-a]pyrimidine
7-(2,4-dichlorophenyl)-2-ethyl-3-(2-pentyl)pyrazolo[1,5-a]pyrimidine
7-(2,4-dichlorophenyl)-2-ethylpyrazolo[1,5-a]pyrimidine-3-carboxaldehyde
7-(2,4-dichlorophenyl)-2-ethyl-3-(1-hydroxyethyl)-pyrazolo[1,5-a]pyrimidine
7-(2,4-dichlorophenyl)-3-(1-ethoxyethyl)-2-ethyl-pyrazolo[1,5-a]pyrimidine
7-(2,4-dichlorophenyl)-3-(1-ethoxyethyl)-2-ethylpyrazolo[1,5-a]pyrimidine
2-ethyl-7-(2-methyl-4-methoxyphenyl)-3-(3-pentyl)-pyrazolo[1,5-a]pyrimidine
2-ethyl-7-(2-methyl-4-methoxyphenyl)-3-(2-pentyl)-pyrazolo[1,5-a]pyrimidine
7-(2,4-dimethylphenyl)-2-ethyl-3-(2-pentyl)-pyrazolo[1,5-a]pyrimidine
7-(2,4-dichlorophenyl)-2-ethyl-5-methylthio-3-(2-pentyl)-pyrazolo[1,5-a]pyrimidine
7-(2,4-dichlorophenyl)-2-ethyl-3-(6-methyl-5-hepten-2-yl)-pyrazolo[1,5-a]pyrimidine
7-(2,4-dichlorophenyl)-2-ethyl-3-(1-hydroxy-4-pentyl)-pyrazolo[1,5-a]pyrimidine
7-(4-difluoromethoxy-2-methyl)-2-ethyl-3-(3-pentyl)pyrazolo[1,5-a]pyrimidine
7-(4-difluoromethoxy-2-methyl)-2-ethyl-3-(2-pentyl)pyrazolo[1,5-a]pyrimidine
7-(2-chloro-4-difluoromethoxyphenyl)-2-ethyl-3-(3-pentyl)pyrazolo[1,5-a]pyrimidine
7-(2-chloro-4-difluoromethoxyphenyl)-2-ethyl-3-(2-pentyl)pyrazolo[1,5-a]pyrimidine
7-(2,4-dimethylphenyl)-2-ethyl-3-(3-pentyl)pyrazolo[1,5-a]pyrimidine
4-(7-(2,4-dichlorophenyl)-2-ethylpyrazolo[1,5-a]pyrimidinyl)pentanoic acid
4-(7-(2,4-dichlorophenyl)-2-ethylpyrazolo[1,5-a]pyrimidinyl)-N-methylpentanamide
3-(5-(benzoxazol-2-ylthio)-2-pentyl)-7-(2,4-dichlorophenyl)-2-ethylpyrazolo[1,5-a]pyrimidine
3-(5-(benzoxazolidinethione-3-yl)-2-pentyl)-7-(2,4-dichlorophenyl)-2-ethylpyrazolo[1,5-a]pyrimidine
7-(2,4-dichlorophenyl)-2-ethyl-3-(1-hydroxy-2-propyl)-pyrazolo[1,5-a]pyrimidine
7-(2,4-dichlorophenyl)-3-(1-ethoxy-2-propyl)-2-ethyl-pyrazolo[1,5-a]pyrimidine
3-(1-acetoxy-2-propyl)-7-(2,4-dichlorophenyl)-2-ethylpyrazolo[1,5-a]pyrimidine
3-(1-acetoxy-2-butyl)-7-(2,4-dichlorophenyl)-2-ethylpyrazolo[1,5-a]pyrimidine
7-(2,4-dichlorophenyl)-2-ethyl-3-(1-hydroxy-3-butyl)pyrazolo[1,5-a]pyrimidine
7-(2,4-dichlorophenyl)-2-ethyl-3-(1-methoxy-3-butyl)pyrazolo[1,5-a]pyrimidine
7-(2,4-dichlorophenyl)-2-ethyl-3-(3-heptyl)pyrazolo[1,5-a]pyrimidine
7-(2,4-dichlorophenyl)-2-ethyl-3-(3-heptyl)-6-methyl-pyrazolo[1,5-a]pyrimidine
2-ethyl-3-(3-heptyl)-7-(2,4,6-trimethylphenyl)-pyrazolo[1,5-a]pyrimidine
7-(2,4-dichlorophenyl)-2-ethyl-3-(3-pentyl)-pyrazolo[1,5-a]pyrimidine
7-(2,4-dichlorophenyl)-2-ethyl-3-(3-pentyl)-6-methyl-pyrazolo[1,5-a]pyrimidine
2-ethyl-3-(3-pentyl)-7-(2,4,6-trimethylphenyl)-pyrazolo[1,5-a]pyrimidine
2-ethyl-3-(3-pentyl)-7-(2,4,6-trimethoxyphenyl)-pyrazolo[1,5-a]pyrimidine Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:
1. A compound of formula I:

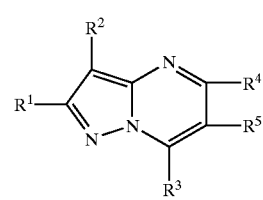

or a stereoisomer or pharmaceutically accetable salt thereof, wherein:

$R^1$ is selected from the group consisting of
$C_{1-6}$ alkyl,
$C_{2-10}$ alkenyl,
$C_{2-10}$ alkynyl,
$C_{3-6}$ cycloalkyl,
$C_{1-6}$ alkyloxy,
$C_{1-6}$ alkylS(O)$_n$,
—NR$^{1a}$R$^{1B}$ wherein $R^{1a}$ and $R^{1b}$ are independently selected from H, $C_{1-4}$ alkyl, —C(O)C$_{1-4}$alkyl,
—C(O)NR$^{1a}$R$^{1b}$,
—O—C(O)C$_{1-4}$alkyl,
—XR$^{1c}$ wherein $R^{1c}$ is selected from H or —C$_{1-4}$ alkylaryl, and X is selected from O or S(O)$_n$,
wherein $R^1$ is substituted with 0–6 substituents selected from halogen, $C_{1-4}$ alkyl, $C_{1-6}$ alkyloxy, $C_{1-4}$ haloalkyl, —NR$^{1a}$R$^{1b}$, and XR$^{1c}$;

$R^2$ is selected from the group consisting of
$C_{1-10}$ alkyl,
$C_{2-10}$ alkenyl,
$C_{2-10}$ alkynyl,
$C_{3-8}$ cycloalkyl,
$C_{3-6}$ cycloalkyl $C_{1-6}$ alkyl,
$C_{1-10}$ alkyloxy,
$C_{1-10}$ alkyloxyC$_{1-10}$ alkyl,
—SO$_2$—C$_{1-10}$alkyl
—SO$_2$R$^{2a}$ wherein $R^{2a}$ is aryl,
—SO$_2$R$^{2b}$ wherein $R^{2b}$ is heteroaryl,
—NR$^{2C}$R$^{2D}$ wherein $R^{2c}$ and $R^{2d}$ are independently selected from H, $C_{1-8}$ alkyl, S(O)$_n$C$_{1-4}$alkyl, C(O)

NR$^{2c}$R$^{2d}$, CO$_2$C$_{1-4}$alkyl, C$_{3-8}$ cycloalkyl, C$_{1-6}$ alkyloxyC$_{1-6}$ alkyl, —C(O)C$_{1-4}$alkyl or R$^{2c}$ and R$^{2d}$ may join to form a heterocyclic ring having 0–3 heteroatoms selected from O, N or S, -halogen, and —C(O)L wherein L is selected from C$_{1-6}$ alkyl, H, —OC$_{1-6}$ alkyl, O(CH$_2$)$_m$OC$_{1-6}$alkyl, O(CH$_2$)$_m$NR$^{2c}$R$^{2d}$, —OH, aryl, heteroaryl or C(O)OC$_{1-6}$ alkyl, wherein m is 1–3;

n is 0, 1 or 2;

R$^2$ is substituted with 0–3 substituents independently selected from R', R", R'" wherein R', R" and R'" are independently selected from C$_{1-6}$ alkyl, C$_{3-7}$ cycloalkyl, hydroxyC$_{1-6}$ alkyl, C$_{1-6}$ alkyloxyC$_{1-6}$ alkyl, C$_{2-6}$ alkenyl, C$_{1-6}$ alkyloxy, hydroxy; or R$^2$ is substituted with 0–3 substitutents independently selected from halogen,

—CN,

—S(O)$_n$R$^{2e}$ wherein R$^{2e}$ is selected from C$_{1-4}$ alkyl, C$_{1-4}$ haloalkyl, C$_{1-4}$ alkyloxy C$_{1-4}$ alkyl, C$_{3-6}$ cycloalkyl;

—COR$^{2f}$ wherein R$^{2f}$ is selected from H, C$_{1-4}$alkyl, C$_{1-4}$ haloalkyl, C$_{1-4}$ alkyloxy C$_{1-4}$ alkyl, C$_{3-6}$ cycloalkyl, and C$_{3-6}$ cycloalkylC$_{1-4}$ alkyl;

—CO$_2$R$^{2f}$,

—NR$^{2g}$COR$^{2f}$ wherein R$^{2g}$ is selected from H, C$_{1-6}$ alkyl, C$_{3-7}$ c-alkyl, C$_{3-6}$ cycloalkyl C$_{1-6}$ alkyl;

—N(COR$^{2f}$)$_2$,

—NR$^{2g}$CONR$^{2f}$R$^{2h}$ wherein R$^{2h}$ is selected from H, C$_{1-6}$ alkyl, C$_{1-4}$ haloalkyl, C$_{1-4}$ alkoxy C$_{1-4}$ alkyl, C$_{3-6}$ cycloalkyl and C$_{3-6}$ cycloalkylC$_{1-6}$ alkyl;

—NR$^{2g}$CO$_2$R$^{2e}$,

—CONR$^{2g}$R$^{2h}$, 1-morpholinyl, 1-piperidinyl, 1-piperazinyl, and

C$_{3-8}$ cycloalkyl wherein 0–1 carbon atoms in the C$_{4-8}$ cycloalkyl is replaced by a group selected from —O—, —S(O)$_n$—, —NR$^{2g}$—, —NCO$_2$R$^{2e}$, —NCOR$^{2e}$, and —NSO$_2$R$^{2e}$; and wherein N$_4$ in 1-piperazinyl is substituted with 0–1 substituents selected from R$^{2g}$, CO$_2$R$^{2e}$, COR$^{2e}$ and SO$_2$R$^{2e}$; or R$^2$ is substituted with the group R$^{2i}$, R$^{2j}$, R$^{2k}$, C$_{1-6}$ alkyl, C$_{2-8}$ alkenyl, C$_{2-8}$ alkynyl, Br, Cl, F, I, C$_{1-4}$ haloalkyl, —OR$^{2g}$, —NR$^{2g}$R$^{2h}$, —C$_{1-6}$ alkylOR$^{2g}$, and C$_{3-8}$ cycloalkyl which is substituted with 0–1 R$^{2l}$ and in wich 0–1 carbons of C$_{4-8}$ cycloalkyl is replaced by —O—, wherein R$^{2i}$ is selected from aryl wherein aryl includes phenyl, naphthyl, indanyl and indenyl, each R$^{2i}$ being substituted with 0–1 OR$^{2m}$ and 0–5 substituents independently selected from the group C$_{1-6}$ alkyl, C$_{3-6}$ cycloalkyl, Br, Cl, F, I, C$_{1-4}$ haloalkyl, —CN, nitro, —SH, —S(O)$_n$R$^{2n}$, —COR$^{2m}$, —OC(O)R$^{2n}$, —NR$^{2g}$COR$^{2m}$, N(COR$^{2m}$)$_2$, —NR$^{2g}$CONR$^{2o}$R$^{2p}$, —NR$^{2g}$CO$_2$R$^{2n}$, —NR$^{2o}$R$^{2p}$ and —CONR$^{2o}$R$^{2p}$;

R$^{2j}$ is selected from heteroaryl wherein heteroaryl includes pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-s-oxide, 2,3-dihydro-benzothienyl-S-dioxide, indolinyl, benzoxazolin-2-onyl, benzodioxolanyl and benzodioxane, each heteroaryl being substituted on 0–4 carbon atoms with a substituent independently selected from the group C$_{1-6}$ alkyl, C$_{3-6}$ cycloalkyl, Br, Cl, F, I, C$_{1-4}$ haloalkyl, —CN, nitro, OR$^{2m}$, —SH, —S(O)$_n$R$^{2h}$, —COR$^{2m}$, —OC(O)R$^{2h}$, —NR$^{2g}$COR$^{2m}$, —N(COR$^{2m}$)$_2$, —NR$^{2g}$CONR$^{2o}$R$^{2p}$, —NR$^{2g}$CO$_2$R$^{2h}$, —NR$^{2o}$R$^{2p}$ and —CONR$^{2o}$R$^{2p}$ and each heteroaryl being substituted on any nitrogen atom with 0–1 substituents selected from the group R$^{2g}$, CO$_2$R$^{2e}$, COR$^{2e}$ and SO$_2$R$^{2e}$;

R$^{2k}$ is heterocyclyl which is a saturated or partially saturated heteroaryl as defined for R$^{2j}$, each heterocyclyl being substituted on 0–4 carbon atoms with a substituent independently selected from the group C$_{1-6}$ alkyl, C$_{3-6}$ cycloalkyl, Br, Cl, F, I, C$_{1-4}$ haloalkyl, —CN, nitro, —OR$^{2m}$, —SH, —S(O)$_n$R$^{2h}$, —COR$^{2m}$, —OC(O)R$^{2h}$, —NR$^{2g}$COR$^{2m}$, —N(COR$^{2m}$)$_2$, —NR$^{2g}$CONR$^{2o}$R$^{2p}$, NR$^{2g}$CO$_2$R$^{2h}$, —NR$^{2o}$R$^{2p}$ and —CONR$^{2o}$R$^{2p}$ and each heterocyclyl being substituted on any nitrogen atom with 0–1 substituents selected from the group R$^{2f}$, CO$_2$R$^{2e}$, COR$^{2e}$ and SO$_2$R$^{2e}$;

wherein

R$^{2l}$ is H, C$_{1-4}$ alkyl, C$_{3-6}$ cycloalky-C$_{1-4}$ alkyl and C$_{3-8}$ cycloalkyl;

R$^{2m}$ is H, C$_{1-6}$ alkyl, C$_{3-6}$ cycloalkyl C$_{1-6}$ alkyl, C$_{1-2}$ alkyloxy C$_{1-2}$ alkyl, C$_{1-4}$ haloalkyl, R$^{2q}$S(O)$_n$—C$_{1-4}$ alkyl or R$^{2r}$R$^{2s}$N—C$_{2-4}$ alkyl;

R$^{2n}$ is H, C$_{1-6}$ alkyl, C$_{3-10}$ cyloalkyl, C$_{3-6}$ cycloalkyl-C$_{1-6}$ alkyl, C$_{1-2}$ alkyloxy C$_{1-2}$ alkyl, and C$_{1-4}$ haloalkyl;

R$^{2o}$ and R$^{2p}$ are independently selected at each occurrence from H, C$_{1-6}$ alkyl, C$_{3-10}$ cycloalkyl, C$_{3-6}$ cycloalkyl C$_{1-6}$ alkyl and C$_{1-4}$ haloalkyl;

R$^{2q}$ is selected from C$_{1-6}$ alkyl, C$_{1-4}$ haloalkyl, C$_{1-4}$ alkoxy-C$_{1-4}$ alkyl, C$_{3-6}$ cycloalkyl, C$_{3-6}$ cycloalkyl-C$_{1-6}$ alkyl, aryl, aryl(C$_{1-4}$ alkyl), heteroaryl and heteroaryl (C$_{1-4}$ alkyl)- and benzyl, each benzyl being substituted on the aryl moiety with 0–1 substituents selected from the group C$_{1-4}$ alkyl, Br, Cl, F, I, C$_{1-4}$ haloalkyl, nitro, C$_{1-4}$ alkoxy C$_{1-4}$ haloalkoxy, and dimethylamino;

R$^{2r}$R$^{2s}$ taken together with the N form 1-pyrrolidinyl, 1-morpholinyl, 1-piperidinyl or 1-piperazinyl wherein N$_4$ in 1-piperiazinyl is substituted with 0–1 substituents selected from the group R$^{2t}$, CO$_2$R$^{2q}$, COR$^{2q}$ and SO$_2$R$^{2q}$;

R$^{2t}$ is selected from H, C$_{1-4}$ alkyl, C$_{1-4}$ haloalkyl, C$_{1-4}$ alkoxy-C$_{1-4}$ alkyl, C$_{3-6}$ cycloalkyl, C$_{3-6}$ cycloalkyl-C$_{1-6}$ alkyl, aryl, aryl (C$_{1-4}$ alkyl)-, heteroaryl and heteroaryl (C$_{1-4}$ alkyl);

R$^3$ is an aryl or heteroaryl group attached through an unsaturated carbon atom of the heteroaryl group;

aryl is selected from phenyl, naphthyl, indanyl and indenyl, each aryl being substituted with 0–5 substituents independently selected at each occurrence from C$_{1-6}$ alkyl, C$_{3-6}$ cycloalkyl, methylenedioxy, C$_{1-4}$ alkyloxy-C$_{1-4}$ alkyloxy, —OR$^{2m}$, Br, Cl, F, I, C$_{1-4}$ haloalkyl, —CN, —NO$_2$, —SH, —S(O)$_n$R$^{2n}$, —COR$^{2m}$, —CO$_2$R$^{2m}$, —OC(O)R$^{2n}$, —NR$^{2g}$COR$^{2m}$, —N(COR$^{2m}$)$_2$, —NR$^{2g}$CONR$^{2o}$R$^{2p}$, —NR$^{2g}$CO$_2$R$^{2h}$, —NR$^{2o}$R$^{2p}$ and CONR$^{2o}$R$^{2p}$ and up to 1 phenyl, each phenyl substituent being substituted with 0–4 substituents selected from the group C$_{1-3}$ alkyl, C$_{1-3}$ alkoxy, Br, Cl, F, I, —CN, dimethylamino, $CF_3$, $C_2F_5$, $OCF_3$, $SO_2Me$ and acetyl;

heteroaryl is selected from the group pyridyl, pyrimidyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzo-furanyl, 2,3-dihydrobenzothienyl, 2,3-dihydro-benzothienyl-S-oxide, 2,3-dihydrobenzothienyl-s-dioxide, indolinyl, benzoxazolin-2-on-yl, benzodioxolanyl and benzodioxane, each heteroaryl being substitued at 0–4 carbon atoms with a substituent independently selected at each occurrence from the group $C_{1-6}$ alkyl, $C_{3-6}$ cycloalkyl, Br, F, I, $C_{1-4}$ haloalkyl, —CN, $NR^{2g}R^{2h}$, nitro, —$OR^{2m}$, —SH, —$S(O)_nR^{2n}$, $COR^{2m}$, —$CO_2R^{2m}$, —$OC(O)R^{2n}$, —$NR^{2g}COR^{2m}$, —$N(COR^{2m})_2$, —$NR^{2g}CONR^{2o}R^{2p}$ and each heteroaryl being substituted at any nitrogen atom with 0–1 substituents selected from the group $R^{2g}$, $CO_2R^{3a}$, $COR^{3a}$ and $SO_2R^{3a}$ wherein, $R^{3a}$ is selected from the group $C_{1-6}$ alkyl, $C_{1-4}$ cycloalkyl-$C_{1-6}$ alkyl and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^4$ and $R^5$ are independently selected at each occurrence from H, Br, Cl, F, I, —CN, $C_{1-6}$ alkyl, $C_{2-6}$ alkenyl, $C_{2-6}$ alkynyl, $C_{3-8}$ cycloalkyl, $C_{1-6}$ alkyloxy, $C_{1-6}$ alkylthio, $C_{1-6}$ alkylsulfinyl, $C_{1-6}$ alkylsulfonyl, amino, $C_{1-4}$ alkylamino, $(C_{1-4}$ alkyl$)_2$ amino and phenyl, each phenyl is substituted with 0–3 groups selected from the group consisting of $C_{1-7}$ alkyl, $C_{3-8}$ cycloalkyl, Br, Cl, F, I, —C(O)H, $C_{1-4}$ haloalkyl, nitro, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, $C_{1-6}$ alkylamino and $(C_{1-4}$ alkyl$)_2$ amino and wherein $R^4$ and $R^5$ non-phenyl groups may be substituted with 0–5 substituents selected from OH, halogen, —C(O)H, —$OC_{1-6}$-alkyl and $C_{1-6}$ haloalkyl, $C_{1-6}$ alkyl, and $C_{3-7}$ c-alkyl;

with the proviso that the compounds of Formula I with $R^1$, $R^2$, $R^3$, $R^4$ and $R^5$ as specifically defined below are excluded:

(a) a compound of formula I wherein $R^1$ is unsubstituted, unbranched (linear) $C_{1-3}$ alkyl and $R^2$ is —C(O)-Ph;

(b) a compound of formula I, wherein $R^5$ is H or $C_{1-3}$ alkyl and $R^3$ is pyridyl, pyridyl-N-oxide, thien-3-yl or furan-3-yl or $C_{1-3}$ alkyl substituted versions thereof and $R^1$ is carboamoyl or unsubstituted, unbranched $C_{1-3}$ alkyl, $R^2$ is F, Cl, Br, formyl, carboxyl, hydroxymethyl, unsubstituted, unbranched $C_{1-3}$ alkyl, —C(O)R, —C(O)OR, —$CH_2OR$, —$C(O)O(CH_2)_2OR$, —C(O)O$(CH_2)_2NHR$, or —$C(O)O(CH_2)_2NR^2$ wherein R is $C_{1-3}$ alkyl;

(c) a compound of formula I, wherein $R^1$ is unsubstituted, unbranched $C_{1-3}$ alkyl and $R^2$ is halogen, or —C(O)R wherein R is H, $C_{1-3}$ alkyl or $C_{1-4}$ alkoxy, $R^3$ is Ph substituted with $NR^{2g}C(O)R^{2m}$;

(d) a compound of formula I, $R^2$ is halogen, $CO_2R$ with R equal to $C_{1-3}$ alkyl, unsubstituted, unbranched $C_{1-3}$ alkyl, $C_{1-3}$ haloalkyl or $CONH_2$ and $R^1$ is equal to OR, SR wherein R is $C_{1-3}$ alkyl, $C_{1-4}$ haloalkyl or $C_{3-4}$ halocycloalkyl, and $R^3$ is phenyl or substituted phenyl;

(e) a compound of formula I, wherein $R^5$ is H or $C_{1-3}$ alkyl; $R^3$ is phenyl, ortho-trifluoromethylphenyl, meta-trifluorophenyl or meta-methoxyphenyl; $R^1$ is carbam-oyl or unsubstituted, unbranched $C_{1-3}$ alkyl; $R^2$ is halogen, formyl, carboxyl, cyano, hydroxymethyl, unsubstituted, unbranched $C_{1-3}$ alkyl, —C(O)R, —C(O)OR, $CH_2OR$, —$C(O)O(CH_2)_2OR$, —C(O)O$(CH_2)_2NHR$ or —$C(O)O(CH_2)_2NR^2$ wherein R is $C_{1-3}$ alkyl;

(f) in a compound of formula I, $R^2$ is C(O)OEt, $R^1$ is $SCH_3$, $R^3$ is Ph, $R^4$ is $SCH_3$ (or Ph) and $R^5$ is H;

(g) in a compound of formula I, $R^1$ is $N(C(O)CH_3)_2$, $R^2$ is $CH_2Ph$(p-Me, p-Cl), $R^3$ is Ph (p-ClPh), $R^4$ is $SCH_3$ and $R^5$ is H;

(h) in a compound of formula I, $R^1$ is $N(C(O)CH_3)_2$, $R^2$ is $CH_2Ph$(p-OMe), $R^3$ is p-ClPh, $R^4$ is $SCH_3$ and $R^5$ is H;

(i) in a compound of formula I, $R^2$ is $CH_3$, $R^1$ is $CH_3$, $R^3$ is p-F-Ph, $R^4$ is c-propyl and $R^5$ is —$CH_2OH$;

(j) in a compound of formula I, $R^2$ is $CH_3$, $R^1$ is $CH_3$, $R^3$ is p-F-Ph, $R^4$ is c-propyl and $R^5$ is —C(O)H;

(k) in a compound of formula I, $R^2$ is $CH_3$, $R^1$ is $CH_3$, $R^3$ is p-F-Ph, $R^4$ is c-propyl and $R^5$ is —CH=CH—C(O)H;

(l) in a compound of formula I, $R^2$ is C(O)OMe, $R^1$ is —$SCH_2$-Ph, $R^3$ is Ph, $R^4$ is Me and $R^5$ is H;

(m) in a compound of formula I, $R^2$ is C(O)OMe, $R^1$ is —$SCH_2$-Ph, $R^3$ is Ph, $R^4$ is H and $R^5$ is H;

(n) in a compound of formula I, $R^2$ is C(O)Ph, $R^1$ is Me, $R^3$ is pyrid-4-yl, $R^4$ and $R^5$ are H;

(o) in a compound of formula I, $R^2$ is C(O)Ph, $R^1$ is Me, $R^3$ is m-$CF_3$-Ph, $R^4$ and $R^5$ are H;

(p) in a compound of formula I, $R^2$ is C(O)Ph, $R^1$ is Me, $R^3$ is pyrid-3-yl, $R^4$ and $R^5$ are H;

(q) in a compound of formula I, $R^2$ is Cl, $R^1$ is Et, $R^3$ is pyrid-3-yl, $R^4$ and $R^5$ are H;

(r) in a compound of formula I, $R^2$ is $CO_2H$, $R^1$ is Et, $R^3$ is pyrid-3-yl, $R^4$ and $R^5$ are H;

(s) in a compound of formula I, $R^2$ is $CO_2H$, $R^1$ is $CH_3$, $R^3$ is pyrid-3-yl, $R^4$ and $R^5$ are H and H Cl salt;

(t) in a compound of formula I, $R^2$ is C(O)OEt, $R^1$ is $CH_3$, $R^3$ is pyrid-3-yl, $R^4$ and $R^5$ are H;

(u) in a compound of formula I, $R^2$ is C(O)OEt, $R^1$ is Et, $R^3$ is pyrid-3-yl, $R^4$ and $R^5$ are H;

(v) in a compound of formula I, $R^2$ is C(O)OMe, $R^1$ is Me, $R^3$ is m-$CF_3$-Ph, $R^4$ and $R^5$ are H;

(w) in a compound of formula I, $R^2$ is C(O)OEt, $R^1$ is Et, $R^3$ is Ph, $R^4$ and $R^5$ are H;

(x) in a compound of formula I, $R^2$ is C(O)OEt, $R^1$ is Et, $R^3$ is m-$CF_3$-Ph, $R^4$ and $R^5$ are H.

2. A compound of formula I:

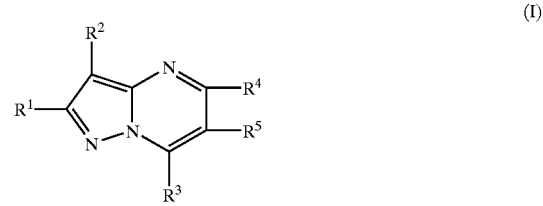

(I)

or a stereoisomer or pharmaceutically acceptable salt thereof, wherein:

$R^1$ is selected from the group consisting of $C_{1-6}$ alkyl, $C_{2-10}$ alkenyl, $C_{2-10}$ alkynyl,
$C_{3-6}$ cycloalkyl,
$C_{1-6}$ alkyloxy,
$C_{1-6}$ alkylS(O)$_n$,
—NR$^{1a}$R$^{1B}$ wherein R$^{1a}$ and R$^{1b}$ are independently selected from H, $C_{1-4}$ alkyl, —C(O)C$_{1-4}$alkyl,
—C(O)NR$^{1a}$R$^{1b}$,
—O—C(O)C$_{1-4}$alkyl,
—XR$^{1c}$ wherein R$^{1c}$ is selected from H or —C$_{1-4}$ alkylaryl, and X is selected from O or S(O)$_n$,
wherein R$^1$ is substituted with 0–6 substituents selected from halogen, $C_{1-4}$ alkyl, $C_{1-6}$ alkyloxy, $C_{1-4}$ haloalkyl, —NR$^{1a}$R$^{1b}$, and —XR$^{1c}$;
R$^2$ is selected from the group consisting of
$C_{1-10}$ alkyl excluding unsubstituted, unbranched $C_{1-3}$alkyl,
$C_{2-10}$ alkenyl,
$C_{2-10}$ alkynyl,
$C_{3-8}$ cycloalkyl,
$C_{3-6}$ cycloalkyl $C_{1-6}$ alkyl,
$C_{1-10}$ alkyloxy,
$C_{1-10}$ alkyloxy$C_{1-10}$ alkyl,
$C_{1-4}$ alkoxy $C_{1-4}$ alkyl,
—SO$_2$—C$_{1-10}$alkyl
—SO$_2$R$^{2a}$ wherein R$^{2a}$ is aryl,
—SO$_2$R$^{2b}$ wherein R$^{2b}$ is heteroaryl,
—NR$^{2C}$R$^{2D}$ wherein R$^{2c}$ and R$^{2d}$ are independently selected from H, $C_{1-8}$ alkyl, S(O)$_n$C$_{1-4}$ alkyl, C(O)NR$^{2c}$R$^{2d}$, CO$_2$C$_{1-4}$alkyl, $C_{3-8}$ cycloalkyl, $C_{1-6}$ alkyloxyC$_{1-6}$ alkyl, —C(O)C$_{1-4}$alkyl or R$^{2c}$ and R$^{2d}$ may join to form a heterocyclic ring having 0–3 heteroatoms selected from O, N or S,
n is 0, 1 or 2;
R$^2$ is substituted with 0–3 substituents independently selected from R', R", R''' wherein R', R" and R''' are independently selected from $C_{1-6}$ alkyl, $C_{3-7}$ cycloalkyl, hydroxyC$_{1-6}$ alkyl, $C_{1-6}$ alkyloxyC$_{1-6}$ alkyl, $C_{2-6}$ alkenyl, $C_{1-6}$ alkyloxy, and hydroxy, or
R$^2$ is substituted with 0–3 substituents independently selected from:
—CN,
—S(O)$_n$R$^{2e}$ wherein R$^{2e}$ is selected from $C_{1-4}$ alkyl, $C_{1-4}$ haloalkyl, $C_{1-4}$ alkyloxy $C_{1-4}$ alkyl, $C_{3-6}$ cycloalkyl;
—COR$^{2f}$ wherein R$^{2f}$ is selected from H, $C_{1-4}$ alkyl, $C_{1-4}$ haloalkyl, $C_{1-4}$ alkyloxy $C_{1-4}$ alkyl, $C_{3-6}$ cycloalkyl, and $C_{3-6}$ cycloalkylC$_{1-4}$ alkyl;
—CO$_2$R$^{2f}$,
—NR$^{2g}$COR$^{2f}$ wherein R$^{2g}$ is selected from H, $C_{1-6}$ alkyl, $C_{3-7}$ c-alkyl, $C_{3-6}$ cycloalkyl $C_{1-6}$ alkyl;
—N(COR$^{2f}$)$_2$,
—NR$^{2g}$CONR$^{2f}$R$^{2h}$, wherein R$^{2h}$ is selected from H, $C_{1-6}$ alkyl, $C_{1-4}$ haloalkyl, $C_{1-4}$ alkoxy $C_{1-4}$ alkyl, $C_{3-6}$ cycloalkyl and $C_{3-6}$ cycloalkylC$_{1-6}$ alkyl;
—NR$^{2g}$CO$_2$R$^{2e}$,
—CONR$^{2g}$R$^{2h}$,
1-morpholinyl,
1-piperidinyl,
1-piperazinyl, and
$C_{3-8}$ cycloalkyl wherein 0–1 carbon atoms in the $C_{4-8}$ cycloalkyl is replaced by a group selected from —O—, —S(O)$_n$—, —NR$^{2g}$—, —NCO$_2$R$^{2e}$, —NCOR$^{2e}$, and —NSO$_2$R$^{2e}$; and
wherein N$_4$ in 1-piperazinyl is substituted with 0–1 substituents selected from R$^{2g}$, CO$_2$R$^{2e}$, COR$^{2e}$ and SO$_2$R$^{2e}$; or
R$^2$ is substituted with the group R$^{2j}$, R$^{2k}$, $C_{1-6}$ alkyl, $C_{2-8}$ alkenyl, $C_{2-8}$ alkynyl, Br, Cl, F, I, $C_{1-4}$ haloalkyl, —OR$^{2g}$, —NR$^{2g}$R$^{2h}$, —C$_{1-6}$ alkylOR$^{2g}$, and $C_{3-8}$ cycloalkyl which is substituted with 0–1 R$^{2l}$ and in which 0–1 carbons of $C_{4-8}$ cycloalkyl is replaced by —O—, wherein
R$^{2j}$ is selected from heteroaryl wherein heteroaryl includes pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-s-oxide, 2,3-dihydro-benzothienyl-S-dioxide, indolinyl, benzoxazolin-2-onyl, benzodioxolanyl and benzodioxane, each heteroaryl being substituted on 0–4 carbon atoms with a substituent independently selected from the group $C_{1-6}$ alkyl, $C_{3-6}$ cycloalkyl, Br, Cl, F, I, $C_{1-4}$ haloalkyl, —CN, nitro, OR$^{2m}$, —SH, —S(O)$_n$R$^{2h}$, —COR$^{2m}$, —OC(O)R$^{2h}$, —NR$^{2g}$COR$^{2m}$, —N(COR$^{2m}$)$_2$, —NR$^{2g}$CONR$^{2o}$R$^{2p}$, —NR$^{2g}$CO$_2$R$^{2h}$, —NR$^{2o}$R$^{2p}$ and —CONR$^{2o}$R$^{2p}$ and each heteroaryl being substituted on any nitrogen atom with 0–1 substituents selected from the group R$^{2g}$, CO$_2$R$^{2e}$, COR$^{2e}$ and SO$_2$R$^{2e}$;
R$^{2k}$ is heterocyclyl which is a saturated or partially saturated heteroaryl as defined for R$^{2j}$, each heterocyclyl being substituted on 0–4 carbon atoms with a substituent independently selected from the group $C_{1-6}$ alkyl, $C_{3-6}$ cycloalkyl, Br, Cl, F, I, $C_{1-4}$ haloalkyl, —CN, nitro, —OR$^{2m}$, —SH, —S(O)$_n$R$^{2h}$, —COR$^{2m}$, —OC(O)R$^{2h}$, —NR$^{2g}$COR$^{2m}$, —N(COR$^{2m}$)$_2$, —NR$^{2g}$CONR$^{2o}$R$^{2p}$, NR$^{2g}$CO$_2$R$^{2h}$, —NR$^{2o}$R$^{2p}$ and —CONR$^{2o}$R$^{2p}$ and each heterocyclyl being substituted on any nitrogen atom with 0–1 substituents selected from the group R$^{2f}$, CO$_2$R$^{2e}$, COR$^{2e}$ and SO$_2$R$^{2e}$;
wherein
R$^{2l}$ is H, $C_{1-4}$ alkyl, $C_{3-6}$ cycloalky-$C_{1-4}$ alkyl and $C_{3-8}$ cycloalkyl;
R$^{2m}$ is H, $C_{1-6}$ alkyl, $C_{3-6}$ cycloalkyl $C_{1-6}$ alkyl, $C_{1-2}$ alkyloxy $C_{1-2}$ alkyl, $C_{1-4}$ haloalkyl, R$^{2q}$S(O)$_n$—$C_{1-4}$ alkyl and R$^{2r}$R$^{2s}$N—C$_{2-4}$ alkyl;
R$^{2n}$ is H, $C_{1-6}$ alkyl, $C_{3-10}$ cyloalkyl, $C_{3-6}$ cycloalkyl $C_{1-6}$ alkyl, $C_{1-2}$ alkyloxy $C_{1-2}$ alkyl, and $C_{1-4}$ haloalkyl;
R$^{2o}$ and R$^{2p}$ are independently selected at each occurrence from H, $C_{1-6}$ alkyl, $C_{3-10}$ cycloalkyl, $C_{3-6}$ cycloalkyl $C_{1-6}$ alkyl and $C_{1-4}$ haloalkyl;
R$^{2q}$ is selected from $C_{1-6}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl), heteroaryl and heleroaryl ($C_{1-4}$ alkyl)- and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy $C_{1-4}$ haloalkoxy, and dimethylamino;
R$^{2r}$R$^{2s}$ taken together with the N form 1-pyrrolidinyl, 1-morpholinyl, 1-piperidinyl or 1-piperazinyl wherein N$_4$ in 1-piperaizinyl is substituted with 0–1 substituents selected from the group R$^{2t}$, CO$_2$R$^{2q}$, COR$^{2q}$ and SO$_2$R$^{2q}$;

$R^{2t}$ is selected from H, $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl ($C_{1-4}$ alkyl)-, heteroaryl and heteroaryl ($C_{1-4}$ alkyl);

$R^3$ is an aryl or heteroaryl group attached through an unsaturated carbon atom of the heteroaryl group;

aryl is selected from phenyl, naphthyl, indanyl and indenyl, each aryl being substituted with 0–5 substituents independently selected at each occurrence from $C_{1-6}$ alkyl, $C_{3-6}$ cycloalkyl, methylenedioxy, $C_{1-4}$ alkyloxy-$C_{1-4}$ alkyloxy, —$OR^{2m}$, Br, Cl, F, I, $C_{1-4}$ haloalkyl, —CN, —$NO_2$, —SH, —$S(O)_nR^{2n}$, —$COR^{2m}$, —$CO_2R^{2m}$, —$OC(O)R^{2n}$, —$NR^{2g}COR^{2m}$, —$N(COR^{2m})_2$, —$NR^{2g}CONR^{2o}R^{2p}$, —$NR^{2g}CO_2R^{2h}$, —$NR^{2o}R^{2p}$ and $CONR^{2o}R^{2p}$ and up to 1 phenyl, each phenyl substituent being substituted with 0–4 substituents selected from the group $C_{1-3}$ alkyl, $C_{1-3}$ alkoxy, Br, Cl, F, I, —CN, dimethylamino, $CF_3$, $C_2F_5$, $OCF_3$, $SO_2Me$ and acetyl;

heteroaryl is selected from the group pyridyl, pyrimidyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzo-furanyl, 2,3-dihydrobenzothienyl, 2,3-dihydro-benzothienyl-S-oxide, 2,3-dihydrobenzothienyl-s-dioxide, indolinyl, benzoxazolin-2-on-yl, benzodioxolanyl and benzodioxane, each heteroaryl being substitued at 0–4 carbon atoms with a substituent independently selected at each occurrence from the group $C_{1-6}$ alkyl, $C_{3-6}$ cycloalkyl, Br, F, I, $C_{1-4}$ haloalkyl, —CN, $NR^{2g}R^{2h}$, nitro, —$OR^{2m}$, —SH, —$S(O)_nR^{2n}$, $COR^{2m}$, —$CO_2R^{2m}$, —$OC(O)R^{2n}$, —$NR^{2g}COR^{2m}$, —$N(COR^{2m})_2$, —$NR^{2g}CONR^{2o}R^{2p}$ and each heteroaryl being substituted at any nitrogen atom with 0–1 substituents selected from the group, $R^{2g}$, $CO_2R^{3a}$, $COR^{3a}$ and $SO_2R^{3a}$ wherein, $R^{3a}$ is selected from the group $C_{1-6}$ alkyl, $C_{1-4}$ cycloalkyl-$C_{1-6}$ alkyl and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^4$ and $R^5$ are independently selected at each occurrence from H, Br, Cl, F, I, —CN, $C_{1-6}$ alkyl, $C_{2-6}$ alkenyl, $C_{2-6}$ alkynyl, $C_{3-8}$ cycloalkyl, $C_{1-6}$ alkyloxy, $C_{1-6}$ alkylthio, $C_{1-6}$ alkylsulfinyl, $C_{1-6}$ alkylsulfonyl, amino, $C_{1-4}$ alkylamino, ($C_{1-4}$ alkyl)$_2$ amino and phenyl, each phenyl is substituted with 0–3 groups selected from the group consisting of $C_{1-7}$ alkyl, $C_{3-8}$ cycloalkyl, Br, Cl, F, I, —C(O)H, $C_{1-4}$ haloalkyl, nitro, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, $C_{1-6}$ alkylamino and ($C_{1-4}$ alkyl)$_2$ amino and wherein $R^4$ and $R^5$ non-phenyl groups may be substituted with 0–5 substituents selected from OH, halogen, —C(O)H, —$OC_{1-6}$-alkyl and $C_{1-6}$ haloalkyl, $C_{1-6}$ alkyl, and $C_{3-7}$ c-alkyl.

3. The compound according to claim 2 wherein $R^1$ is selected from $C_{1-6}$ alkyl, $C_{3-6}$ cycloalkyl, $C_{1-6}$ alkoxy, $C_{1-6}$ alkylthio, —$XR^{1c}$ wherein $R^1$ is substituted with 0–6 substituents selected from halogen, $C_{1-4}$ alkyl or $C_{1-4}$ haloalkyl;

$R^2$ is selected from substituted-$C_{1-10}$ alkyl, branched $C_{3-10}$ alkyl, $C_{2-10}$ alkenyl, $C_{2-10}$ alkynyl, $C_{3-8}$ cycloalkyl, $C_{3-6}$ cycloalkyl $C_{1-6}$ alkyl, —$NR^{2c}R^{2d}$ wherein, in the case of substituted-$C_{1-10}$ alkyl, 1–3 substitutents are independently selected from the group $R^{2i}$, $R^{2j}$, $R^{2k}$, $C_{1-6}$ alkyl, $C_{2-8}$ alkenyl, $C_{2-8}$ alkynyl, Br, Cl, F, I, $C_{1-4}$ haloalkyl, —$OR^{2g}$, —$NR^{2g}R^{2h}$, —$C_{1-6}$ alkyl$OR^{2g}$, and $C_{3-8}$ cycloalkyl which is substituted with 0–1 $R^{2l}$ and in wich 0–1 carbons of $C_{4-8}$ cycloalkyl is replaced by —O— and wherein the $R^2$ groups, other than substituted-$C_{1-10}$ alkyl, are substituted with 0–3 substituents independently selected from the group $R^{2i}$, $R^{2j}$, $R^{2k}$, $C_{1-6}$ alkyl, $C_{2-8}$ alkenyl, $C_{2-8}$ alkynyl, Br, Cl, F, I, $C_{1-4}$ haloalkyl, —$OR^{2g}$—$NR^{2g}R^{2h}$, —$C_{1-6}$ alkyl$OR^{2g}$, and $C_{3-8}$ cycloalkyl which is substituted with 0–1 $R^{2l}$ and in wich 0–1 carbons of $C_{4-8}$ cycloalkyl is replaced by —O—.

4. The compound according to claim 2 wherein $R^3$ is selected from an aryl group selected from phenyl or substituted versions thereof or a heteroaryl group selected from pyridyl or substituted versions thereof.

5. The compound according to claim 2 wherein $R^2$ is selected from $C_1$ alkyl of the formula —CR'R"R''' wherein R', R" and R''' are independently selected from H, $C_{1-6}$ alkyl, $C_{3-7}$ cycloalkyl, hydroxy$C_{1-6}$ alkyl, $C_{1-6}$ alkyloxy$C_{1-6}$ alkyl, $C_{2-6}$ alkenyl, $C_{1-6}$ alkyloxy, hydroxy, with the proviso that each of R', R" and R''' cannot be H;

or $R^2$ is selected from $NR^{2c}R^{2d}$ wherein $R^4$ and $R^5$ are independently selected from H or $C_{1-6}$ alkyl.

6. The compound according to claim 4 wherein $R^3$ is attached through an unsaturated carbon atom, and is selected from phenyl substituted with 0–5 substituents independently selected at each occurrence from $C_{1-6}$ alkyl, $C_{3-6}$ cycloalkyl, methylenedioxy, $C_{1-4}$ alkyloxy-$C_{1-4}$ alkyloxy, —$OR^{2m}$, Br, Cl, F, I, $C_{1-4}$ haloalkyl, —CN, —$NO_2$, —SH, —$S(O)_2R^{2n}$, —$COR^{2m}$, —$CO_2R^{2n}$, —$OC(O)R^{2n}$, —$NR^{2g}OR^{2m}$, —$N(COR^{2m})_2$, —$NR^{2g}CONR^{2o}R^{2p}$, —$NR^{2g}CO_2R^{2h}$, —$NR^{2o}R^{2p}$ and $CONR^{2o}R^{2p}$ and up to 1 phenyl, each phenyl substituent being substituted with 0–4 substituents selected from the group $C_{1-3}$ alkyl, $C_{1-3}$ alkoxy, Br, Cl, F, I, —CN, dimethylamino, $CF_3$, $C_2F_5$, $OCF_3$, $SO_2Me$ and acetyl; and pyridyl substitued at 0–4 carbon atoms with a substituent independently selected at each occurrence from the group $C_{1-6}$ alkyl, $C_{3-6}$ cycloalkyl, Br, F, I, $C_{1-4}$ haloalkyl, —CN, nitro, —$OR^{2m}$, —SH, —$S(O)_nR^{2n}$, $COR^{2m}$, —$CO_2R^{2m}$, —$OC(O)R^{2n}$, —$NR^{2g}COR^{2m}$, —$N(COR^{2m})_2$, —$NR^2CONR^{2o}R^{2p}$ and each pyridyl being substituted at any nitrogen atom with 0–1 substituents selected from the group $R^{2g}$, $C_2R^{3a}$, $COR^{3a}$ and $SO_2R^{3a}$.

7. A compound of formula (I)

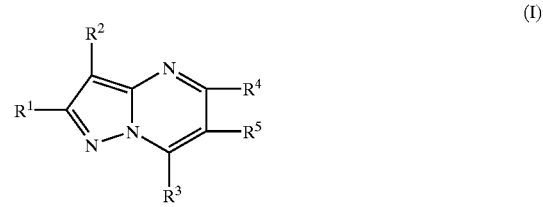

(I)

or a pharmaceutically acceptable salt, stereoisomer or prodrug thereof, wherein $R^1$ is selected from $C_{1-6}$ alkyl, $C_{1-6}$ alkyloxy, —SH or OH;

$R^2$ is selected from $C_{1-4}$ alkyl which is unsubstituted or substituted with 1–4 substitutents selected from $C_{1-6}$ alkyl, $C_{3-8}$ cycloalkyl, $C_{1-6}$ alkyl$OR^{2g}$, $C_{2-6}$ alkenyl or $OR^{2g}$ wherein $R^{2g}$ is H or $C_{1-6}$ alkyl;

$R^3$ is selected from an aryl and a heteroaryl group bonded through an unsaturated carbon atom, wherein said aryl or heteroaryl group is unsubstituted or substituted with 1–4 substituents selected from Cl, F, I, Br, —OH, $CF_3$, $S(O)_nC_{1-6}$ alkyl, —$OC_{1-6}$ alkyl, $C_{1-6}$ alkyl or $NR^{2g}R^{2h}$ wherein $R^{2g}$ and $R^{2h}$ are independently selected from H or $C_{1-6}$ alkyl;

$R^4$ and $R^5$ are independently selected from H, $C_{1-6}$ alkyl or $C_{1-6}$ alkyloxy, with the proviso that when $R^1$ and $R^2$ are unsubstituted, unbranched $C_{1-3}$ alkyl, $R^3$ may not be

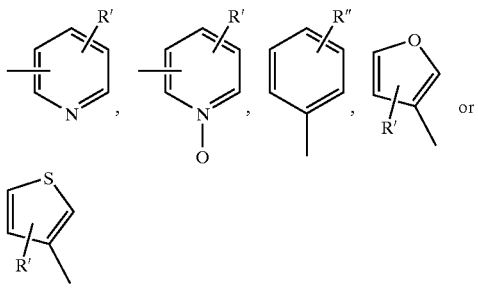

wherein R' is H or $C_{1-3}$ alkyl and R" is H or o-trifluoromethyl, m-trifluoromethyl or m-methoxy.

8. The compound according to claim 7 wherein $R^3$ is substituted with 2–4 substituents.

9. A pharmaceutical composition comprising a compound according to any one of claims 1–8, and a pharmaceutically acceptable carrier.

10. A compound according to claim 2, selected from the group consisting of:

7-(2,4-dichloro-5-fluorophenyl)-2-ethyl-3-(2-pentyl)-pyrazolo[1,5-a]pyrimidine;
7-(2,4-dichlorophenyl)-2-ethyl-6-methyl-3-(2-pentyl)-pyrazolo[1,5-a]pyrimidine;
7-(2-chloro-4-methoxyphenyl)-2-ethyl-3-(2-pentyl)pyrazolo[1,5-a]pyrimidine;
2-ethyl-3-(2-pentyl)-7-(2,4,6-trimethylphenyl)-pyrazolo[1,5-a]pyrimidine;
2-ethyl-3-(2-pentyl)-7-(2,4,6-trimethoxyphenyl)-pyrazolo[1,5-a]pyrimidine;
7-(2,4-dichlorophenyl)-2-ethyl-3-(2-pentyl)pyrazolo[1,5-a]pyrimidine;
7-(2,4-dichlorophenyl)-2-ethylpyrazolo[1,5-a]pyrimidine-3-carboxaldehyde;
7-(2,4-dichlorophenyl)-2-ethyl-3-(1-hydroxyethyl)-pyrazolo[1,5-a]pyrimidine;
7-(2,4-dichlorophenyl)-3-(1-ethoxyethyl)-2-ethyl-pyrazolo[1,5-a]pyrimidine;
7-(2,4-dichlorophenyl)-3-(1-ethoxyethyl)-2-ethylpyrazolo[1,5-a]pyrimidine;
2-ethyl-7-(2-methyl-4-methoxyphenyl)-3-(3-pentyl)-pyrazolo[1,5-a]pyrimidine;
2-ethyl-7-(2-methyl-4-methoxyphenyl)-3-(2-pentyl)-pyrazolo[1,5-a]pyrimidine;
7-(2,4-dimethyiphenyl)-2-ethyl-3-(2-pentyl)-pyrazolo[1,5-a]pyrimidine;
7-(2,4-dichlorophenyl)-2-ethyl-5-methylthio-3-(2-pentyl)-pyrazolo[1,5-a]pyrimidine;
7-(2,4-dichlorophenyl)-2-ethyl-3-(6-methyl-5-hepten-2-yl)-pyrazolo[1,5-a]pyrimidine;
7-(2,4-dichlorophenyl)-2-ethyl-3-(1-hydroxy-4-pentyl)-pyrazolo[1,5-a]pyrimidine;
7-(4-difluoromethoxy-2-methyl)-2-ethyl-3-(3-pentyl)pyrazolo[1,5-a]pyrimidine;
7-(4-difluoromethoxy-2-methyl)-2-ethyl-3-(2-pentyl)pyrazolo[1,5-a]pyrimidine;
7-(2-chloro-4-difluoromethoxyphenyl)-2-ethyl-3-(3-pentyl)pyrazolo[1,5-a]pyrimidine;
7-(2-chloro-4-difluoromethoxyphenyl)-2-ethyl-3-(2-pentyl)pyrazolo[1,5-a]pyrimidine;
7-(2,4-dimethylphenyl)-2-ethyl-3-(3-pentyl)pyrazolo[1,5-a]pyrimidine;
4-(7-(2,4-dichlorophenyl)-2-ethylpyrazolo[1,5-a]pyrimidinyl)pentanoic acid;
4-(7-(2,4-dichlorophenyl)-2-ethylpyrazolo[1,5-a]pyrimidinyl)-N-methylpentanamide;
3-(5-(benzoxazol-2-ylthio)-2-pentyl)-7-(2,4-dichlorophenyl)-2-ethylpyrazolo[1,5-a]pyrimidine;
3-(5-(benzoxazolidinethione-3-yl)-2-pentyl)-7-(2,4-dichlorophenyl)-2-ethylpyrazolo[1,5-a]pyrimidine;
7-(2,4-dichlorophenyl)-2-ethyl-3-(1-hydroxy-2-propyl)-pyrazolo[1,5-a]pyrimidine;
7-(2,4-dichlorophenyl)-3-(1-ethoxy-2-propyl)-2-ethyl-pyrazolo[1,5-a]pyrimidine;
3-(1-acetoxy-2-propyl)-7-(2,4-dichlorophenyl)-2-ethylpyrazolo[1,5-a]pyrimidine;
3-(1-acetoxy-2-butyl)-7-(2,4-dichlorophenyl)-2-ethylpyrazolo[1,5-a]pyrimidine;
7-(2,4-dichlorophenyl)-2-ethyl-3-(1-hydroxy-3-butyl)pyrazolo[1,5-a]pyrimidine;
7-(2,4-dichlorophenyl)-2-ethyl-3-(1-methoxy-3-butyl)pyrazolo[1,5-a]pyrimidine;
7-(2,4-dichlorophenyl)-2-ethyl-3-(3-heptyl)-pyrazolo[1,5-a]pyrimidine;
7-(2,4-dichlorophenyl)-2-ethyl-3-(3-heptyl)-6-methyl-pyrazolo[1,5-a]pyrimidine;
2-ethyl-3-(3-heptyl)-7-(2,4,6-trimethyiphenyl)-pyrazolo[1,5-a]pyrimidine;
7-(2,4-dichlorophenyl)-2-ethyl-3-(3-pentyl)-pyrazolo[1,5-a]pyrimidine;
7-(2,4-dichlorophenyl)-2-ethyl-3-(3-pentyl)-6-methyl-pyrazolo[1,5-a]pyrimidine;
2-ethyl-3-(3-pentyl)-7-(2,4,6-trimethylphenyl)-pyrazolo[1,5-a]pyrimidine; and
2-ethyl-3-(3-pentyl)-7-(2,4,6-trimethoxyphenyl)-pyrazolo[1,5-a]pyrimidine.

11. A compound according to claim 2, selected from the following table:

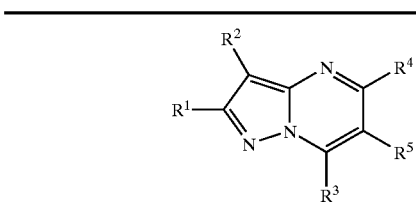

| Ex No | $R^1$ | $R^2$ | $R^4$ | $R^5$ | $R^3$ |
|---|---|---|---|---|---|
| 1 | $C_2H_5$ | $(C_2H_5)_2CH$ | H | H | 2,4-$Cl_2$-$C_6H_3$ |
| 2 | $C_2H_5$ | $(C_2H_5)_2CH$ | H | H | 2-Cl-4-$CH_3O$-$C_6H_3$ |
| 3 | $C_2H_5$ | $(C_2H_5)_2CH$ | H | H | 2,4,6-$(CH_3)_3$-$C_6H_2$ |

-continued

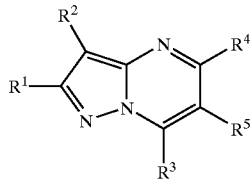

-continued

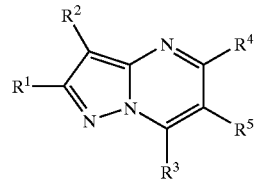

| Ex No | R¹ | R² | R⁴ | R⁵ | R³ |
|---|---|---|---|---|---|
| 4 | $C_2H_5$ | $(C_2H_5)_2CH$ | H | H | 2,4,6-$(OCH_3)_3$-$C_6H_2$ |
| 5 | $C_2H_5$ | $(C_2H_5)_2CH$ | H | H | 2-$(CH_3)_2N$-4-$CH_3$-pyridin-5-yl |
| 6 | $C_2H_5$ | $(C_2H_5)_2CH$ | H | $CH_3$ | 2,4-$Cl_2$-$C_6H_3$ |
| 7 | $C_2H_5$ | $(C_2H_5)_2CH$ | H | $CH_3$ | 2-Cl-4-$CH_3O$-$C_6H_3$ |
| 8 | $C_2H_5$ | $(C_2H_5)_2CH$ | H | $CH_3$ | 2,4,6-$(CH_3)_3$-$C_6H_2$ |
| 9 | $C_2H_5$ | $(C_2H_5)_2CH$ | H | $CH_3$ | 2,4,6-$(OCH_3)_3$-$C_6H_2$ |
| 10 | $C_2H_5$ | $(C_2H_5)_2CH$ | H | $CH_3$ | 2-$(CH_3)_2N$-4-$CH_3$-pyridin-5-yl |
| 11 | $C_2H_5$ | $(C_2H_5)_2CH$ | $CH_3$ | H | 2,4-$Cl_2$-$C_6H_3$ |
| 12 | $C_2H_5$ | $(C_2H_5)_2CH$ | $CH_3$ | H | 2-Cl-4-$CH_3O$-$C_6H_3$ |
| 13 | $C_2H_5$ | $(C_2H_5)_2CH$ | $CH_3$ | H | 2,4,6-$(CH_3)_3$-$C_6H_2$ |
| 14 | $C_2H_5$ | $(C_2H_5)_2CH$ | $CH_3$ | H | 2,4,6-$(OCH_3)_3$-$C_6H_2$ |
| 15 | $C_2H_5$ | $(C_2H_5)_2CH$ | $CH_3$ | H | 2-$(CH_3)_2N$-4-$CH_3$-pyridin-5-yl |
| 16 | $C_2H_5$ | $C_4H_9(C_2H_5)CH$ | H | H | 2,4-$Cl_2$-$C_6H_3$ |
| 17 | $C_2H_5$ | $C_4H_9(C_2H_5)CH$ | H | H | 2-Cl-4-$CH_3O$-$C_6H_3$ |
| 18 | $C_2H_5$ | $C_4H_9(C_2H_5)CH$ | H | H | 2,4,6-$(CH_3)_3$-$C_6H_2$ |
| 19 | $C_2H_5$ | $C_4H_9(C_2H_5)CH$ | H | H | 2,4,6-$(OCH_3)_3$-$C_6H_2$ |
| 20 | $C_2H_5$ | $C_4H_9(C_2H_5)CH$ | H | H | 2-$(CH_3)_2N$-4-$CH_3$-pyridin-5-yl |
| 21 | $C_2H_5$ | $C_4H_9(C_2H_5)CH$ | H | $CH_3$ | 2,4-$Cl_2$-$C_6H_3$ |
| 22 | $C_2H_5$ | $C_4H_9(C_2H_5)CH$ | H | $CH_3$ | 2-Cl-4-$CH_3O$-$C_6H_3$ |
| 23 | $C_2H_5$ | $C_4H_9(C_2H_5)CH$ | H | $CH_3$ | 2,4,6-$(CH_3)_3$-$C_6H_2$ |
| 24 | $C_2H_5$ | $C_4H_9(C_2H_5)CH$ | H | $CH_3$ | 2,4,6-$(OCH_3)_3$-$C_6H_2$ |
| 25 | $C_2H_5$ | $C_4H_9(C_2H_5)CH$ | H | $CH_3$ | 2-$(CH_3)_2N$-4-$CH_3$-pyridin-5-yl |
| 26 | $C_2H_5$ | $C_4H_9(C_2H_5)CH$ | $CH_3$ | H | 2,4-$Cl_2$-$C_6H_3$ |
| 27 | $C_2H_5$ | $C_4H_9(C_2H_5)CH$ | $CH_3$ | H | 2-Cl-4-$CH_3O$-$C_6H_3$ |
| 28 | $C_2H_5$ | $C_4H_9(C_2H_5)CH$ | $CH_3$ | H | 2,4,6-$(CH_3)_3$-$C_6H_2$ |
| 29 | $C_2H_5$ | $C_4H_9(C_2H_5)CH$ | $CH_3$ | H | 2,4,6-$(OCH_3)_3$-$C_6H_2$ |
| 30 | $C_2H_5$ | $C_4H_9(C_2H_5)CH$ | $CH_3$ | H | 2-$(CH_3)_2N$-4-$CH_3$-pyridin-5-yl |
| 31 | $C_2H_5$ | $(C_2H_5)_2N$ | H | H | 2,4-$Cl_2$-$C_6H_3$ |
| 32 | $C_2H_5$ | $(C_2H_5)_2N$ | H | H | 2-Cl-4-$CH_3O$-$C_6H_3$ |
| 33 | $C_2H_5$ | $(C_2H_5)_2N$ | H | H | 2,4,6-$(CH_3)_3$-$C_6H_2$ |
| 34 | $C_2H_5$ | $(C_2H_5)_2N$ | H | H | 2,4,6-$(OCH_3)_3$-$C_6H_2$ |
| 35 | $C_2H_5$ | $(C_2H_5)_2N$ | H | H | 2-$(CH_3)_2N$-4-$CH_3$-pyridin-5-yl |
| 36 | $C_2H_5$ | $(C_2H_5)_2N$ | H | $CH_3$ | 2,4-$Cl_2$-$C_6H_3$ |
| 37 | $C_2H_5$ | $(C_2H_5)_2N$ | H | $CH_3$ | 2-Cl-4-$CH_3O$-$C_6H_3$ |
| 38 | $C_2H_5$ | $(C_2H_5)_2N$ | H | $CH_3$ | 2,4,6-$(CH_3)_3$-$C_6H_2$ |
| 39 | $C_2H_5$ | $(C_2H_5)_2N$ | H | $CH_3$ | 2,4,6-$(OCH_3)_3$-$C_6H_2$ |
| 40 | $C_2H_5$ | $(C_2H_5)_2N$ | H | $CH_3$ | 2-$(CH_3)_2N$-4-$CH_3$-pyridin-5-yl |
| 41 | $C_2H_5$ | $(C_2H_5)_2N$ | $CH_3$ | H | 2,4-$Cl_2$-$C_6H_3$ |
| 42 | $C_2H_5$ | $(C_2H_5)_2N$ | $CH_3$ | H | 2-Cl-4-$CH_3O$-$C_6H_3$ |
| 43 | $C_2H_5$ | $(C_2H_5)_2N$ | $CH_3$ | H | 2,4,6-$(CH_3)_3$-$C_6H_2$ |
| 44 | $C_2H_5$ | $(C_2H_5)_2N$ | $CH_3$ | H | 2,4,6-$(OCH_3)_3$-$C_6H_2$ |
| 45 | $C_2H_5$ | $(C_2H_5)_2N$ | $CH_3$ | H | 2-$(CH_3)_2N$-4-$CH_3$-pyridin-5-yl |
| 46 | $OCH_3$ | $(C_2H_5)_2CH$ | H | H | 2,4-$Cl_2$-$C_6H_3$ |
| 47 | $OCH_3$ | $(C_2H_5)_2CH$ | H | H | 2-Cl-4-$CH_3O$-$C_6H_3$ |
| 48 | $OCH_3$ | $(C_2H_5)_2CH$ | H | H | 2,4,6-$(CH_3)_3$-$C_6H_2$ |
| 49 | $OCH_3$ | $(C_2H_5)_2CH$ | H | H | 2,4,6-$(OCH_3)_3$-$C_6H_2$ |
| 50 | $OCH_3$ | $(C_2H_5)_2CH$ | H | H | 2-$(CH_3)_2N$-4-$CH_3$-pyridin-5-yl |
| 51 | $OCH_3$ | $(C_2H_5)_2CH$ | H | $CH_3$ | 2,4-$Cl_2$-$C_6H_3$ |
| 52 | $OCH_3$ | $(C_2H_5)_2CH$ | H | $CH_3$ | 2-Cl-4-$CH_3O$-$C_6H_3$ |
| 53 | $OCH_3$ | $(C_2H_5)_2CH$ | H | $CH_3$ | 2,4,6-$(CH_3)_3$-$C_6H_2$ |
| 54 | $OCH_3$ | $(C_2H_5)_2CH$ | H | $CH_3$ | 2,4,6-$(OCH_3)_3$-$C_6H_2$ |
| 55 | $OCH_3$ | $(C_2H_5)_2CH$ | H | $CH_3$ | 2-$(CH_3)_2N$-4-$CH_3$-pyridin-5-yl |
| 56 | $OCH_3$ | $(C_2H_5)_2CH$ | $CH_3$ | H | 2,4-$Cl_2$-$C_6H_3$ |
| 57 | $OCH_3$ | $(C_2H_5)_2CH$ | $CH_3$ | H | 2-Cl-4-$CH_3O$-$C_6H_3$ |
| 58 | $OCH_3$ | $(C_2H_5)_2CH$ | $CH_3$ | H | 2,4,6-$(CH_3)_3$-$C_6H_2$ |

-continued

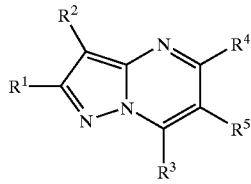

| Ex No | R¹ | R² | R⁴ | R⁵ | R³ |
|---|---|---|---|---|---|
| 59 | OCH$_3$ | (C$_2$H$_5$)$_2$CH | CH$_3$ | H | 2,4,6-(OCH$_3$)$_3$-C$_6$H$_2$ |
| 60 | OCH$_3$ | (C$_2$H$_5$)$_2$CH | CH$_3$ | H | 2-(CH$_3$)$_2$N-4-CH$_3$-pyridin-5-yl |
| 61 | OCH$_3$ | C$_4$H$_9$(C$_2$H$_5$)CH | H | H | 2,4-Cl$_2$-C$_6$H$_3$ |
| 62 | OCH$_3$ | C$_4$H$_9$(C$_2$H$_5$)CH | H | H | 2-Cl-4-CH$_3$O-C$_6$H$_3$ |
| 63 | OCH$_3$ | C$_4$H$_9$(C$_2$H$_5$)CH | H | H | 2,4,6-(CH$_3$)$_3$-C$_6$H$_2$ |
| 64 | OCH$_3$ | C$_4$H$_9$(C$_2$H$_5$)CH | H | H | 2,4,6-(OCH$_3$)$_3$-C$_6$H$_2$ |
| 65 | OCH$_3$ | C$_4$H$_9$(C$_2$H$_5$)CH | H | H | 2-(CH$_3$)$_2$N-4-CH$_3$-pyridin-5-yl |
| 66 | OCH$_3$ | C$_4$H$_9$(C$_2$H$_5$)CH | H | CH$_3$ | 2,4-Cl$_2$-C$_6$H$_3$ |
| 67 | OCH$_3$ | C$_4$H$_9$(C$_2$H$_5$)CH | H | CH$_3$ | 2-Cl-4-CH$_3$O-C$_6$H$_3$ |
| 68 | OCH$_3$ | C$_4$H$_9$(C$_2$H$_5$)CH | H | CH$_3$ | 2,4,6-(CH$_3$)$_3$-C$_6$H$_2$ |
| 69 | OCH$_3$ | C$_4$H$_9$(C$_2$H$_5$)CH | H | CH$_3$ | 2,4,6-(OCH$_3$)$_3$-C$_6$H$_2$ |
| 70 | OCH$_3$ | C$_4$H$_9$(C$_2$H$_5$)CH | H | CH$_3$ | 2-(CH$_3$)$_2$N-4-CH$_3$-pyridin-5-yl |
| 71 | OCH$_3$ | C$_4$H$_9$(C$_2$H$_5$)CH | CH$_3$ | H | 2,4-Cl$_2$-C$_6$H$_3$ |
| 72 | OCH$_3$ | C$_4$H$_9$(C$_2$H$_5$)CH | CH$_3$ | H | 2-Cl-4-CH$_3$O-C$_6$H$_3$ |
| 73 | OCH$_3$ | C$_4$H$_9$(C$_2$H$_5$)CH | CH$_3$ | H | 2,4,6-(CH$_3$)$_3$-C$_6$H$_2$ |
| 74 | OCH$_3$ | C$_4$H$_9$(C$_2$H$_5$)CH | CH$_3$ | H | 2,4,6-(OCH$_3$)$_3$-C$_6$H$_2$ |
| 75 | OCH$_3$ | C$_4$H$_9$(C$_2$H$_5$)CH | CH$_3$ | H | 2-(CH$_3$)$_2$N-4-CH$_3$-pyridin-5-yl |
| 76 | OCH$_3$ | (C$_2$H$_5$)$_2$N | H | H | 2,4-Cl$_2$-C$_6$H$_3$ |
| 77 | OCH$_3$ | (C$_2$H$_5$)$_2$N | H | H | 2-Cl-4-CH$_3$O-C$_6$H$_3$ |
| 78 | OCH$_3$ | (C$_2$H$_5$)$_2$N | H | H | 2,4,6-(CH$_3$)$_3$-C$_6$H$_2$ |
| 79 | OCH$_3$ | (C$_2$H$_5$)$_2$N | H | H | 2,4,6-(OCH$_3$)$_3$-C$_6$H$_2$ |
| 80 | OCH$_3$ | (C$_2$H$_5$)$_2$N | H | H | 2-(CH$_3$)$_2$N-4-CH$_3$-pyridin-5-yl |
| 81 | OCH$_3$ | (C$_2$H$_5$)$_2$N | H | CH$_3$ | 2,4-Cl$_2$-C$_6$H$_3$ |
| 82 | OCH$_3$ | (C$_2$H$_5$)$_2$N | H | CH$_3$ | 2-Cl-4-CH$_3$O-C$_6$H$_3$ |
| 83 | OCH$_3$ | (C$_2$H$_5$)$_2$N | H | CH$_3$ | 2,4,6-(CH$_3$)$_3$-C$_6$H$_3$ |
| 84 | OCH$_3$ | (C$_2$H$_5$)$_2$N | H | CH$_3$ | 2,4,6-(OCH$_3$)$_3$-C$_6$H$_2$ |
| 85 | OCH$_3$ | (C$_2$H$_5$)$_2$N | H | CH$_3$ | 2-(CH$_3$)$_2$N-4-CH$_3$-pyridin-5-yl |

-continued

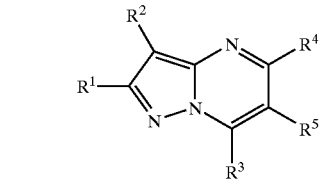

| Ex No | R¹ | R² | R⁴ | R⁵ | R³ |
|---|---|---|---|---|---|
| 86 | OCH$_3$ | (C$_2$H$_5$)$_2$N | CH$_3$ | H | 2,4-Cl$_2$-C$_6$H$_3$ |
| 87 | OCH$_3$ | (C$_2$H$_5$)$_2$N | CH$_3$ | H | 2-Cl-4-CH$_3$O-C$_6$H$_3$ |
| 88 | OCH$_3$ | (C$_2$H$_5$)$_2$N | CH$_3$ | H | 2,4,6-(CH$_3$)$_3$-C$_6$H$_2$ |
| 89 | OCH$_3$ | (C$_2$H$_5$)$_2$N | CH$_3$ | H | 2,4,6-(OCH$_3$)$_3$-C$_6$H$_2$ |
| 90 | OCH$_3$ | (C$_2$H$_5$)$_2$N | CH$_3$ | H | 2-(CH$_3$)$_2$N-4-CH$_3$-pyridin-5-yl |
| 91 | CH$_3$ | (C$_2$H$_5$)$_2$CH | H | H | 2,4-Cl$_2$-C$_6$H$_3$ |
| 92 | OH | (C$_2$H$_5$)$_2$CH | H | CH$_3$ | 2,4-Cl$_2$-C$_6$H$_3$ |
| 93 | C$_2$H$_5$ | (C$_2$H$_5$)$_2$CH | OCH$_3$ | H | 2,4-Cl$_2$-C$_6$H$_3$ |
| 94 | C$_2$H$_5$ | (C$_2$H$_5$)$_2$CH | H | OCH$_3$ | 2,4-Cl$_2$-C$_6$H$_3$ |
| 95 | C$_2$H$_5$ | C$_3$H$_7$(CH$_3$)CH | H | H | 2,4-Cl$_2$-C$_6$H$_3$ |
| 96 | C$_2$H$_5$ | CH$_3$(c-C$_3$H$_5$)CH | H | H | 2,4-Cl$_2$-C$_6$H$_3$ |
| 97 | C$_2$H$_5$ | CH$_3$(c-C$_4$H$_7$)CH | H | H | 2,4-Cl$_2$-C$_6$H$_3$ |
| 98 | C$_2$H$_5$ | (c-C$_3$H$_5$)$_2$CH | H | H | 2,4-Cl$_2$-C$_6$H$_3$ |
| 99 | C$_2$H$_5$ | C$_2$H$_5$(c-C$_3$H$_5$)CH | H | H | 2,4-Cl$_2$-C$_6$H$_3$ |
| 100 | C$_2$H$_5$ | CH$_3$(c-C$_4$H$_7$)CH | H | H | 2,4-Cl$_2$-C$_6$H$_3$ |
| 101 | C$_2$H$_5$ | (HOCH$_2$)$_2$(CH$_3$)C | H | H | 2,4-Cl$_2$-C$_6$H$_3$ |
| 102 | C$_2$H$_5$ | (HOCH$_2$)$_2$(CH$_3$)C | H | H | 2-Cl-4-CH$_3$O-C$_6$H$_3$ |
| 103 | C$_2$H$_5$ | (HOCH$_2$)$_2$(CH$_3$)C | H | H | 2,4,6-(CH$_3$)$_3$-C$_6$H$_2$ |
| 104 | C$_2$H$_5$ | (HOCH$_2$)$_2$(CH$_3$)C | H | H | 2,4,6-(OCH$_3$)$_3$-C$_6$H$_2$ |
| 105 | C$_2$H$_5$ | (HOCH$_2$)$_2$(CH$_3$)C | H | H | 2-(CH$_3$)$_2$N-4-CH$_3$-pyridin-5-yl |
| 106 | C$_2$H$_5$ | (HOCH$_2$)$_2$(CH$_3$)C | H | H | 2,4-Cl$_2$-5-F-C$_6$H$_2$ |
| 107 | C$_2$H$_5$ | (HOCH$_2$)$_2$(CH$_3$)C | H | H | 2-Cl-4-OCH$_3$-5-F |
| 108 | C$_2$H$_5$ | (HOCH$_2$)$_2$(CH$_3$)C | H | H | 2-Cl-4,5-(OCH$_3$)$_2$ |
| 109 | C$_2$H$_5$ | (CH$_3$OCH$_2$)$_2$(CH$_3$)C | H | H | 2,4-Cl$_2$-C$_6$H$_3$ |
| 110 | C$_2$H$_5$ | (CH$_3$OCH$_2$)$_2$(CH$_3$)C | H | H | 2-Cl-4-CH$_3$O-C$_6$H$_3$ |
| 111 | C$_2$H$_5$ | (CH$_3$OCH$_2$)$_2$(CH$_3$)C | H | H | 2,4,6-(CH$_3$)$_3$-C$_6$H$_2$ |
| 112 | C$_2$H$_5$ | (CH$_3$OCH$_2$)$_2$(CH$_3$)C | H | H | 2,4,6-(OCH$_3$)$_3$-C$_6$H$_2$ |
| 113 | C$_2$H$_5$ | (CH$_3$OCH$_2$)$_2$(CH$_3$)C | H | H | 2-(CH$_3$)$_2$N-4-CH$_3$-pyridin-5-yl |
| 114 | C$_2$H$_5$ | (CH$_3$OCH$_2$)$_2$(CH$_3$)C | H | H | 2,4-Cl$_2$-5-F-C$_6$H$_2$ |
| 115 | C$_2$H$_5$ | (CH$_3$OCH$_2$)$_2$(CH$_3$)C | H | H | 2-Cl-4-OCH$_3$-5-F |

-continued

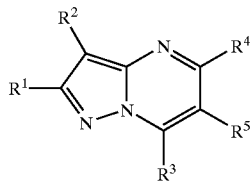

| Ex No | R¹ | R² | R⁴ | R⁵ | R³ |
|---|---|---|---|---|---|
| 116 | C₂H₅ | (CH₃OCH₂)₂(CH₃)C | H | H | 2-Cl-4,5-(OCH₃)₂ |
| 117 | C₂H₅ | (H₂C=CH)₂(CH₃)C | H | H | 2,4-Cl₂-C₆H₃ |
| 118 | C₂H₅ | (H₂C=CH)₂(CH₃)C | H | H | 2-Cl-4-CH₃O-C₆H₃ |
| 119 | C₂H₅ | (H₂C=CH)₂(CH₃)C | H | H | 2,4,6-(CH₃)₃-C₆H₂ |
| 120 | C₂H₅ | (H₂C=CH)₂(CH₃)C | H | H | 2,4,6-(OCH₃)₃-C₆H₂ |
| 121 | C₂H₅ | (H₂C=CH)₂(CH₃)C | H | H | 2-(CH₃)₂N-4-CH₃-pyridin-5-yl |
| 122 | C₂H₅ | (H₂C=CH)₂(CH₃)C | H | H | 2,4-Cl₂-5-F-C₆H₂ |
| 123 | C₂H₅ | (H₂C=CH)₂(CH₃)C | H | H | 2-Cl-4-OCH₃-5-F |
| 124 | C₂H₅ | (H₂C=CH)₂(CH₃)C | H | H | 2-Cl-4,5-(OCH₃)₂ |
| 125 | C₂H₅ | (c-C₃H₅)₂(CH₃)C | H | H | 2,4-Cl₂-C₆H₃ |
| 126 | C₂H₅ | (c-C₃H₅)₂(CH₃)C | H | H | 2-Cl-4-CH₃O-C₆H₃ |
| 127 | C₂H₅ | (c-C₃H₅)₂(CH₃)C | H | H | 2,4,6-(CH₃)₃-C₆H₂ |
| 128 | C₂H₅ | (c-C₃H₅)₂(CH₃)C | H | H | 2,4,6-(OCH₃)₃-C₆H₂ |
| 129 | C₂H₅ | (c-C₃H₅)₂(CH₃)C | H | H | 2-(CH₃)₂N-4-CH₃-pyridin-5-yl |
| 130 | C₂H₅ | (c-C₃H₅)₂(CH₃)C | H | H | 2,4-Cl₂-5-F-C₆H₂ |
| 131 | C₂H₅ | (c-C₃H₅)₂(CH₃)C | H | H | 2-Cl-4-OCH₃-5-F |
| 132 | C₂H₅ | (c-C₃H₅)₂(CH₃)C | H | H | 2-Cl-4,5-(OCH₃)₂ |
| 133 | C₂H₅ | (C₂H₅)₂(OH)C | H | H | 2,4-Cl₂-C₆H₃ |
| 134 | C₂H₅ | (C₂H₅)₂(OH)C | H | H | 2-Cl-4-CH₃O-C₆H₃ |
| 135 | C₂H₅ | (C₂H₅)₂(OH)C | H | H | 2,4,6-(CH₃)₃-C₆H₂ |
| 136 | C₂H₅ | (C₂H₅)₂(OH)C | H | H | 2,4,6-(OCH₃)₃-C₆H₂ |
| 137 | C₂H₅ | (C₂H₅)₂(OH)C | H | H | 2-(CH₃)₂N-4-CH₃-pyridin-5-yl |
| 138 | C₂H₅ | (C₂H₅)₂(OH)C | H | H | 2,4-Cl₂-5-F-C₆H₂ |
| 139 | C₂H₅ | (C₂H₅)₂(OH)C | H | H | 2-Cl-4-OCH₃-5-F |
| 140 | C₂H₅ | (C₂H₅)₂(OH)C | H | H | 2-Cl-4,5-(OCH₃)₂ |
| 141 | C₂H₅ | C₂H₅(OCH₃)CH | H | H | 2,4-Cl₂-C₆H₃ |
| 142 | C₂H₅ | C₂H₅(OCH₃)CH | H | H | 2-Cl-4-CH₃O-C₆H₃ |
| 143 | C₂H₅ | C₂H₅(OCH₃)CH | H | H | 2,4,6-(CH₃)₃-C₆H₂ |
| 144 | C₂H₅ | C₂H₅(OCH₃)CH | H | H | 2,4,6-(OCH₃)₃-C₆H₂ |

-continued

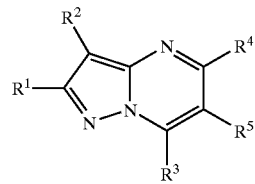

| Ex No | R¹ | R² | R⁴ | R⁵ | R³ |
|---|---|---|---|---|---|
| 145 | C₂H₅ | C₂H₅(OCH₃)CH | H | H | 2-(CH₃)₂N-4-CH₃-pyridin-5-yl |
| 146 | C₂H₅ | C₂H₅(OCH₃)CH | H | H | 2,4-Cl₂-5-F-C₆H₂ |
| 147 | C₂H₅ | C₂H₅(OCH₃)CH | H | H | 2-Cl-4-OCH₃-5-F |
| 148 | C₂H₅ | C₂H₅(OCH₃)CH | H | H | 2-Cl-4,5-(OCH₃)₂ |
| 149 | C₂H₅ | (C₂H₅)₂CH | H | H | 2,4-Cl₂-5-F-C₆H₂ |
| 150 | C₂H₅ | (C₂H₅)₂CH | H | H | 2-Cl-4-OCH₃-5-F |
| 151 | C₂H₅ | (C₂H₅)₂CH | H | H | 2-Cl-4,5-(OCH₃)₂ |
| 152 | C₂H₅ | C₄H₉(C₂H₅)CH | H | H | 2,4-Cl₂-5-F-C₆H₂ |
| 153 | C₂H₅ | C₄H₉(C₂H₅)CH | H | H | 2-Cl-4-OCH₃-5-F |
| 154 | C₂H₅ | C₄H₉(C₂H₅)CH | H | H | 2-Cl-4,5-(OCH₃)₂ |
| 155 | OCH₃ | (C₂H₅)₂CH | H | H | 2,4-Cl₂-5-F-C₆H₂ |
| 156 | OCH₃ | (C₂H₅)₂CH | H | H | 2-Cl-4-OCH₃-5-F |
| 157 | OCH₃ | (C₂H₅)₂CH | H | H | 2-Cl-4,5-(OCH₃)₂ |
| 158 | C₂H₅ | (C₂H₅)₂N | H | H | 2,4-Cl₂-5-F-C₆H₂ |
| 159 | C₂H₅ | (C₂H₅)₂N | H | H | 2-Cl-4-OCH₃-5-F |
| 160 | C₂H₅ | (C₂H₅)₂N | H | H | 2-Cl-4,5-(OCH₃)₂ |
| 161 | C₂H₅ | C₃H₇(CH₃)CH | H | H | 2-Cl-4-CH₃O-C₆H₃ |
| 162 | C₂H₅ | C₃H₇(CH₃)CH | H | H | 2,4,6-(CH₃)₃-C₆H₂ |
| 163 | C₂H₅ | C₃H₇(CH₃)CH | H | H | 2,4,6-(OCH₃)₃-C₆H₂ |
| 164 | C₂H₅ | C₃H₇(CH₃)CH | H | H | 2-(CH₃)₂N-4-CH₃-pyridin-5-yl |
| 165 | C₂H₅ | C₃H₇(CH₃)CH | H | H | 2,4-Cl₂-5-F-C₆H₂ |
| 166 | C₂H₅ | C₃H₇(CH₃)CH | H | H | 2-Cl-4-OCH₃-5-F |
| 167 | C₂H₅ | C₃H₇(CH₃)CH | H | H | 2-Cl-4,5-(OCH₃)₂ |
| 168 | C₂H₅ | (C₂H₅)₂CH | H | H | 2-CH₃-4-OCH₃-5-F-C₆H₂ |
| 169 | OCH₃ | (C₂H₅)₂CH | H | H | 2-CH₃-4-OCH₃-5-F-C₆H₂ |
| 170 | C₂H₅ | C₄H₉(C₂H₅)CH | H | H | 2-CH₃-4-OCH₃-5-F-C₆H₂ |
| 171 | OCH₃ | C₄H₉(C₂H₅)CH | H | H | 2-CH₃-4-OCH₃-5-F-C₆H₂ |
| 172 | C₂H₅ | (C₂H₅)₂N | H | H | 2-CH₃-4-OCH₃-5-F-C₆H₂ |
| 173 | OCH₃ | (C₂H₅)₂N | H | H | 2-CH₃-4-OCH₃-5-F- |

-continued

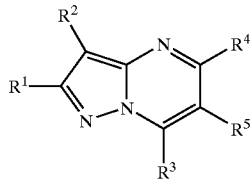

| Ex No | R¹ | R² | R⁴ | R⁵ | R³ |
|---|---|---|---|---|---|
| 174 | $C_2H_5$ | $C_3H_7(CH_3)CH$ | H | H | 2-$CH_3$-4-$OCH_3$-5-F-$C_6H_2$ |
| 175 | $OCH_3$ | $C_3H_7(CH_3)CH$ | H | H | 2-$CH_3$-4-$OCH_3$-5-F-$C_6H_2$ |
| 176 | $C_2H_5$ | $C_2H_5(OCH_3)CH$ | H | H | 2-$CH_3$-4-$OCH_3$-5-F-$C_6H_2$ |
| 177 | $OCH_3$ | $C_2H_5(OCH_3)CH$ | H | H | 2-$CH_3$-4-$OCH_3$-5-F-$C_6H_2$ |
| 178 | $C_2H_5$ | $(C_2H_5)_2CH$ | H | H | 2-$CH_3$-4-$OCH_3$-$C_6H_3$ |
| 179 | $OCH_3$ | $(C_2H_5)_2CH$ | H | H | 2-$CH_3$-4-$OCH_3$-$C_6H_3$ |
| 180 | $C_2H_5$ | $C_4H_9(C_2H_5)CH$ | H | H | 2-$CH_3$-4-$OCH_3$-$C_6H_3$ |
| 181 | $OCH_3$ | $C_4H_9(C_2H_5)CH$ | H | H | 2-$CH_3$-4-$OCH_3$-$C_6H_3$ |
| 182 | $C_2H_5$ | $(C_2H_5)_2N$ | H | H | 2-$CH_3$-4-$OCH_3$-$C_6H_3$ |
| 183 | $OCH_3$ | $(C_2H_5)_2N$ | H | H | 2-$CH_3$-4-$OCH_3$-$C_6H_3$ |
| 184 | $C_2H_5$ | $C_3H_7(CH_3)CH$ | H | H | 2-$CH_3$-4-$OCH_3$-$C_6H_3$ |
| 185 | $OCH_3$ | $C_3H_7(CH_3)CH$ | H | H | 2-$CH_3$-4-$OCH_3$-$C_6H_3$ |
| 186 | $C_2H_5$ | $C_2H_5(OCH_3)CH$ | H | H | 2-$CH_3$-4-$OCH_3$-$C_6H_3$ |
| 187 | $OCH_3$ | $C_2H_5(OCH_3)CH$ | H | H | 2-$CH_3$-4-$OCH_3$-$C_6H_3$ |
| 188 | $C_2H_5$ | $(C_2H_5)_2CH$ | H | H | 2-$CH_3$-4-Cl-$C_6H_3$ |
| 189 | $OCH_3$ | $(C_2H_5)_2CH$ | H | H | 2-$CH_3$-4-Cl-$C_6H_3$ |
| 190 | $C_2H_5$ | $C_4H_9(C_2H_5)CH$ | H | H | 2-$CH_3$-4-Cl-$C_6H_3$ |
| 191 | $OCH_3$ | $C_4H_9(C_2H_5)CH$ | H | H | 2-$CH_3$-4-Cl-$C_6H_3$ |
| 192 | $C_2H_5$ | $(C_2H_5)_2N$ | H | H | 2-$CH_3$-4-Cl-$C_6H_3$ |
| 193 | $OCH_3$ | $(C_2H_5)_2N$ | H | H | 2-$CH_3$-4-Cl-$C_6H_3$ |
| 194 | $C_2H_5$ | $C_3H_7(CH_3)CH$ | H | H | 2-$CH_3$-4-Cl-$C_6H_3$ |
| 195 | $OCH_3$ | $C_3H_7(CH_3)CH$ | H | H | 2-$CH_3$-4-Cl-$C_6H_3$ |
| 196 | $C_2H_5$ | $C_2H_5(OCH_3)CH$ | H | H | 2-$CH_3$-4-Cl-$C_6H_3$ |
| 197 | $OCH_3$ | $C_2H_5(OCH_3)CH$ | H | H | 2-$CH_3$-4-Cl-$C_6H_3$ |
| 198 | $C_2H_5$ | $CH_3OCH_2(CH_3)CH$ | H | H | 2,4-$Cl_2$-$C_6H_3$ |
| 199 | $C_2H_5$ | $CH_3OCH_2(CH_3)CH$ | H | H | 2-Cl-4-$CH_3O$-$C_6H_3$ |
| 200 | $C_2H_5$ | $CH_3OCH_2(CH_3)CH$ | H | H | 2,4,6-$(CH_3)_3$-$C_6H_2$ |
| 201 | $C_2H_5$ | $CH_3OCH_2(CH_3)CH$ | H | H | 2,4,6-$(OCH_3)_3$-$C_6H_2$ |
| 202 | $C_2H_5$ | $CH_3OCH_2(CH_3)CH$ | H | H | 2-$(CH_3)_2N$-4-$CH_3$-pyridin-5-yl |

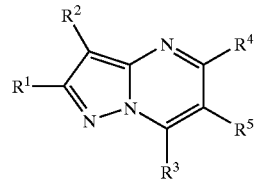

| Ex No | R¹ | R² | R⁴ | R⁵ | R³ |
|---|---|---|---|---|---|
| 203 | $C_2H_5$ | $CH_3OCH_2(CH_3)CH$ | H | H | 2,4,6-$(OCH_3)_3$-$C_6H_2$ |
| 204 | $C_2H_5$ | $CH_3OCH_2(CH_3)CH$ | H | H | 2,4-$Cl_2$-5-F-$C_6H_2$ |
| 205 | $C_2H_5$ | $CH_3OCH_2(CH_3)CH$ | H | H | 2-Cl-4-$OCH_3$-5-F |
| 206 | $C_2H_5$ | $CH_3OCH_2(CH_3)CH$ | H | H | 2-Cl-4,5-$(OCH_3)_2$ |
| 207 | $C_2H_5$ | $CH_3OCH_2(CH_3)CH$ | H | H | 2-$CH_3$-4-$OCH_3$-5-F-$C_6H_2$ |
| 208 | $C_2H_5$ | $CH_3OCH_2(CH_3)CH$ | H | H | 2-$CH_3$-4-$OCH_3$-$C_6H_3$ |
| 209 | $C_2H_5$ | $CH_3OCH_2(CH_3)CH$ | H | H | 2-$CH_3$-4-Cl-$C_6H_3$ |
| 210 | $OCH_3$ | $CH_3OCH_2(CH_3)CH$ | H | H | 2,4-$Cl_2$-$C_6H_3$ |
| 211 | $OCH_3$ | $CH_3OCH_2(CH_3)CH$ | H | H | 2-Cl-4-$CH_3O$-$C_6H_3$ |
| 212 | $OCH_3$ | $CH_3OCH_2(CH_3)CH$ | H | H | 2,4,6-$(CH_3)_3$-$C_6H_2$ |
| 213 | $OCH_3$ | $CH_3OCH_2(CH_3)CH$ | H | H | 2,4,6-$(OCH_3)_3$-$C_6H_2$ |
| 214 | $OCH_3$ | $CH_3OCH_2(CH_3)CH$ | H | H | 2-$(CH_3)_2N$-4-$CH_3$-pyridin-5-yl |
| 215 | $OCH_3$ | $CH_3OCH_2(CH_3)CH$ | H | H | 2,4,6-$(OCH_3)_3$-$C_6H_2$ |
| 216 | $OCH_3$ | $CH_3OCH_2(CH_3)CH$ | H | H | 2,4-$Cl_2$-5-F-$C_6H_2$ |
| 217 | $OCH_3$ | $CH_3OCH_2(CH_3)CH$ | H | H | 2-Cl-4-$OCH_3$-5-F |
| 218 | $OCH_3$ | $CH_3OCH_2(CH_3)CH$ | H | H | 2-Cl-4,5-$(OCH_3)_2$ |
| 219 | $OCH_3$ | $CH_3OCH_2(CH_3)CH$ | H | H | 2-$CH_3$-4-$OCH_3$-5-F-$C_6H_2$ |
| 220 | $OCH_3$ | $CH_3OCH_2(CH_3)CH$ | H | H | 2-$CH_3$-4-$OCH_3$-$C_6H_3$ |
| 221 | $OCH_3$ | $CH_3OCH_2(CH_3)CH$ | H | H | 2-$CH_3$-4-Cl-$C_6H_3$ |
| 222 | $C_2H_5$ | $C_2H_5OCH_2(CH_3)CH$ | H | H | 2,4-$Cl_2$-$C_6H_3$ |
| 223 | $C_2H_5$ | $C_2H_5OCH_2(CH_3)CH$ | H | H | 2-Cl-4-$CH_3O$-$C_6H_3$ |
| 224 | $C_2H_5$ | $C_2H_5OCH_2(CH_3)CH$ | H | H | 2,4,6-$(CH_3)_3$-$C_6H_2$ |
| 225 | $C_2H_5$ | $C_2H_5OCH_2(CH_3)CH$ | H | H | 2,4,6-$(OCH_3)_3$-$C_6H_2$ |
| 226 | $C_2H_5$ | $C_2H_5OCH_2(CH_3)CH$ | H | H | 2-$(CH_3)_2N$-4-$CH_3$-pyridin-5-yl |
| 227 | $C_2H_5$ | $C_2H_5OCH_2(CH_3)CH$ | H | H | 2,4,6-$(OCH_3)_3$-$C_6H_2$ |
| 228 | $C_2H_5$ | $C_2H_5OCH_2(CH_3)CH$ | H | H | 2,4-$Cl_2$-5-F-$C_6H_2$ |
| 229 | $C_2H_5$ | $C_2H_5OCH_2(CH_3)CH$ | H | H | 2-Cl-4-$OCH_3$-5-F |
| 230 | $C_2H_5$ | $C_2H_5OCH_2(CH_3)CH$ | H | H | 2-Cl-4,5-$(OCH_3)_2$ |

-continued

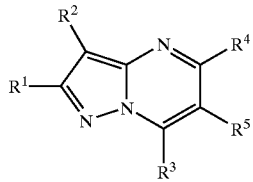

| Ex No | R¹ | R² | R⁴ | R⁵ | R³ |
|---|---|---|---|---|---|
| 231 | C₂H₅ | C₂H₅OCH₂(CH₃)CH | H | H | 2-CH₃-4-OCH₃-5-F-C₆H₂ |
| 232 | C₂H₅ | C₂H₅OCH₂(CH₃)CH | H | H | 2-CH₃-4-OCH₃-C₆H₃ |
| 233 | C₂H₅ | C₂H₅OCH₂(CH₃)CH | H | H | 2-CH₃-4-Cl-C₆H₃ |
| 234 | OCH₃ | C₂H₅OCH₂(CH₃)CH | H | H | 2,4-Cl₂-C₆H₃ |
| 235 | OCH₃ | C₂H₅OCH₂(CH₃)CH | H | H | 2-Cl-4-CH₃O-C₆H₃ |
| 236 | OCH₃ | C₂H₅OCH₂(CH₃)CH | H | H | 2,4,6-(CH₃)₃-C₆H₂ |
| 237 | OCH₃ | C₂H₅OCH₂(CH₃)CH | H | H | 2,4,6-(OCH₃)₃-C₆H₂ |
| 238 | OCH₃ | C₂H₅OCH₂(CH₃)CH | H | H | 2-(CH₃)₂N-4-CH₃-pyridin-5-yl |
| 239 | OCH₃ | C₂H₅OCH₂(CH₃)CH | H | H | 2,4,6-(OCH₃)₃-C₆H₂ |
| 240 | OCH₃ | C₂H₅OCH₂(CH₃)CH | H | H | 2,4-Cl₂-5-F-C₆H₂ |
| 241 | OCH₃ | C₂H₅OCH₂(CH₃)CH | H | H | 2-Cl-4-OCH₃-5-F |
| 242 | OCH₃ | C₂H₅OCH₂(CH₃)CH | H | H | 2-Cl-4,5-(OCH₃)₂ |
| 243 | OCH₃ | C₂H₅OCH₂(CH₃)CH | H | H | 2-CH₃-4-OCH₃-5-F-C₆H₂ |
| 244 | OCH₃ | C₂H₅OCH₂(CH₃)CH | H | H | 2-CH₃-4-OCH₃-C₆H₃ |
| 245 | OCH₃ | C₂H₅OCH₂(CH₃)CH | H | H | 2-CH₃-4-Cl-C₆H₃ |
| 246 | C₂H₅ | CH₃OCH₂(C₂H₅)CH | H | H | 2,4-Cl₂-C₆H₃ |
| 247 | C₂H₅ | CH₃OCH₂(C₂H₅)CH | H | H | 2-Cl-4-CH₃O-C₆H₃ |
| 248 | C₂H₅ | CH₃OCH₂(C₂H₅)CH | H | H | 2,4,6-(CH₃)₃-C₆H₂ |
| 249 | C₂H₅ | CH₃OCH₂(C₂H₅)CH | H | H | 2,4,6-(OCH₃)₃-C₆H₂ |
| 250 | C₂H₅ | CH₃OCH₂(C₂H₅)CH | H | H | 2-(CH₃)₂N-4-CH₃-pyridin-5-yl |
| 251 | C₂H₅ | CH₃OCH₂(C₂H₅)CH | H | H | 2,4,6-(OCH₃)₃-C₆H₂ |
| 252 | C₂H₅ | CH₃OCH₂(C₂H₅)CH | H | H | 2,4-Cl₂-5-F-C₆H₂ |
| 253 | C₂H₅ | CH₃OCH₂(C₂H₅)CH | H | H | 2-Cl-4-OCH₃-5-F |
| 254 | C₂H₅ | CH₃OCH₂(C₂H₅)CH | H | H | 2-Cl-4,5-(OCH₃)₂ |
| 255 | C₂H₅ | CH₃OCH₂(C₂H₅)CH | H | H | 2-CH₃-4-OCH₃-5-F-C₆H₂ |
| 256 | C₂H₅ | CH₃OCH₂(C₂H₅)CH | H | H | 2-CH₃-4-OCH₃-C₆H₃ |

-continued

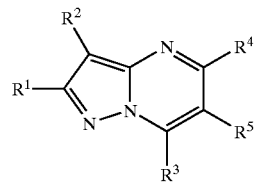

| Ex No | R¹ | R² | R⁴ | R⁵ | R³ |
|---|---|---|---|---|---|
| 257 | C₂H₅ | CH₃OCH₂(C₂H₅)CH | H | H | 2-CH₃-4-Cl-C₆H₃ |
| 258 | OCH₃ | CH₃OCH₂(C₂H₅)CH | H | H | 2,4-Cl₂-C₆H₃ |
| 259 | OCH₃ | CH₃OCH₂(C₂H₅)CH | H | H | 2-Cl-4-CH₃O-C₆H₃ |
| 260 | OCH₃ | CH₃OCH₂(C₂H₅)CH | H | H | 2,4,6-(CH₃)₃-C₆H₂ |
| 261 | OCH₃ | CH₃OCH₂(C₂H₅)CH | H | H | 2,4,6-(OCH₃)₃-C₆H₂ |
| 262 | OCH₃ | CH₃OCH₂(C₂H₅)CH | H | H | 2-(CH₃)₂N-4-CH₃-pyridin-5-yl |
| 263 | OCH₃ | CH₃OCH₂(C₂H₅)CH | H | H | 2,4,6-(OCH₃)₃-C₆H₂ |
| 264 | OCH₃ | CH₃OCH₂(C₂H₅)CH | H | H | 2,4-Cl₂-5-F-C₆H₂ |
| 265 | OCH₃ | CH₃OCH₂(C₂H₅)CH | H | H | 2-Cl-4-OCH₃-5-F |
| 266 | OCH₃ | CH₃OCH₂(C₂H₅)CH | H | H | 2-Cl-4,5-(OCH₃)₂ |
| 267 | OCH₃ | CH₃OCH₂(C₂H₅)CH | H | H | 2-CH₃-4-OCH₃-5-F-C₆H₂ |
| 268 | OCH₃ | CH₃OCH₂(C₂H₅)CH | H | H | 2-CH₃-4-OCH₃-C₆H₃ |
| 269 | OCH₃ | CH₃OCH₂(C₂H₅)CH | H | H | 2-CH₃-4-Cl-C₆H₃ |
| 270 | C₂H₅ | (C₂H₅)₂CH | H | H | 2-Cl-4-CF₃-C₆H₃ |
| 271 | OCH₃ | (C₂H₅)₂CH | H | H | 2-Cl-4-CF₃-C₆H₃ |
| 272 | C₂H₅ | C₄H₉(C₂H₅)CH | H | H | 2-Cl-4-CF₃-C₆H₃ |
| 273 | OCH₃ | C₄H₉(C₂H₅)CH | H | H | 2-Cl-4-CF₃-C₆H₃ |
| 274 | C₂H₅ | (C₂H₅)₂N | H | H | 2-Cl-4-CF₃-C₆H₃ |
| 275 | OCH₃ | (C₂H₅)₂N | H | H | 2-Cl-4-CF₃-C₆H₃ |
| 276 | C₂H₅ | C₃H₇(CH₃)CH | H | H | 2-Cl-4-CF₃-C₆H₃ |
| 277 | OCH₃ | C₃H₇(CH₃)CH | H | H | 2-Cl-4-CF₃-C₆H₃ |
| 278 | C₂H₅ | C₂H₅(OCH₃)CH | H | H | 2-Cl-4-CF₃-C₆H₃ |
| 279 | OCH₃ | C₂H₅(OCH₃)CH | H | H | 2-Cl-4-CF₃-C₆H₃ |
| 280 | C₂H₅ | CH₃OCH₂(CH₃)CH | H | H | 2-Cl-4-CF₃-C₆H₃ |
| 281 | OCH₃ | CH₃OCH₂(CH₃)CH | H | H | 2-Cl-4-CF₃-C₆H₃. |

* * * * *